US010145762B2

(12) United States Patent
Taylor

(10) Patent No.: US 10,145,762 B2
(45) Date of Patent: Dec. 4, 2018

(54) FORENSIC TRACE EVIDENCE MATERIAL COLLECTION, ANALYSIS AND DISTRIBUTION SYSTEM

(71) Applicant: James David Taylor, Maryland Heights, MO (US)

(72) Inventor: James David Taylor, Maryland Heights, MO (US)

(73) Assignee: AARDVARK FORENSICS, LLC, Arnold, MO (US)

( * ) Notice: Subject to any disclaimer, the term of this patent is extended or adjusted under 35 U.S.C. 154(b) by 0 days.

(21) Appl. No.: 15/696,719

(22) Filed: Sep. 6, 2017

(65) Prior Publication Data

US 2018/0080855 A1 Mar. 22, 2018

Related U.S. Application Data

(60) Provisional application No. 62/384,166, filed on Sep. 6, 2016.

(51) Int. Cl.
*G01N 1/02* (2006.01)
*A61B 10/00* (2006.01)
(Continued)

(52) U.S. Cl.
CPC ............ *G01N 1/02* (2013.01); *A61B 10/0045* (2013.01); *C09J 7/02* (2013.01); *C09J 7/04* (2013.01);
(Continued)

(58) Field of Classification Search
CPC ........ G01N 1/02; G01N 1/2813; G01N 21/01; G01N 21/255; G01N 2001/007;
(Continued)

(56) References Cited

U.S. PATENT DOCUMENTS 4,805,468 A 2/1989 Choudhry
5,477,863 A 12/1995 Grant
(Continued)

OTHER PUBLICATIONS

Roux, C., et al., Article, "The end of the (forensic science) world as we know it? The example of trace evidence", Phil. Trans. R. Soc. B 370: 20140260, published 2015; downloaded from the internet at http://rstb.royalsocietypublishing.org/content/royptb/370/1674/20140260.full.pdf on Sep. 25, 2017 (8 pgs).
(Continued)

*Primary Examiner* — Lisa Caputo
*Assistant Examiner* — Nathaniel T Woodward
(74) *Attorney, Agent, or Firm* — Stinson Leonard Street LLP

(57) ABSTRACT

A trace evidence material (TEM) collection device is disclosed that enables crime scene investigators to quickly and easily collect, analyze, annotate, securely store and electronically distribute images of large amounts of trace evidence materials and related crime scene information while also helping to comply with required trace evidence recovery procedures and documentation requirements. The TEM collection device includes a reusable handle and cassette drive mechanism, which may be used with a plurality of single-use cassettes. Each cassette includes a TEM collection media (such as a collection tape or swabbing pads attached to a substrate) that when moved across a surface is capable of collecting TEMs located on the surface. Preferably, each cassette also includes a sealing assembly that seals the TEM collection media after collection of the TEMs so as to preserve the collected TEMs.

24 Claims, 38 Drawing Sheets

(51) Int. Cl.
| | |
|---|---|
| *C09J 7/02* | (2006.01) |
| *C09J 7/04* | (2006.01) |
| *G01N 1/28* | (2006.01) |
| *G01N 21/01* | (2006.01) |
| *G01N 21/25* | (2006.01) |
| *G03B 15/02* | (2006.01) |
| *G03B 15/14* | (2006.01) |
| *G03B 17/56* | (2006.01) |
| *G03B 29/00* | (2006.01) |
| *H04N 7/18* | (2006.01) |
| *G01N 1/00* | (2006.01) |

(52) U.S. Cl.
CPC ........... *G01N 1/2813* (2013.01); *G01N 21/01* (2013.01); *G01N 21/255* (2013.01); *G03B 15/02* (2013.01); *G03B 15/14* (2013.01); *G03B 17/561* (2013.01); *G03B 29/00* (2013.01); *H04N 7/181* (2013.01); *G01N 2001/007* (2013.01); *G01N 2001/027* (2013.01); *G01N 2001/028* (2013.01); *G01N 2001/282* (2013.01); *G01N 2001/2833* (2013.01); *G01N 2021/0112* (2013.01); *G01N 2021/0181* (2013.01); *G01N 2021/0187* (2013.01)

(58) Field of Classification Search
CPC ....... G01N 2001/027; G01N 2001/282; G01N 2001/2833; G01N 2021/0112; G01N 2021/0181; G01N 2021/0187; A61B 10/0045; C09J 7/02; C09J 7/04; G03B 15/02; G03B 15/14; G03B 17/561; G03B 29/00; H04N 7/181
See application file for complete search history.

(56) References Cited

U.S. PATENT DOCUMENTS

| | | | | |
|---|---|---|---|---|
| 5,780,305 | A * | 7/1998 | Chisum | B01L 3/508 206/363 |
| 5,874,045 | A | 2/1999 | Chisum | |
| 6,171,260 | B1 | 1/2001 | Hochmeister et al. | |
| 6,538,623 | B1 * | 3/2003 | Parnian | G06F 1/163 224/908 |
| 6,925,896 | B1 * | 8/2005 | Morton | G01N 1/02 15/215 |
| 7,050,715 | B1 * | 5/2006 | Carrington | G03B 15/035 396/182 |
| 7,098,469 | B1 * | 8/2006 | Carrington | G01J 3/02 250/504 H |
| 7,283,230 | B2 | 10/2007 | Ostler et al. | |
| 7,303,532 | B2 | 12/2007 | Bianca | |
| 7,615,761 | B2 | 11/2009 | Hunziker et al. | |
| 7,958,792 | B2 | 6/2011 | Peng et al. | |
| 8,234,940 | B2 | 8/2012 | Duval | |
| 8,474,047 | B2 | 6/2013 | Adelstein et al. | |
| 8,770,642 | B1 * | 7/2014 | Jason | B25B 9/02 294/212 |
| 8,943,910 | B2 * | 2/2015 | Addleman | B01L 3/502707 73/864.71 |
| 2003/0046003 | A1 * | 3/2003 | Smith | G01C 15/00 701/32.2 |
| 2006/0130598 | A1 * | 6/2006 | Driessche | G01N 1/02 73/864.71 |
| 2006/0245176 | A1 * | 11/2006 | Ostler | G01J 3/10 362/109 |
| 2008/0115595 | A1 * | 5/2008 | Duval | G01N 1/02 73/864.71 |
| 2008/0224067 | A1 | 9/2008 | Clark et al. | |
| 2009/0065710 | A1 * | 3/2009 | Hunziker | G01J 3/02 250/459.1 |
| 2011/0033082 | A1 * | 2/2011 | Beckstead | G01J 3/02 382/100 |
| 2011/0185904 | A1 * | 8/2011 | Langle | B01D 46/42 96/19 |
| 2013/0118276 | A1 | 5/2013 | Duval | |
| 2014/0028853 | A1 | 1/2014 | Bennett et al. | |
| 2015/0059580 | A1 * | 3/2015 | Clement | B03C 3/68 96/18 |
| 2015/0233795 | A1 * | 8/2015 | Glattstein | G01N 1/22 436/165 |
| 2016/0279658 | A1 * | 9/2016 | Li | A61B 5/1172 |

OTHER PUBLICATIONS

National Institute of Standards and Technology, U.S. Department of Commerce, Evidence Committee, The National Institute of Justice, Document, "Trace Evidence Recovery Guidelines", Scientific Working Group on Materials Analysis, Jan. 1998 Revision; downloaded from the internet at https://www.nist.gov/sites/default/files/documents/2016/09/22/trace_evidence_recovery_guidelines.pdf on Sep. 29, 2017 (7 pgs).

Shewale, J., et al., Selected pages from a Book, "Forensic DNA Analysis. Current Practices and Emerging Technologies", published by CRC Press, Apr. 19, 2016, pp. 11 and 12 (2 pgs).

International Search Report and Written Opinion dated Dec. 28, 2017 received in related PCT application PCT/US2017/050238 filed on Sep. 6, 2017 (12 pgs).

* cited by examiner

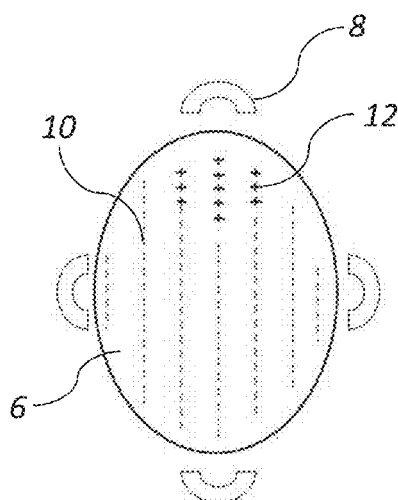
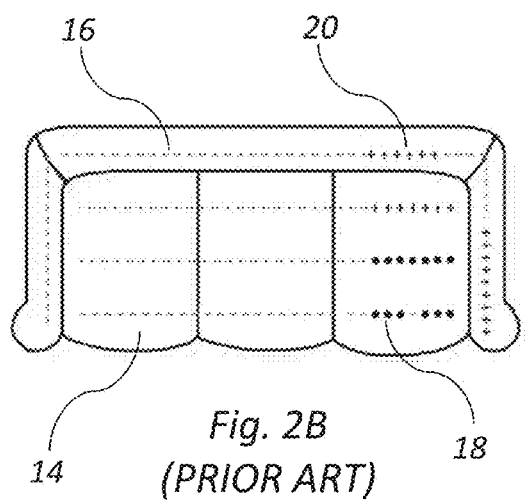
Fig. 2A
(PRIOR ART)
Fig. 2B
(PRIOR ART)
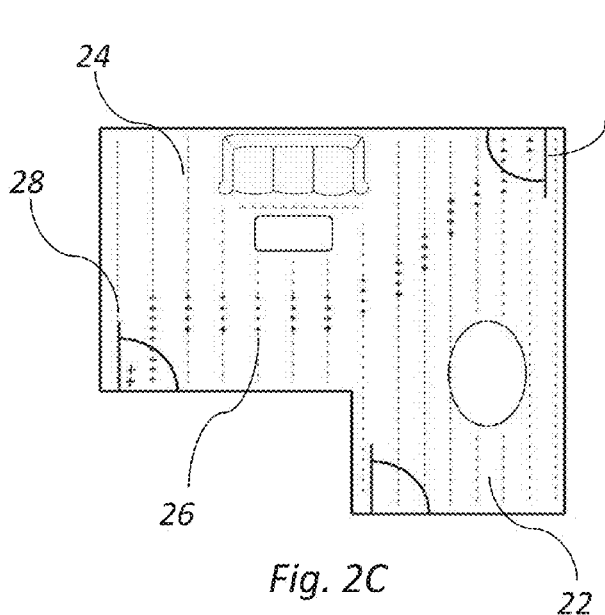
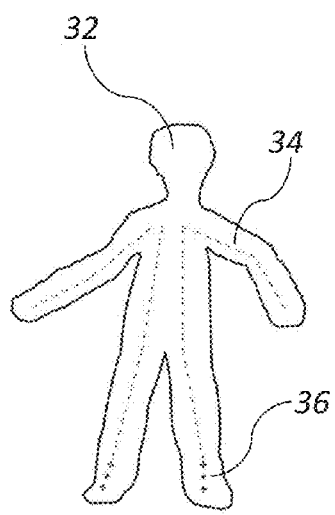
Fig. 2C
(PRIOR ART)
Fig. 2D
(PRIOR ART)

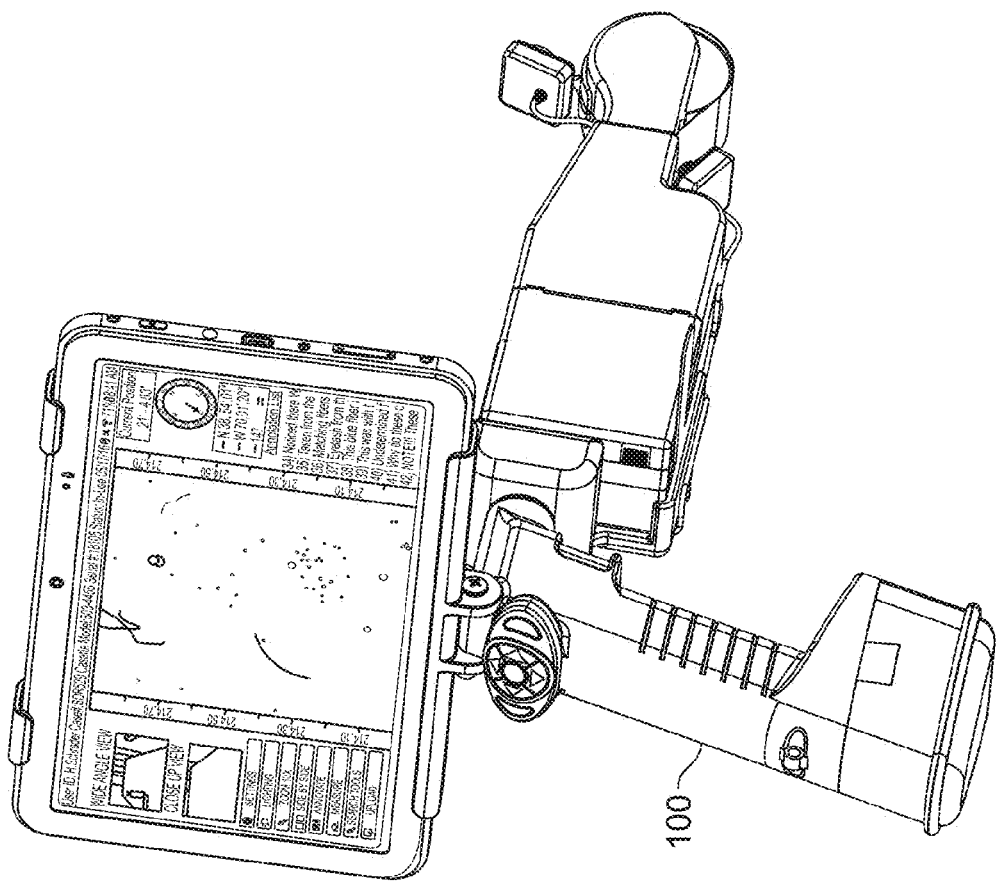

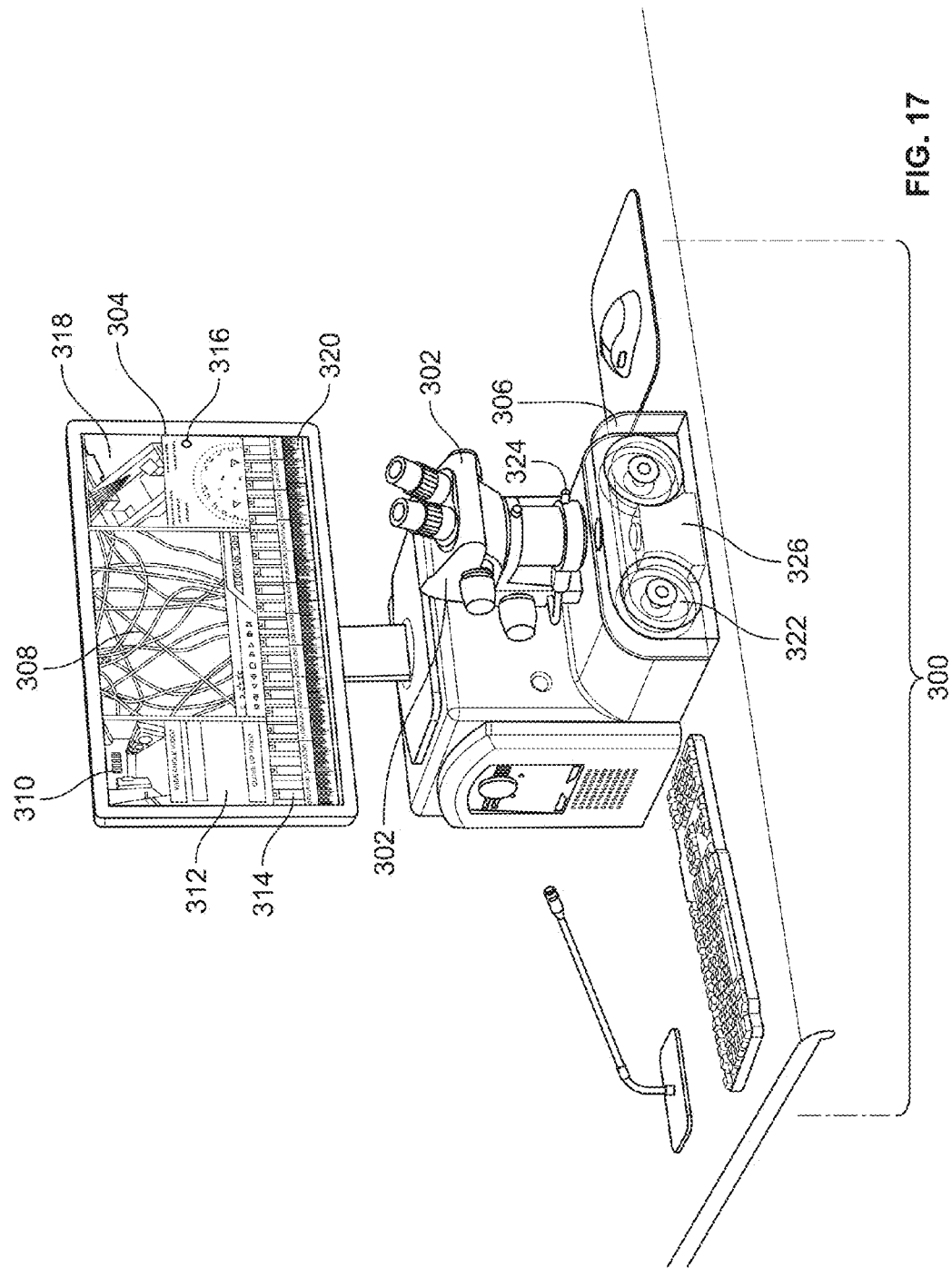

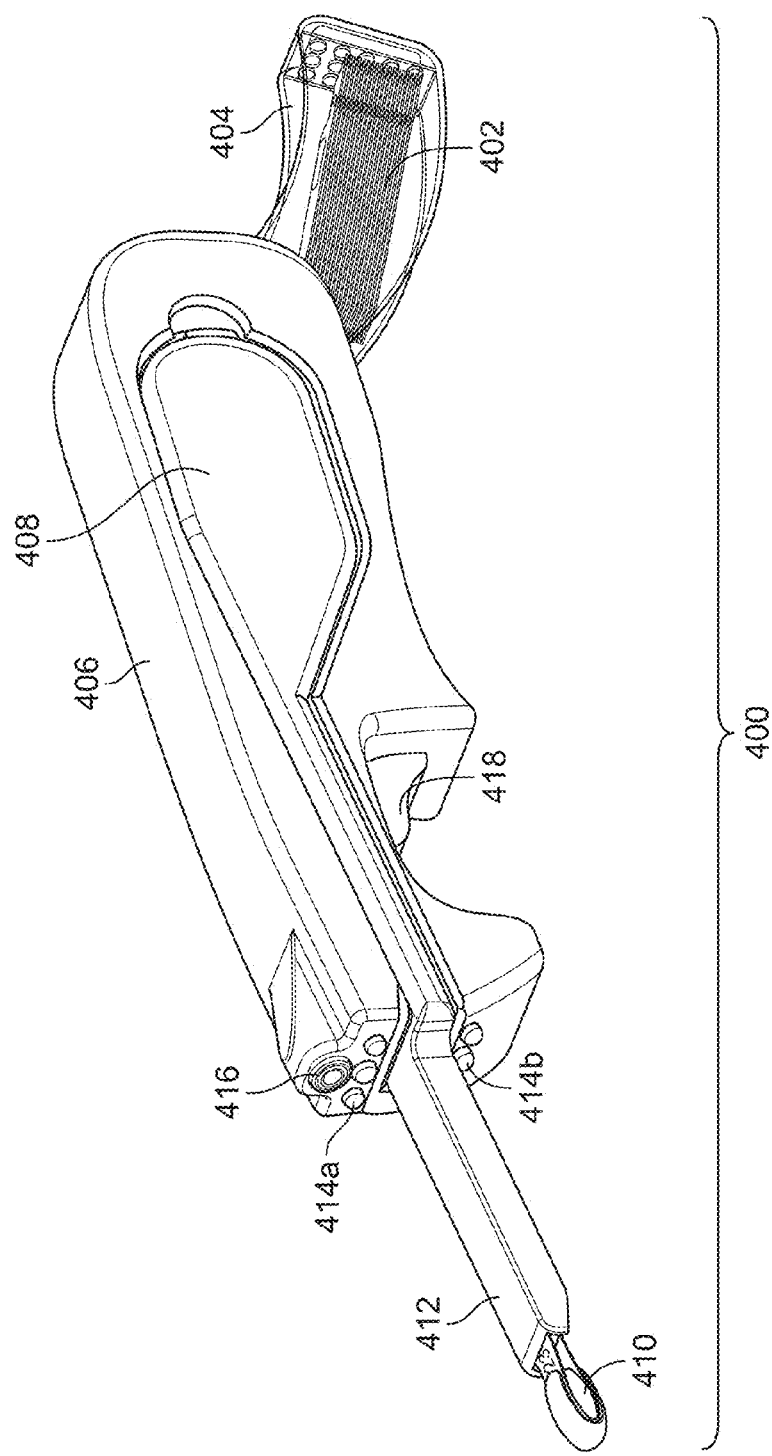

FORENSIC TRACE EVIDENCE MATERIAL COLLECTION, ANALYSIS AND DISTRIBUTION SYSTEM

CROSS-REFERENCE TO RELATED APPLICATIONS

This application is based on and claims priority to U.S. Provisional Application Ser. No. 62/384,166, filed on Sep. 6, 2016, which is incorporated herein by reference in its entirety.

STATEMENT REGARDING FEDERALLY SPONSORED RESEARCH OR DEVELOPMENT

Not applicable.

BACKGROUND OF THE INVENTION

Field of the Invention

The present invention is generally directed to devices and methods used in the field of crime scene investigation (CSI) and, more particularly, to devices and methods used to collect and preserve trace evidence materials (TEMs) found at a potential crime scene.

Description of Related Art

Greater evidentiary and investigative value is constantly being gleaned from traces of materials found at crime scenes insofar as collection of such materials can be used to associate or link objects, individuals and/or locations. A synthetic fiber as small as 0.010 inches in length can be identified and compared to known sources or to similar fibers of unknown sources. A full DNA typing profile can be obtained from as little as 10 nanograms (10 billionths of a gram) of purified DNA. One single pulled hair with an attached root sheath can likewise provide a full DNA profile for DNA comparison. The increased and proper collection of these valuable trace evidence materials (TEMs) at crime scenes is of great importance to solving crimes.

One TEM collection technique involves the use of adhesive tape to collect TEMs. When using adhesive tape, surfaces are "taped" through the application and removal of clear cellulose adhesive tape on a surface that may contain TEMs. The types of materials that may be collected with adhesive tape include, for example, dust, dirt, soil, grit, sand, fingerprints, hair, threads and fibers from carpet, clothing, rope, pollen, skin cells, microorganisms and other biological particulate, small pattern marks or impressions, food particulate, glass particles, paint chips, gun powder residue, and the like.

An exemplary method for collecting TEMs using adhesive tape is shown in FIG. 1. As depicted, a surface is taped through the application and removal of a 5-6 inch strip of clear cellulose adhesive tape 2 on a surface 4 that may contain TEMs. Upon application, the TEMs are effectively "caught on tape." The tape 2 is then removed, carrying the TEMs that are stuck to it, and then the tape 2 is typically stuck to a clear plastic sheet, such as an exhibit bag or loose leaf cover. It is then marked with identification and position information and transported to a remote forensic laboratory for analysis.

One particular method for collecting TEMS using adhesive tape that is suitable for use at a crime scene is referred to as the 1:1 tape collection method. In the 1:1 tape collection method, the taping area represents the surface area from which the TEMs are being removed. The 1:1 tape collection method can be performed in many different ways, such as taping along multiple parallel lines on a surface (i.e., linear taping) or taping along a horizontal/vertical grid or any other pattern that may prove useful to the particular crime scene investigation. This method of collection is particularly helpful in cases where solving a crime depends not only on what materials an investigator finds on a surface, but also on what the investigator can prove with a high degree of certainty was not found on the surface.

FIG. 2A shows a first example of a linear 1:1 tape collection method applied to the surface of a table 6. In this example, the tape was applied to the surface of table 6 as represented by the vertical lines comprised of "I" characters 10 and "+" characters 12. The "I" characters 10 represent areas on the table where no gun powder residue was found on the tape. The "+" characters 12 represent areas on the table where gun powder residue was found on the tape. Those skilled in the art of TEM recovery procedures can deduce that the person who fired the gun was sitting in the north chair 8, which could be crucial evidence in a criminal trial.

FIG. 2B shows a second example of a linear 1:1 tape collection method applied to the surface of a couch 14. In this example, the tape was applied to the surface of couch 14 as represented by the horizontal and vertical lines comprised of "I" characters 16, "·" characters 18, and "+" characters 20. The "I" characters 16 represent areas on the couch where no fibers were found on the tape. The "·" characters 18 represent areas on the couch where blue pants fibers were found on the tape. The "+" characters 20 represent areas on the couch where red sweater fibers were found on the tape. Those skilled in the art of TEM recovery procedures can deduce that the perpetrator sat on the left side of the couch and was wearing blue pants and a red sweater, which could be crucial evidence in a criminal trial.

FIG. 2C shows a third example of a linear 1:1 tape collection method applied to a carpeted floor 22. In this example, the tape was applied to carpeted floor 22 as represented by the vertical lines comprised of "I" characters 24 and "+" characters 26. The "I" characters 24 represent areas on the carpet where no dirt traces were found on the tape. The "+" characters 26 represent areas on the carpet where dirt traces were found on the tape. Those skilled in the art of TEM recovery procedures can deduce that the suspect came in from the bottom left door 28 and exited through the top right door 30 and not the bottom right door. This is an example of where not finding a specific TEM in certain locations can be just as important as where specific TEMs are found.

FIG. 2D shows a fourth example of a linear 1:1 tape collection method applied to a body 32 that was dragged to its current location (which may be deduced due to other evidence such as disturbances in the soil). In this example, the tape was applied to body 32 as represented by lines comprised of "I" characters 34 and "+" characters 36. The "I" characters 34 represent areas on the body where no glove fibers were found on the tape. The "+" characters 36 represent areas on the body where glove fibers were found on the tape. Those skilled in the art of TEM recovery procedures can deduce that the gloves found in the suspect's home contained fibers exactly matching the fibers found on the feet of the body, which supports the theory that the suspect dragged the body to its current location.

Another trace evidence collection technique for collecting TEMS using adhesive tape that is suitable for use at a crime scene is referred to as the zonal tape collection method. This method is used when more precise TEM collection location, such as that derived from the 1:1 tape collection method, is not required. An example of the zonal collection method is when the crime scene investigator takes one or more pieces of tape and repeatedly presses the tape down and lifts it back up again all over an object, such as a pillow. In this case, the precise location of where the TEMs were located on the pillow may not be needed as the investigator may only need to know that the TEMs came from the pillow itself and not exactly where on the pillow they were retrieved from. This zonal TEM collection technique allows the investigator to quickly collect a large amount of TEMs on significantly less tape than methods such as the 1:1 recovery method. Also, a large amount of TEMs can be analyzed on a relatively small piece of tape. In laboratory forensic investigations, tapes and their TEM contents are often manually inspected under a high magnification forensic microscope. This can be both time consuming and may also cause significant operator fatigue, which can result in the examiner missing or misidentifying important TEMs. Therefore, reducing the amount of tape that has to be examined can be beneficial when the precise location of the TEMs on a given surface is not required.

Another trace evidence collection technique involves the use of swab sticks to collect touch DNA left behind during the commission of a crime. In some cases, the swab sticks are comprised of cotton wrapped around one end of a wooden or plastic stick (similar to Q-Tips used for ear cleaning). In other cases, the cotton is replaced with materials that offer superior performance properties due to their ability to release more of the collected touch DNA than a typical cotton swab stick.

The process of extracting touch DNA for forensic analysis involves swabbing a surface with a swab stick to collect trace amounts of epithelial cells, blood, semen, saliva, urine, bone, and other tissue. Examples of surfaces that can be swabbed to collect touch DNA include, for example, doorknobs, countertops, windows, tools, baggies, notes, documents, fingerprints on a victim's hands, neck, face, limbs, or ligatures, handcuffs, shoe strings, firearms, knife handles, weapon handles, clothing items such as hats, masks, gloves, or glasses, automobile surfaces such as steering wheels, air vents, dash controls, or airbags, or even food. This starter DNA is then amplified using polymerase chain reaction (PCR) technology to create identical copies that are large enough for proper analysis. The amount of starter DNA needed to yield a full DNA profile with most commercially available amplification kits is approximately 1 nanogram (ng) of DNA, and partial profiles can be obtained with even less starter material.

Touch DNA swabbing has revolutionized crime scene investigations due to its ability to derive evidence where there is a lack of visible DNA. It can also be used on fingerprints that are too smudged or incomplete for fingerprint analysis. In addition, investigators assigned to cold cases in which the samples were too small or degraded to prove useful years ago are now resubmitting that evidence to labs for touch DNA analysis.

DNA testing for forensic analysis is only as effective as the sample collection methods. Contamination of samples can become a huge issue in court—potentially compromising months or even years of detective work with a single stray hair or bead of sweat that has contaminated the sample. As such, personal protective equipment such as gloves, masks, overalls, shoe covers, and hair covers are typically employed at all times during touch DNA swab collection to make sure that the samples are not contaminated. Also, crime scene DNA collection kits are typically equipped with the necessary tools needed for effective DNA swabbing. These kits often include sterile swabs, distilled water or transport media, bindle paper, forceps, a camera, evidence tape, graph paper, and flashlights or forensic lights.

If using a dry swab, the user typically extracts distilled water from a vial using a sterile pipette and applies one drop to the side of the tip. The swab tip is applied to the object of interest and rubbed using moderate pressure from side to side to ensure as much of the swab surface has made contact with the object as possible. The swab is then allowed to air dry and the tip is placed in a dry transport tube or vial. A double swab technique may also be used to improve the quality of DNA swab profiles, in which a second dry swab is used to collect the remainder of the sample from the same spot. The swabs must be completely dry during transport to prevent mold and other bacterial growth.

Traditionally, swabs have been dried and then transported in an envelope or drying box identified with a unique evidence ID label that holds approximately four to six swabs upright so that the tips do not come into contact with anything and risk contamination. In recent years, specially designed breathable collection tubes have been used because of their convenience and effectiveness in preserving samples. These tubes often include a re-closable dry transport device (typically a box) along with evidence ID labels.

In the area of forensic trace evidence recovery, adherence to proper procedures is of the utmost importance. The failure to follow these procedures and the improper collection of TEMs and/or the accidental contamination of TEMs can produce inaccurate results. Not only can this lead to misinformation, but improper collection and handling of forensic TEMs can be used to dismiss other valid data as invalid evidence.

Sometimes the most thorough examination of crime scene TEMs is done significantly later at a remote forensic examination laboratory by CSI personnel who have never actually been to the crime scene. This issue along with the often limited TEM collection information generated using traditional methods (photographs, notes, etc.) can lead to a large "time and information gap" between the collection of the TEMs at the crime scene and their detailed examination at a forensic examination laboratory. This time and information gap can severely hinder the ability of the crime scene investigators and lab-based forensic examiners to use TEMs to quickly solve crimes.

During some crime scene investigations, it is desirable to have many forensic crime scene investigators review the collected TEMs as quickly as possible. But with current methods, the distribution of these TEMs along with all of the related photographs, position notes and other crime scene information can be a very difficult and time consuming process and, thus, makes more extensive use of additional investigators, particularly in remote locations, much less practical.

In addition, not all crimes are solved right away. Some can go unsolved for many years until additional information becomes available that helps investigators to better understand where to spend their effort collecting forensic TEMs. However, by that time, it is typically too late to collect TEMs insofar as they are either no longer present or have been compromised by contamination or movement. Therefore, the ability to collect and securely preserve large amounts of TEMs for long periods of time and retrieve and review them later can be crucial to solving a case even many years after the investigation has "gone cold" or even closed.

Thus, conventional TEM collection methods have several disadvantages, including one or more of the following: (1) the collection and documentation of TEMs can be laborious and time consuming; (2) the overall crime scene documentation (including TEM positional information, notes, photographs and other information) is often limited; (3) it is difficult to determine where desired TEMs might exist and what TEMs to collect with limited resources and time; (4) it is impractical to collect very large numbers of TEMs when trying to prove where particular TEMs were or were not found, particularly in cases where the possible locations of desired TEMs may not even be known until months or even years into an investigation or even after an investigation has closed; (5) the distribution of TEMs along with all of the related crime scene documentation to additional investigators (particularly those in remote locations) is not practical; (6) the time, effort and documentation needed to comply with departmental and government TEM recovery procedures and guidelines (including those relating to trace evidence detection, collection, preservation, documentation, contamination, security, transportation and chain of custody procedures) can greatly limit the number of TEMs collected; (7) the large amount of work and space involved in storing and retrieving from storage large and wide ranging amounts of TEMs; and (8) the potential for TEM contamination, loss or mix up.

BRIEF SUMMARY OF THE INVENTION

The present invention is directed to a system and method that enables crime scene investigators to quickly and easily collect, analyze, annotate, securely store and electronically distribute images of large amounts of trace evidence materials (TEMs) and related crime scene information while also helping to comply with trace evidence recovery procedures, documentation and chain of custody requirements.

In one aspect of the invention, a TEM collection device is provided that includes a number of reusable components, such as a handle, a cassette drive mechanism, and optionally a computing device with a display (such as a tablet), along with a single-use cassette that is attachable to the cassette drive mechanism. The cassette includes a TEM collection media, such as collection tape, that when moved across a surface is capable of collecting TEMs located on the surface. The TEM collection device can be used to facilitate both the highly location specific 1:1 TEM collection method and also the less location specific zonal collection method depending on the requirements of the investigation.

In some embodiments, the cassette includes a supply reel that contains a roll of collection tape having an adhesive side and a non-adhesive back side. The collection tape is fed from the supply reel and wrapped around a roller whereby movement of the roller causes the adhesive side of the collection tape to roll across the surface and collect the TEMs. After collection of the TEMs, the adhesive side of the collection tape is preferably sealed so as to preserve the collected TEMs.

In some embodiments, two separate seals are applied to the collection tape after collection of the TEMs—one on the adhesive side and one on the back side—to enclose the entire collection tape containing the collected TEMs between the seals. In other embodiments, one separate seal is applied to the adhesive side of the collection tape after collection of the TEMs, and the back side of the collection tape serves as the second seal. In both cases, the sealed collection tape may be rolled up and stored on a take-up reel within the cassette, which can be located behind an access point secured by a tamper evident seal until the take-up reel is removed from the cassette in a procedurally secure and documented manner. Alternatively, the sealed collection tape may be cut to provide a sealed segment that is ejected from the device for immediate analysis.

In yet other embodiments, no separate seals are applied after collection of the TEMs and the collection tape itself when rolled up and stored on a take-up reel within the cassette provides the sealing function. Specifically, for each designated segment of rolled collection tape containing collected TEMs, the back side of the collection tape for a previous tape segment on the roll serves as the first seal (i.e., the tape segment whose back side is positioned adjacent the collected TEMs on the roll) and the back side of the designated tape segment containing the collected TEMs serves as the second seal. In this case, the TEMs would be exposed when the rolled tape stored on the take-up reel is unrolled and, as such, the unrolling of the tape would preferably be performed in a controlled manner.

The TEM collection device preferably includes one or more cameras that capture one or more videos and/or photographs to assist in analysis of the TEMs and related crime scene data. A first camera may capture wide angle videos and/or photographs of the crime scene, which includes the surface from which the TEMs are collected, and may include various forms of forensic lighting, filters or other technologies that can be used to enhance visualization of the crimes scene or TEMs. A second camera may capture high resolution, high magnification, close-up videos and/or photographs of the surface prior to collection of the TEMs and may also include various forms of forensic lighting, filters or other technologies that can be used to enhance the ability to search for and visualize the crimes scene or TEMs. A third camera may capture high resolution, high magnification videos and/or photographs of the TEM collection media after collection of the TEMs and may include various forms of forensic foreground, background and side lighting, filters or other technologies that can be used to enhance visualization of the TEMs. The videos and/or photographs captured by the cameras may be presented on the tablet of the TEM collection device. The tablet also enables entry of one or more annotations that are time-correlated with the videos and/or photographs.

In another aspect of the invention, a TEM collection device is provided that includes a number of reusable components, such as a handle and a cassette drive mechanism, along with a single-use cassette that is attachable to the cassette drive mechanism. The cassette includes TEM collection media in the form of a plurality of absorbent swabbing pads spaced along the length of a non-absorbent substrate. Each of the swabbing pads may be rubbed across a surface to collect TEMs (such as touch DNA) located on the surface. A swab moisture applicator may be used to moisten each of the swabbing pads prior to collection of the TEMs. After collection of the TEMs, the swabbing pads are preferably sealed so as to preserve the collected TEMS.

In some embodiments, two separate seals are applied to opposite sides of the substrate/swabbing pads after collection of the TEMs so as to enclose the entire substrate/swabbing pads containing the collected TEMs between the seals. In other embodiments, one separate seal is applied to the side of the substrate with the swabbing pads, and the back side of the substrate serves as the second seal. In both cases, the sealed substrate/swabbing pads may be rolled up and stored on a take-up reel within the cassette. Alternatively, the sealed substrate/swabbing pads may be cut so that there is a sealed and individually numbered swab segment for each swabbing pad to thereby provide a touch DNA sample. The touch DNA samples are then deposited into a swab drying container.

In yet other embodiments, no separate seals are applied after collection of the TEMs and the substrate itself when rolled up and stored on a take-up reel within the cassette provides the sealing function. Specifically, for each swabbing pad containing collected TEMs, the back side of the substrate for a previous substrate segment on the roll serves as the first seal (i.e., the substrate segment whose back side is positioned adjacent the swabbing pad on the roll) and the back side of the substrate segment containing the swabbing pad serves as the second seal. In this case, the swabbing pads containing the collected TEMs would be exposed when the rolled substrate stored on the take-up reel is unrolled and, as such, the unrolling of the substrate would preferably be performed in a controlled manner.

Thus, the present invention provides a TEM collection device having a single-use cassette that when moved across a surface quickly collects, seals, and stores TEMs while also capturing and displaying videos, photographs, TEM position data and other crime scene data that can be quickly analyzed by an investigator at the crime scene. The investigator has the ability to microscopically analyze and annotate their observations regarding the collected TEMs and related crime scene data. Thus, the TEM collection device serves to decrease TEM collection time and cost while also greatly increasing the ability of investigators to use TEMs to solve crimes.

Images of all of the collected TEMs and related crime scene data may also be quickly and easily distributed to a forensic laboratory for further analysis remote from the crime scene. The forensic laboratory examiners are thus provided with extensive information to facilitate their examinations so as to recapture the crime scene as a scientific endeavor. This enables the forensic laboratory examiners to be significant contributors to the crime scene investigation as a whole.

DESCRIPTION OF THE DRAWINGS

Various exemplary embodiments of the present invention are described in detail below with reference to the attached drawing figures, wherein:

FIGS. 2a, 2b, 2c and 2d are top plan views showing examples of conventional 1:1 TEM collection methods and the information that can be derived therefrom;

FIG. 3 is a perspective view of a TEM collection device that utilizes a collection tape to collect TEMs in accordance with one exemplary embodiment of the present invention;

FIG. 17 is a perspective view of a forensic TEM analyzer that may be used in combination with the TEM collection devices described herein;

FIG. 27 is a perspective view of a TEM collection device that utilizes an absorbent swabbing pad to collect touch DNA in accordance with another exemplary embodiment of the present invention;

DETAILED DESCRIPTION OF PREFERRED EMBODIMENT

The present invention is directed to a system and method that enables crime scene investigators to quickly and easily collect, analyze, annotate, securely store and electronically distribute images of large amounts of trace evidence materials (TEMs) and related crime scene information while also helping to comply with trace evidence recovery procedures, documentation and chain of custody requirements. While the invention will be described in detail below with reference to various exemplary embodiments, it should be understood that the invention is not limited to the specific structural configurations or methodologies of these embodiments. In addition, although the exemplary embodiments are described as embodying several different inventive features, one skilled in the art will appreciate that any one of these features could be implemented without the others in accordance with the present invention.

A. Collection Tape Embodiments

An exemplary embodiment of a system in accordance with the present invention is generally comprised of a TEM collection device 100 (shown in FIG. 3) and a forensic TEM analyzer 300 (shown in FIG. 17). Each of these components will be described in detail below.

As shown in FIG. 3, TEM collection device 100 is a hand held device that is used by crime scene investigators to collect, analyze, annotate and securely store and electronically distribute images of large amounts of TEMs and related crime scene information. As described below, TEM collection device 100 is also configured to enable compliance with departmental or government required trace evidence recovery procedures and documentation requirements.

Figure 1:
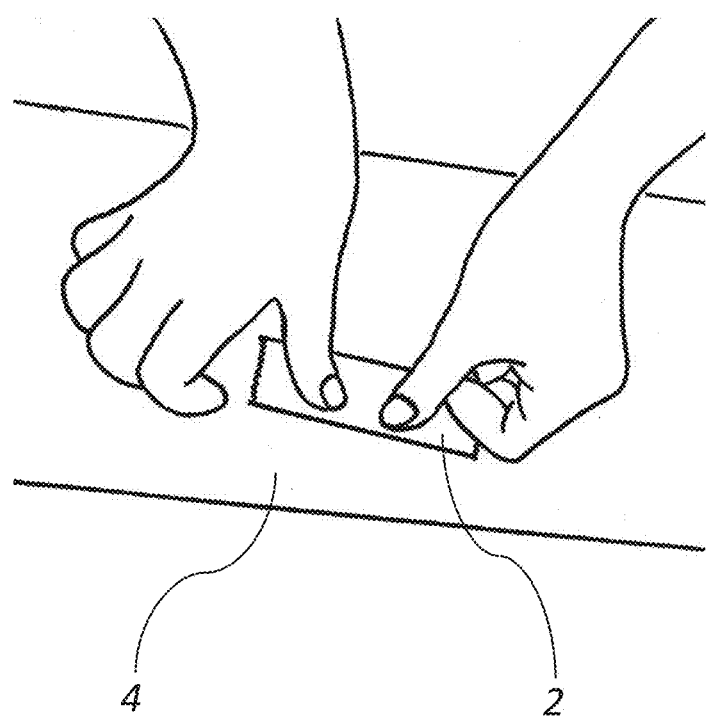
FIG. 1 illustrates a conventional TEM collection method in which a piece of tape is applied to a surface that potentially contains TEMs.
Figure 4:
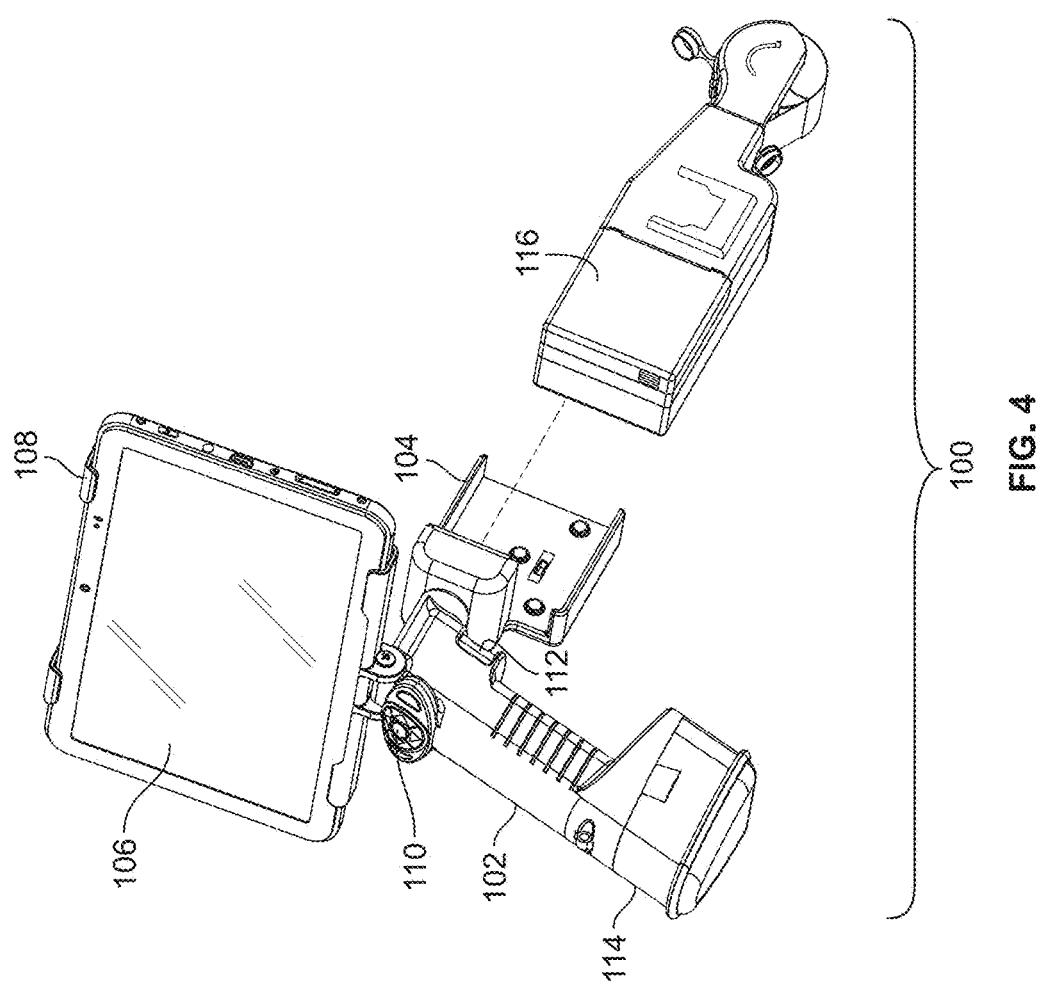
FIG. 4 is a perspective view of the TEM collection device with the TEM collection cassette detached from the cassette drive mechanism.

The main components of TEM collection device 100 are shown in FIG. 4. As can be seen, TEM collection device 100 includes a handle assembly 102, a cassette drive mechanism 104, a touch screen display/CPU 106, a touch screen holder 108, thumb controls 110, a trigger 112 and a rechargeable battery 114. TEM collection device 100 also includes a TEM collection cassette 116 that can be inserted into and retained by cassette drive mechanism 104. In this embodiment, all of the components are reusable with the exception of TEM collection cassette 116, which is a sterile single-use device. Because of the open-faced design of cassette drive mechanism 104, the cassettes (such as TEM collection cassette 116) can be offered in different sizes and varieties. For example, the cassettes may have different widths and/or lengths, or may facilitate the collection of touch DNA or other types of TEM samples. Touch screen display/CPU 106 is comprised of a standard tablet PC, but may alternatively comprise any type of wired or wireless, portable personal computer or other computational device with a user interface as known in the art.

Figure 5:
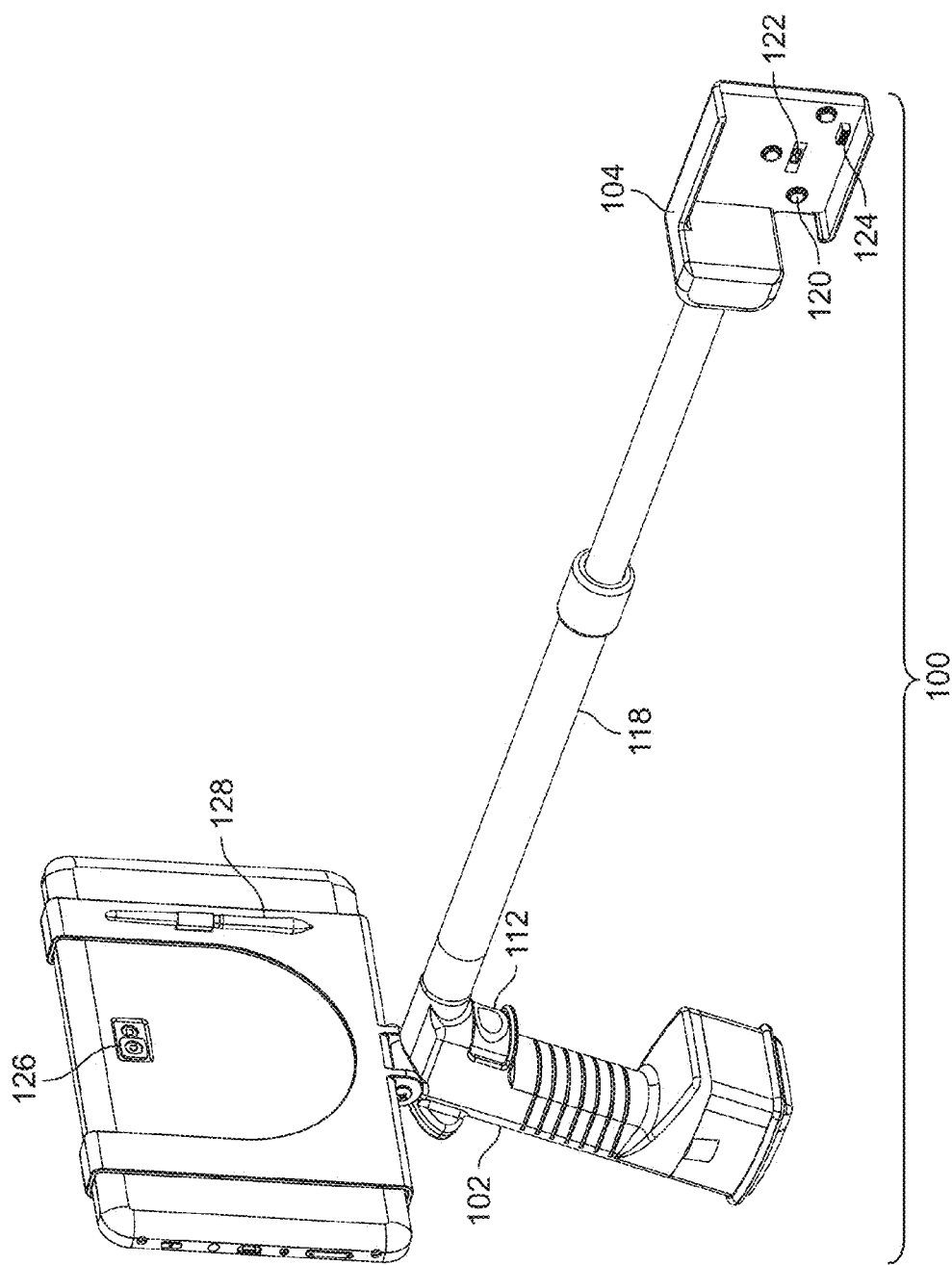
FIG. 5 is a rear perspective view of the TEM collection device with an optional handle shaft used between the handle and the cassette drive mechanism.

FIG. 5 shows an optional accessory handle shaft 118 that may be positioned between handle assembly 102 and cassette drive mechanism 104. Handle shaft 118 has a telescoping configuration that enables adjustment of its length so as to allow an investigator to easily reach TEM collection surfaces, both high and low. Alternatively, the handle shaft could be made of multiple segments that enable length adjustment. Handle shaft 118 is configured so that the electrical and other interconnecting elements that are normally connected between handle assembly 102 and cassette drive mechanism 104 are still in communication with each other regardless of the telescoping nature of handle shaft 118. Of course, handle shaft 118 may be removed completely for compactness as shown in FIGS. 3 and 4.

FIG. 5 also shows various drive and rotational input wheels 120, mechanical actuators 122 and electrical connectors 124 that are implemented between cassette drive mechanism 104 and TEM collection cassette 116, which will be described in greater detail below. Also shown is a forward facing, wide-angle video camera 126 located on the back of touch screen display/CPU 106 that can be made to intermittently or constantly record video or photographs of the crime scene during the TEM collection process and may include various forms of forensic lighting, filters or other technologies that can be used to enhance visualization of various aspects of the crime scene or TEMs. Of course, the camera or others technologies could be located in a different location in accordance with the present invention. A stylus 128 that can be used with touch screen display/CPU 106 is also shown.

Figure 6:
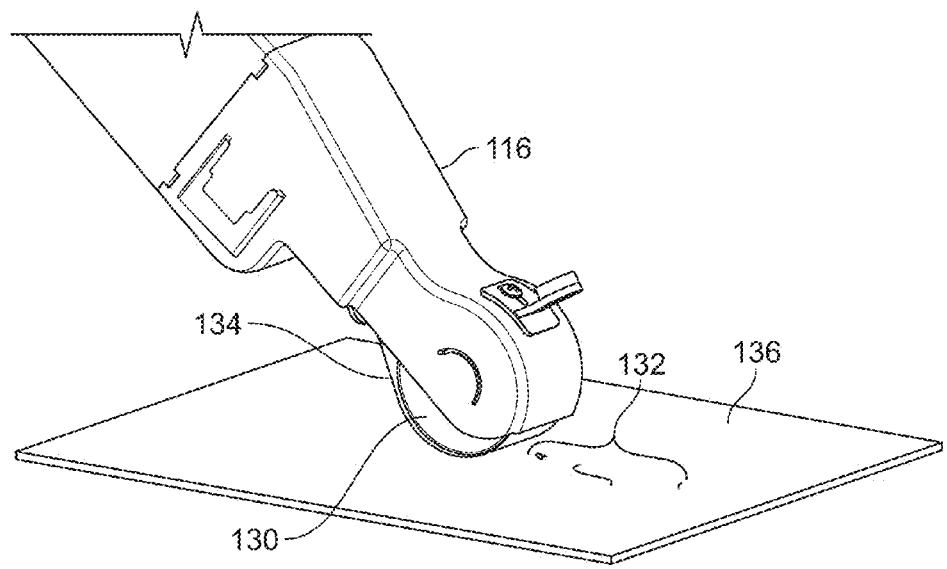
FIG. 6 is a perspective view of the TEM collection cassette being used to collect TEMs from a surface.

As shown in FIG. 6, the operation of TEM collection device 100 is based on the use of an essentially sterile, single-use TEM collection cassette 116 that has the ability to collect and retain TEMs 132 located on a surface 136, such as a table top. TEM collection cassette 116 has a TEM pickup roller 130 located at its front and TEM collection media in the form of an adhesive collection tape 134 that travels around an exposed portion of TEM pickup roller 130. Collection tape 134 has an adhesive side and an opposing non-adhesive side (referred to as the "back side"). In this embodiment, the pulling of trigger 112 on handle assembly 102 allows collection tape 134 wrapped around TEM pickup roller 130 to roll across surface 136 causing collection tape 134 to feed from an internal tape supply reel 150 (shown in FIG. 8) or another suitable source and around to the bottom of TEM pickup roller 130. The width of TEM pickup roller 130 is preferably smaller than that of collection tape 134 so that only the adhesive side of collection tape 134 comes into contact with surface 136 and picks up any TEMs located on surface 136, such as TEMs 132. In some embodiments, TEM pickup roller 130 may be moved both forwards and backwards to collect and retain TEMs located on surface 136, as described further below.

TEM collection cassette 116 has the ability to collect and retain TEMs by other methods, i.e., it is not limited to the use of collection tape 134. In particular, various types of TEM collection medias or substrates may be used to collect and retain TEMs, such as positive and negative polarity charged surfaces, surfaces of various roughness, contours, shapes or protrusions such as small or even microscopic hairs, hooks or loops, conformal coatings or materials, magnetism, expansion/contraction (grasping) capturing, tiny projections that bind with surfaces at a molecular level as a result of van der Waals forces, flockings, vacuum and other collection and adhesion methods well known to one skilled in the art.

Figure 7:
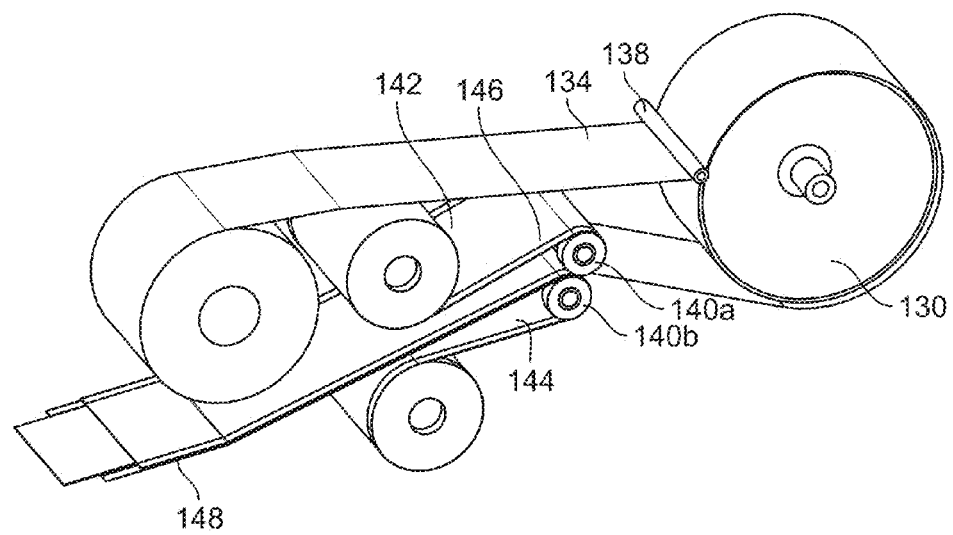
FIG. 7 is a perspective view of the collection tape and seals used in the TEM collection cassette to provide a TEM tape and seal laminate.
Figure 8:
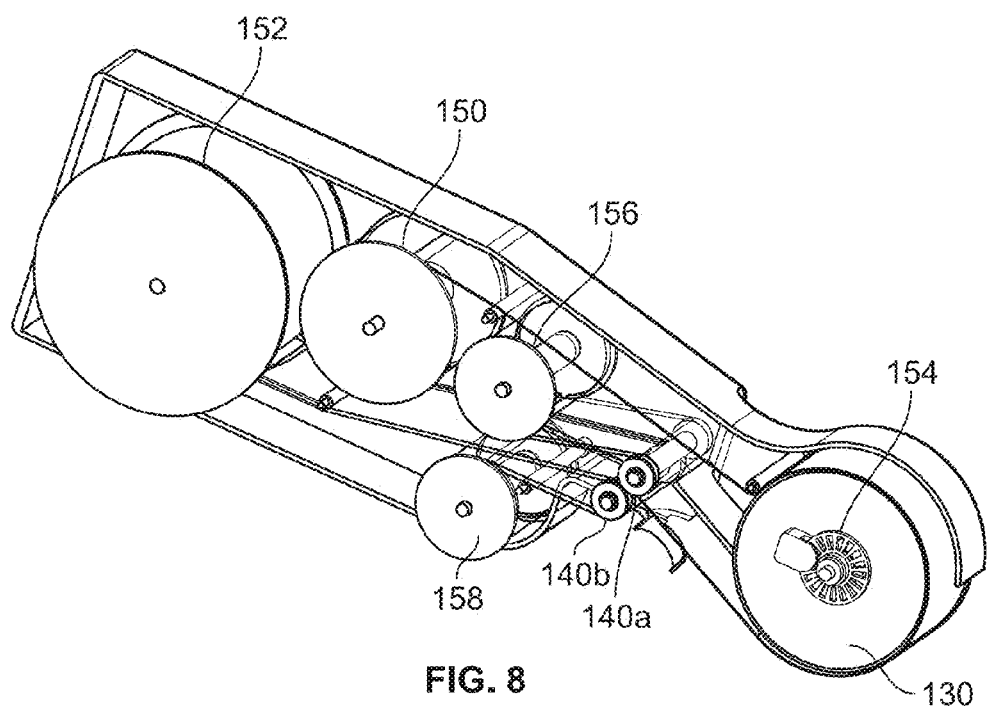
FIG. 8 is a perspective view of the TEM collection cassette with its right housing removed so that the internal components are visible.

FIG. 7 shows collection tape 134 with its associated seals (films) and rollers, wherein the supply and take-up reels for such materials have been omitted for clarity and are shown in FIG. 8. The act of rolling collection tape 134 on TEM pickup roller 130 across surface 136 containing TEMs 132 causes collection tape 134 to feed from tape supply reel 150 (shown in FIG. 8). Collection tape 134 then passes under roller guide 138. Roller guide 138 is preferably made of an inert or other suitable material (such as Teflon) that will not stick to or in any way adversely affect collection tape 134. Collection tape 134 then travels around to the bottom of TEM pickup roller 130 where the adhesive side of collection tape 134 will come into contact with any TEMs 132 located on surface 136. Therefore, collection tape 134 will pick up and retain any TEMs 132 that it comes in contact with.

Immediately after diverging from the bottom of TEM pickup roller 130, collection tape 134 containing TEMs 132 passes between a sealing assembly in the form of seal applicator rollers 140*a* and 140*b*. Seal applicator rollers 140*a* and 140*b* immediately apply a clear upper seal 142 that is fed from upper seal reel 156 (shown in FIG. 8) over collection tape 134 containing TEMs 132 and also a transparent, semi-transparent or opaque lower seal 144 that is fed from lower seal reel 158 (also shown in FIG. 8) to thereby enclose collection tape 134 containing TEMs 132 in between the two seals. One or both of upper and lower seals 142 and 144 may have a peelable and tamper-evident adhesive 146 applied to their side edges so that the seals are adhered together as they pass through seal applicator rollers 140*a* and 140*b*, thereby trapping and isolating TEMs 132 caught on collection tape 134 in between. Alternatively, an upper seal may be sealed to collection tape 134 using adhesive 146 applied to its side edges or by using the adhesive already present on the adhesive side of collection tape 134. In either case, a lower seal may or may not be used. Seal applicator rollers 140*a* and 140*b* are preferably made of a relatively soft elastomer to assist with the compression and therefore adherence of upper and/or lower seals 142 and 144. As shown, each seal applicator roller 140*a* and 140*b* has a small diameter center section that is slightly wider than collection tape 134 so that the tape and TEMs it contains can pass though the center sections without touching seal applicator rollers 140*a* and 140*b*. Application of the seals results in a TEM tape and seal laminate 148, as shown.

It should be understood that the invention is not limited to the use of seal applicator rollers 140*a* and 140*b* and that other sealing assemblies may also be used in accordance with the present invention.

There are many tape and seal material options that could be used in TEM collection cassette 116. Cassettes may also be sold with different material options and sizes for different uses. For example, lower seal may be clear, semi-transparent or opaque and may be white or another color. For wet samples that should be promptly allowed to dry per typical TEM recovery procedures, one or more of the seals can be made of any number of widely available air-permeable materials that can also be transparent. Alternatively, very small holes could be made in one or more of the seals. The tape could include a hydrophilic desiccant or the tape, seals or even the seal adhesive could be made of a hydrophilic desiccant material. The used cassettes could also be returned for factory refurbishment and recertification as a cost saving measure.

FIG. 8 shows TEM collection cassette 116 with its right housing removed so that the internal components are visible. After collection tape 134 containing TEMs 132 is securely sealed, as described above, TEM tape and seal laminate 148 is wrapped up on a take-up reel 152 or it can exit the cassette and be presented directly to the investigator for examination. If exiting the cassette, the investigator can seal the unsealed leading and trailing edges of TEM tape and seal laminate 148 using a standard heat sealer, or the cassette or cassette drive mechanism can be configured in such a way as to automatically seal and cut segments of TEM tape and seal laminate 148 at user selected intervals, as discussed below in connection with FIG. 10. If stored on take-up reel 152, TEM tape and seal laminate 148 can be contained behind a cassette access point, such as door 160 shown in FIG. 9.

In other embodiments, no separate seals are applied after collection of the TEMs and the collection tape itself when rolled up and stored on a take-up reel within the cassette provides the sealing function. Specifically, for each designated segment of rolled collection tape containing collected TEMs, the back side of the collection tape for a previous tape segment on the roll would serve as the first seal (i.e., the tape segment whose back side is positioned adjacent the collected TEMs on the roll) and the back side of the designated tape segment containing the collected TEMs would serve as the second seal. In this case, the TEMs would be exposed when the rolled tape stored on the take-up reel is unrolled and, as such, the unrolling of the tape would preferably be performed in a controlled manner.

One or more of the supply and take-up reels shown in FIG. 8 can be driven by cassette drive mechanism 104 (shown in FIG. 4). This drive mechanism can measure the reel movements by various methods, such as through the use of a rotary position encoder 154 located on TEM pickup roller 130 (shown in FIG. 8) or at another location. Cassette drive mechanism 104 can also monitor component rotations by similar or other means to make sure that they are coordinated with rotary position encoder 154 and therefore the linear movement of collection tape 134. This may also be done to make sure there is no slack in collection tape 134 during use and also to slightly drive collection tape 134 during use so that internal part friction that could potentially hinder the rotation of TEM pickup roller 130 is kept to a minimum by using techniques well known to one skilled in the art.

The device can also be configured so as to allow TEM pickup roller 130 to be moved both forwards and backwards. The device will first seal off any previously exposed portion of collection tape 134 and advance a segregated clean piece of collection tape 134 into a "centered" position on TEM pickup roller 130. Seals are not applied to collection tape 134 while TEM pickup roller 130 is advanced back and forth over surface 136 containing TEMs 132. Alternatively, an easily peel-able adhesive could be used on upper and/or lower seals 142 and 144 or collection tape 134 to allow TEM pickup roller 130 to be moved both forwards and backwards as the seal can be easily pulled apart and reapplied. Cassette drive mechanism 104 can be made to only allow a set amount of back and forth movement of TEM pickup roller 130 by implementing automatic mechanical stops or brakes at the ends of the allowed back and forth travel. When the investigator lets go of trigger 112, the device will then advance and seal off and segregate this section of collection tape 134 and record a date and timestamp note that this section was used using the back and forth collection method. This is also documented by the cameras and onboard data collection, as will be described below.

As with any device that has non-conductive moving parts that slide against each other, there is the potential for the generation of the Tribelectric Effect (more commonly referred to as "static cling") that could affect the use of TEM collection cassette 116. This is particularly true of the tape and seal reels shown in FIG. 8. This potential issue is well understood and readily solvable by one skilled in the art. In addition, various methods can be implemented to reduce the chance of any unwanted "transference" of TEMs from and to unwanted locations.

Figure 9:
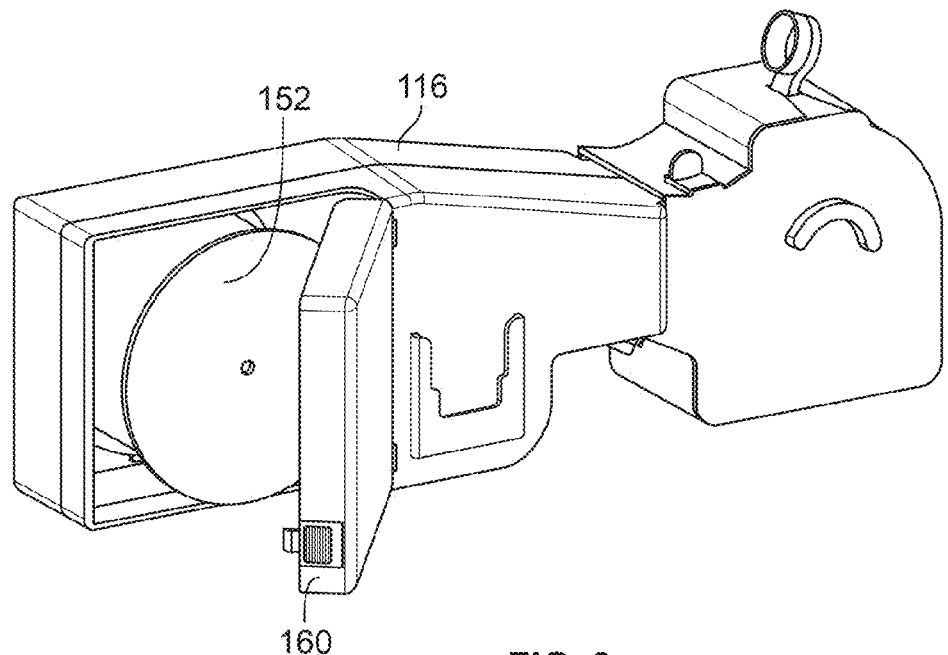
FIG. 9 is a perspective view of the TEM collection cassette with an exposed take-up reel containing TEM tape and seal laminate located behind an access point such as a movable door.

FIG. 9 shows take-up reel 152 of TEM collection cassette 116 located behind an access point, such as a door 160. Door 160 can be secured by a tamper evident seal 162 (shown in FIG. 26A) until such time when it is desirable to remove take-up reel 152 in a procedurally secure and documented manner. It should be noted that if an access point such as door 160 is used, it will come from the manufacturer sealed with a tamper evident seal or similar security means as verification that collection tape 134 and other internal components accessible behind the door have not been tampered with or otherwise adversely compromised since they were manufactured.

Figure 10:
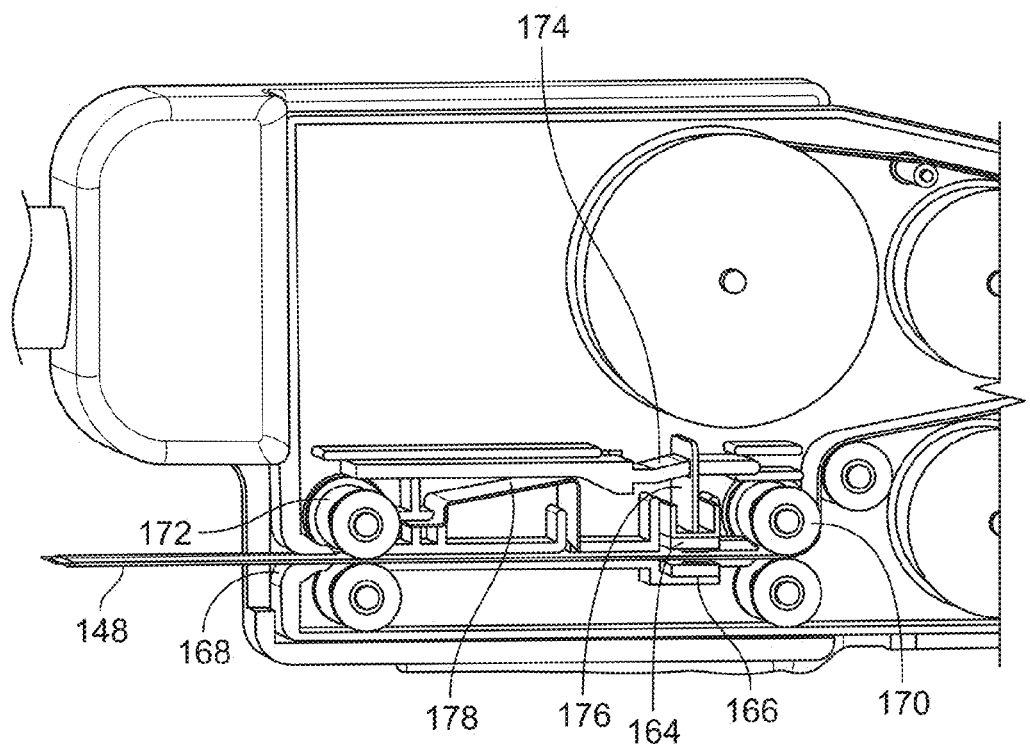
FIG. 10 is a perspective view of a portion of the TEM collection cassette that enables the sealing and cutting of user-selected lengths of TEM tape and seal laminate for immediate viewing and/or analysis.

As shown in FIG. 10, the single-use cassette and/or cassette drive mechanism may be configured in various ways so that they have the ability to seal and cut and then eject user selected lengths of TEM tape and seal laminate 148 for immediate viewing and/or analysis.

In this embodiment, TEM collection cassette 116 includes a seal and cut assembly with a moving, upper sealing pad 164 and a stationary, lower sealing pad 166. Each pad includes a heating element comprised of a thin strip of Ni-chrome metal that is covered by adhesive backed Teflon tape so that the melted/sealed tape does not stick to the heater surfaces. Each heating element is backed by a small block of urethane rubber that acts as a compression spring as the heating elements are pressed towards each other to aid adhesion. Since the device precisely monitors the linear position of TEM tape and seal laminate 148, upon live TEM visualization the investigator can select the start and end points of a sealed and cut portion of TEM tape and seal laminate 148 that can be immediately ejected through exit slot 168 and analyzed if desired without having to wait for an entire tape reel to be used up.

In operation, the investigator selects the "Start Cut and Seal" area on touch screen display/CPU 106 using a simple finger gesture or other input means. Cassette drive mechanism 104 then uses an entry drive wheel 170 and/or an exit drive wheel 172 to move that part of TEM tape and seal laminate 148 to the heat sealing area between moving, upper sealing pad 164 and stationary, lower sealing pad 166. A push-pull solenoid (not shown) built into cassette drive mechanism 104 pushes or pulls the drive mechanism's mechanical actuator 122 (shown in FIG. 5), which in this embodiment has a slot that an externally protruding plastic tab on the backside of the cassette (not shown) engages. This tab is part of a horizontally sliding cam 174, which has an interior right side horizontal tab section that protrudes through a slot in an upper sealing pad piston 176. When the sealer is not being activated, the horizontally sliding cam 174 has a right side horizontal tab having a raised end section that engages the top of a slot in upper sealing pad piston 176 and therefore holds upper sealing pad piston 176 and upper sealing pad 164 above TEM tape and seal laminate 148. When a seal is desired, the solenoid horizontally pushes sliding cam 174 towards the front of the cassette. This movement causes an angled lower section of horizontally sliding cam 174 to push downwards on the bottom part of the slot in upper sealing pad piston 176 and therefore causes upper sealing pad 166 to thrust downwards towards TEM tape and seal laminate 148 so that the two heating elements eventually have the laminate compressed in between them. A voltage source is then momentarily applied to one or both upper and lower heating elements so that they quickly melt and seal TEM tape and seal laminate 148 together in between them at the desired location.

After a heat seal is made, the solenoid and horizontally sliding cam 174 return to their original centered position and therefore the right side horizontal raised end section of the cam reengages the top of the slot in upper sealing pad piston 176 and therefore pushes upper sealing piston 176 and therefore upper sealing pad 164 above TEM tape and seal laminate 148 to its original, non-activated position.

To cut TEM tape and seal laminate 148, entry drive wheel 170 and/or exit drive wheel 172 move the sealed part of TEM seal laminate 148 a short distance to a cutting area that, in this embodiment, is located directly below a spring loaded, angled shearing blade 178. The push-pull solenoid then pulls on horizontally sliding cam 174 via the slot interface in mechanical actuator 122 in which the externally protruding plastic tab on the backside of the cassette (not shown) leftmost lower surface causes the blade to move downwards and cut TEM tape and seal laminate 148. These steps are repeated on the user selected "End Cut and Seal" area and TEM tape and seal laminate 148 is then directed out the back of the cassette and held in place until the user pulls it the rest of the way out. Of course, it should be understood that other types of seal and cut mechanisms may also be used in accordance with the present invention.

Figure 11A:
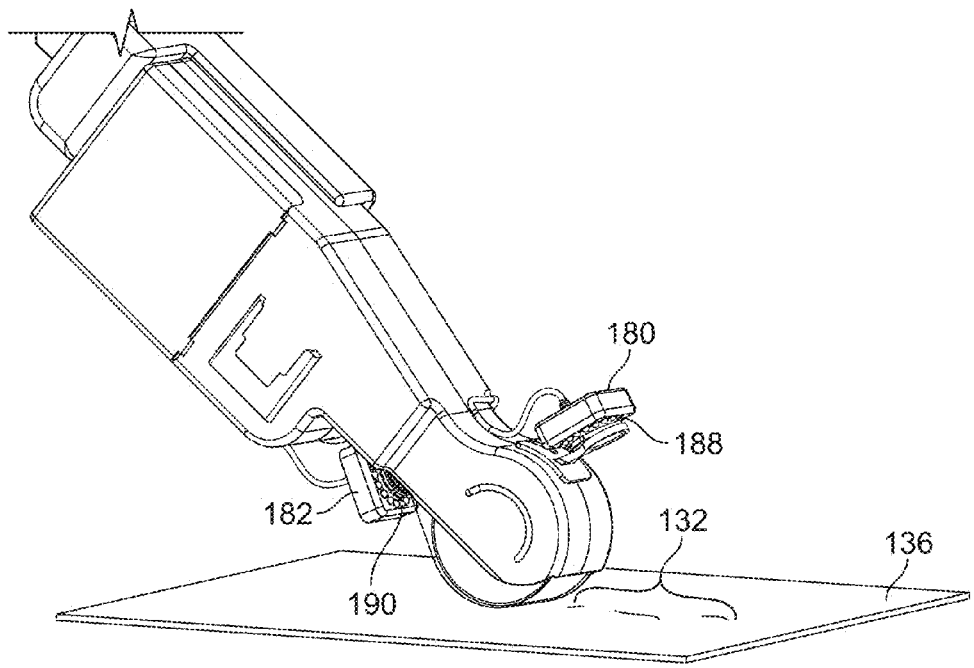
FIGS. 11A and 11B are perspective views of the TEM collection cassette showing its cameras.
Figure 11B:
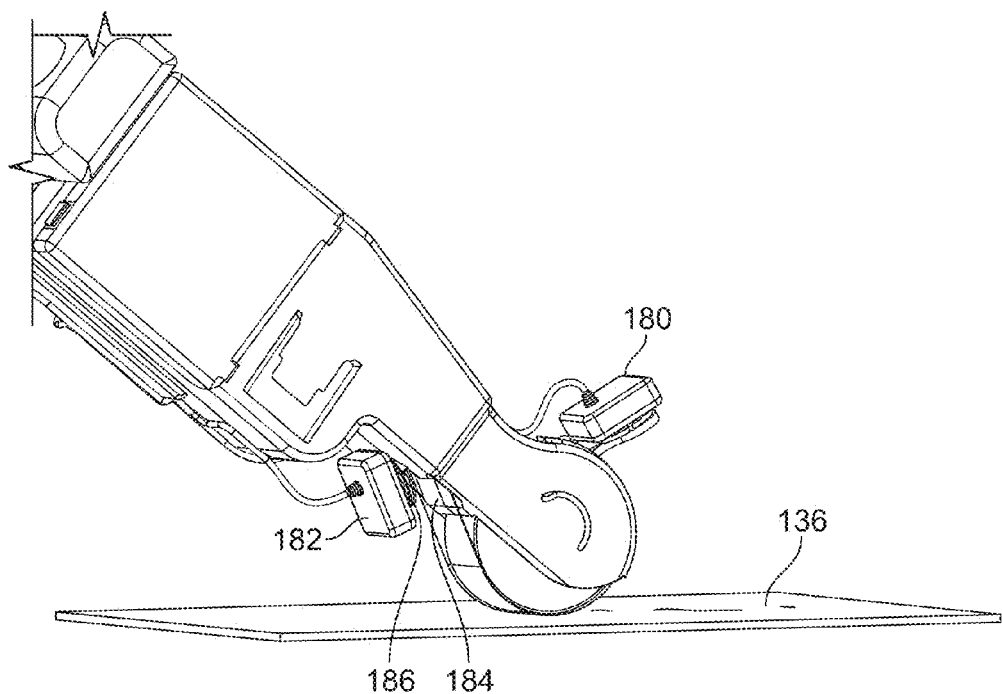

Referring to FIGS. 11A and 11B, TEM collection device 100 includes one camera 180 that is positioned so that it can record close-up, high resolution microscopic videos and/or photographs of surface 136 immediately ahead of TEM pickup roller 130 and may include various forms of forensic lighting, filters or other technologies that can be used to enhance the ability to search for and visualize various aspects of the crimes scene or TEMs. Another camera 182 is positioned so that it can record close-up, high resolution videos and/or photographs of collection tape 134 immediately after the tape diverges from the bottom of TEM pickup roller 130 along with any retained TEMs 132 and may include various forms of forensic foreground, background and side lighting, filters or other technologies that can be used to enhance visualization of the TEMs. This essentially brings the microscopic examination and analytical capabilities to the crime scene (as opposed to waiting for it to be done at a remote trace evidence material laboratory by personnel who were likely not present at the crime scene and therefore lack considerable understanding of the crime scene and other relevant forensic information). If TEM tape and seal laminate 148 is substantially transparent, TEM collection cassette 116 may also include a white background 184 or other desirable colors or feature background immediately behind TEM tape and seal laminate 148 to facilitate the diffusion of the forensic lighting and the imaging and recording of collection tape 134 containing TEMs 132 by camera 182. Alternatively, collection tape 134 itself and/or lower seal 144 may be white or other desirable colors or feature background to facilitate the enhanced imaging and recording of collection tape 134 containing TEMs 132 by camera 182. Camera 182 preferably includes a clear lens cover 186 that can have various uses. For example, lens cover 186 may ensure that camera 182 does not have depressed areas that can collect particulate, may serve as a stand-off so that if any particulate were to fall onto camera 182 it would be in-focus and therefore visible, may serve as a filter, and may have anti-static properties. Although only two cameras are included in this embodiment, it should be understood that the device could include any number and type of cameras or enhanced imaging technologies located at a variety of different positions.

In addition to imaging and recording in the typical human visual light spectrum, the cameras may also include the ability to visualize and record in other electromagnetic spectrums such as UV and IR. These cameras can have visual imaging angles of up to 360 degrees both horizontally and vertically. The device may also incorporate two (stereo) or more video cameras or other visual or other sensor based imaging and distance recording technologies, such as an RGB-D camera that can also record surface edges and/or distance to various objects that could be used to facilitate the generation of 3D video records of the TEM collection process and surrounding area along with allowing the ability to take distance measurements.

Camera 182 may also facilitate microscopic examination of TEMs. In the past, microscopic examination was performed using large heavy microscopes usually used in laboratory settings. However, with camera 182 incorporated into TEM collection device 100, recent advancements in micro camera, micro lens, and micro slides/actuators make it feasible to bring the high power magnification of a laboratory microscope directly to the point of TEM collection, which can greatly shorten the collection to analysis time. 20+ megapixel and 4K (4000 pixels horizontal resolution) cameras with built-in focus and zoom capabilities are now standard in some mobile phones. These cameras typically measure only 1 cm×1 cm×0.5 cm in size. While the device depicted in FIGS. 11A and 11B shows significantly larger, typical off-the-shelf USB cameras, the cameras can be much smaller if desirable. Currently, clip-on and even thin film stick-on mobile phone accessory lenses are allowing regular mobile phones to examine articles at upwards of 400× magnification levels, which enables viewing down to almost that needed to study cell structures.

Extremely high magnification typically comes with a significantly smaller viewing area. This can be addressed by the use of multiple cameras and/or by the use of various technologies that can allow one or more of the camera's smaller viewing areas to view a particular area of interest on collection tape 134. Micro X, Y slide actuator technologies exist such as those that use piezoelectric or other very small actuators. Even small hand-driven mechanical thumb screws could be used. Other technologies such as movable mirrors or tilting the camera could also be used. Off-axis images can be reconstructed to accurately replicate perpendicular viewed images by using various existing image manipulation software technologies. Because both the camera optics and the specimen are on the same platform, there is no problem with steadiness and focus such as when viewing a fixed specimen with a hand-held optic at high magnification.

Also shown are forensic light sources 188 and 190 associated with cameras 180 and 182, respectively. Preferably, one or more of the cameras or other imaging and/or recording technologies utilize various forensic light sources or other electromagnetic emissions used to enhance the observation, collection and photograph/video recording of TEMs including body fluids, hair and fibers, patterned imprints, gunshot residues, drug traces, documents, and the like. These light sources emit light that can contain the ultra-violet, visible and infrared components of light. They can also be used to emit light in one or more color bands that enhance the visualization of evidence by light interaction techniques including fluorescence (evidence glows), absorption (evidence glows or darkens), and oblique lighting (small particle evidence revealed), thereby increasing the amount of evidence uncovered and the quality of the evidence collected and photographed or video recorded. Likewise, one or more of the cameras may employ physical or electronic filters and/or any other type of image and/or data perception enhancing technologies.

Typically, because of limited power and other deficiencies, LED lights are not very effective for forensic lighting techniques. However, because the observation areas of cameras 180 and 182 or other utilized cameras are particularly small and a relatively short distance away, the cameras could be capable of selective spectrum enhancement and/or filtering, and the light sources can utilize small/inexpensive LEDs for forensic lighting image enhancements.

Because TEM collection device 100 has the ability to collect and display on its touch screen a large amount of TEMs and associated data, a reasonable concern might be that this could overload the investigator's ability to search through and make use of all of this information. However, because the videos, photographs and related crime scene data are digital, this potential problem can be easily addressed by the use of various existing, optical color, shape, structure and pattern recognition technologies to help the investigator search through all of the images and data and help him/her to much more quickly associate objects, individuals or locations. This optical recognition technology includes the ability to adjust and fine tune the discrimination thresholds used to optically locate TEMs of interest.

Also, the device could utilize electronic and optical filtering technologies to help locate important TEMs during or after TEM collection and do it at a rate much faster than a human examiner can. The device can also be setup so that once an investigator finds a TEM of interest, it can search through vast amounts of images and data to look for similar TEMs from the current crime scene or even from past and thought to be unrelated crime scenes. Conversely, the recognition technology can also suggest that the investigator review potential TEMs that it has located based on the device's own optical recognition databases or that of existing and widely available trace evidence material reference collections (such as those listed at http://www.nist.gov/oles/forensics/forensic-database-trace-evidence-table.cfm). Over time, the recognition technology could be used to add information to these databases and therefore help them to get larger and more complete at a rate faster than they might otherwise. Artificial intelligence may also be able to play a role in this recognition process.

Figure 12:
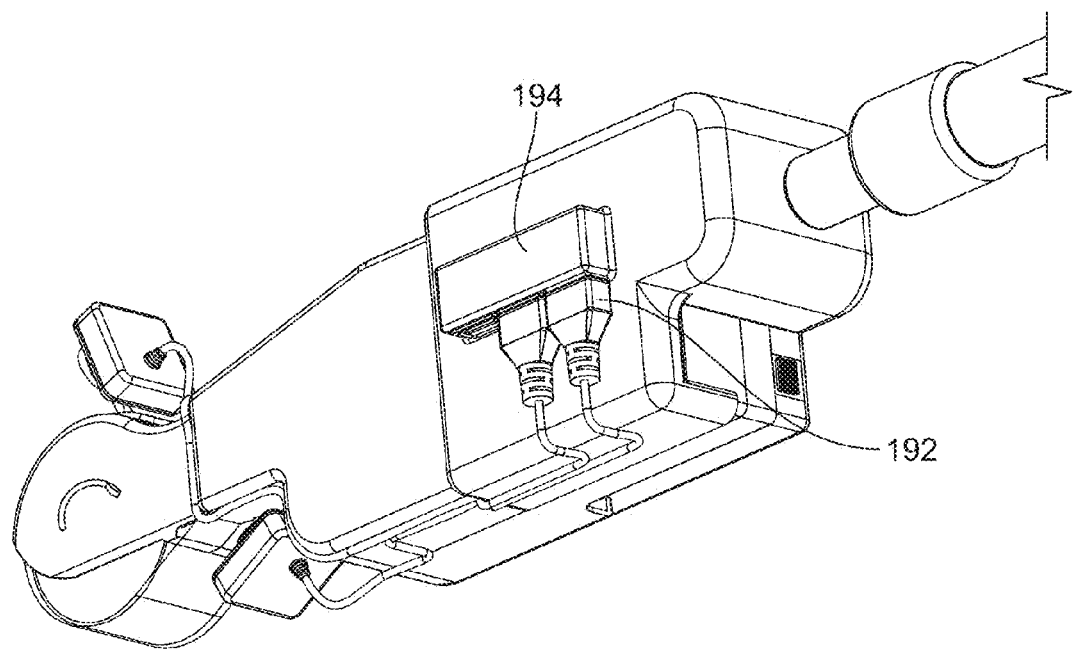
FIG. 12 is a perspective view of the TEM collection cassette showing its USB communications interfaces or other types of electronic communications interfaces to facilitate the use of one or more USB cameras or other types of electronic communications enabled devices.

As shown in FIG. 12, the cameras may utilize a USB or similar communications interface 192 so as to facilitate the easy implementation of different varieties of cameras or other imaging technologies. Also, cassette drive mechanism 104 may have a USB or similar communications interface hub 194 that can be used to facilitate the easy implementation of different varieties of other technologies that may be utilized by TEM collection device 100. In this embodiment, communications interface hub 194 is located on cassette drive mechanism 104. Of course, it should be understood that the communications interface hub could be located elsewhere within the scope of the present invention.

Cameras 180 and 182 combined with forward facing, wide-angle video camera 126 located on the back of touch screen display/CPU 106 can simultaneously record wide angle videos and/or photographs of the potential crime scene, close-up videos and/or photographs of surface 136 and high resolution, high magnification videos and/or photographs of collection tape 134 containing TEMs 132, as described above, which can serve as a very detailed record of the crime scene and TEM collection process and thus facilitate typical trace evidence recovery procedure and recovery documentation requirements. As will be shown in FIGS. 15 and 16, any or all of these images and recordings may be simultaneously viewed on touch screen display/CPU 106.

It can be appreciated that TEM collection device 100 enables investigators or other personnel to microscopically analyze and annotate their observations regarding the collected TEMs. In addition, TEM collection device 100 also provides the forensic laboratory examiners with extensive TEMs and associated crime scene data to facilitate their examinations so as to assist in recapturing the crime scene. As such, the forensic laboratory examiners can be a more significant contributor to the crime scene investigation as a whole. Further, TEM collection device 100 enables quick and easy distribution of any or all of the TEMs and associated crime scene data for remote examination or other informational purposes.

Preferably, TEM collection device 100 also incorporates other data sources and communication capabilities, such as an integrated GPS receiver that can be used to record the precise GPS coordinates of the device when GPS signals are available (such as outdoors and in some buildings). Also, a magnetic compass may be provided that allows the device to reference and record it's orientation relative to "magnetic north" and solid-state multi-axis accelerometers that document the position, angular movements and velocities of the device while in use. These and other types of device position and movement locators can help to provide precision TEM collection movement guidance that may be required when performing the 1:1 collection method on surfaces lacking distinct physical or optical marking, such as when viewing only a bed sheet of a single color. This guidance can be provided to the user through the use of on-screen guidance directions or indicators, guidance lights, laser pointers or projected laser lines and similar technologies. In addition, the positional data could be correlated or otherwise overlaid onto other positional data sources, such as Google Maps or Google Earth, so as to even more fully capture and/or recreate the various elements of the crime scene and surrounding areas. Of course, it should be understood that other technologies could also be incorporated into TEM collection device 100 in accordance with the present invention.

All of the videos, photographs, annotations and position and other information discussed herein may be saved in the internal memory of the touch screen display/CPU 106 and/or on a removable digital memory card or other data recording methods. In addition, TEM collection device 100 may incorporate various communication technologies such as Bluetooth, Wi-Fi and/or 4G cellular, which can allow the device to securely exchange data with other parts of the system, other devices and/or through the Internet or similar secure communication channels.

Internet communication or similar analog and/or digital capabilities allow the data to also be uploaded in real-time from TEM collection device 100 to one or more forensic TEM analyzers, such as forensic TEM analyzer 300 (shown in FIG. 17), or similar systems for immediate or delayed remote examination. Data from multiple TEM collection devices being used at the same time and/or at different locations can also be simultaneously uploaded and compared to each other so as to enable examiners to more quickly determine potential linkages between crime scenes, people and places. Computer driven optical recognition software can help examiners search through all of these images and data and help them to associate items, people and places more quickly than ever before.

Figure 13A:
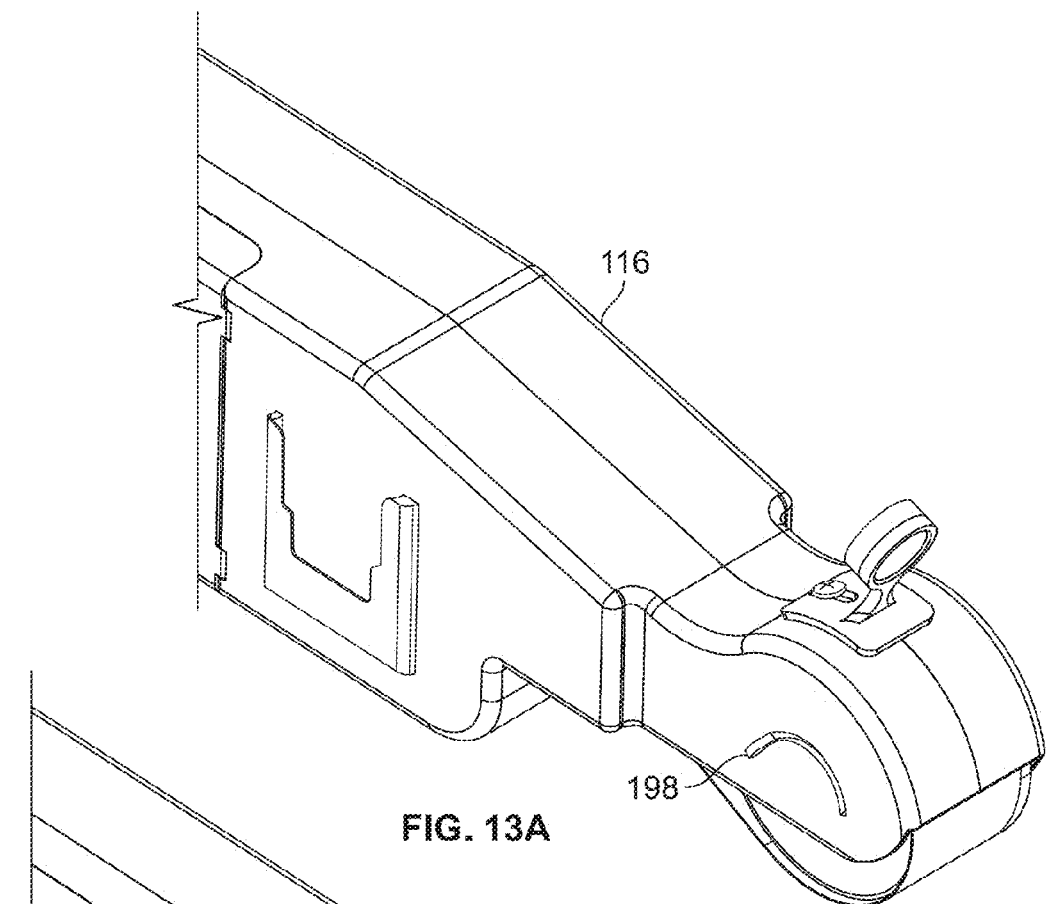
FIGS. 13A and 13b are perspective views of the TEM collection cassette showing its built-in roller cover that can be used to cover the TEM pickup roller and exposed collection tape.
Figure 13B:
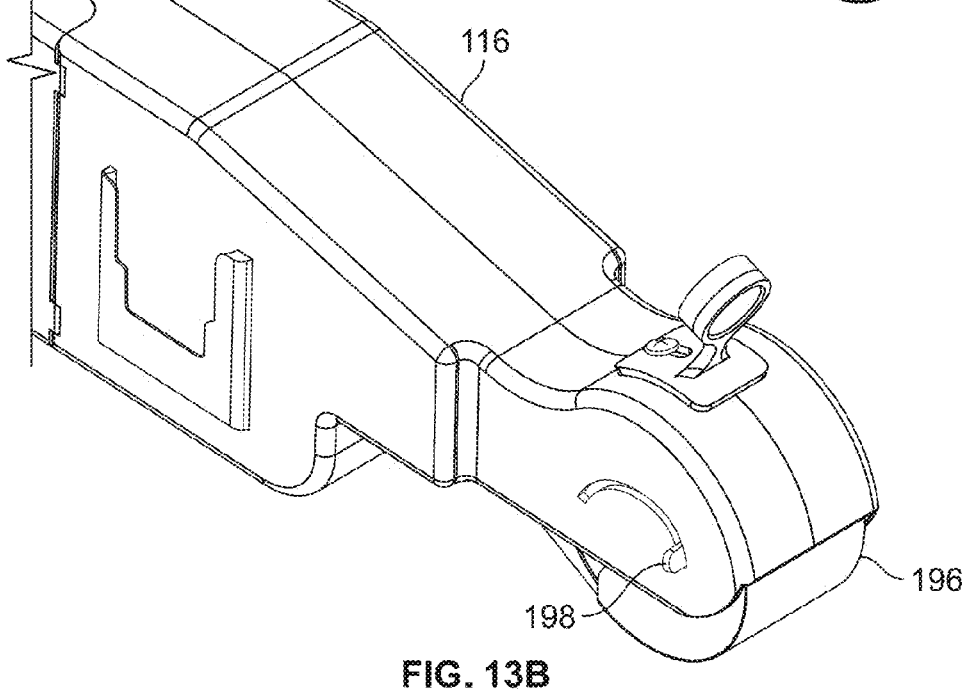

Referring to FIGS. 13A and 13B, TEM collection cassette 116 may have a built-in roller cover 196 that that can be used to cover TEM pickup roller 130 and the exposed collection tape 134 when desirable, such as when moving TEM collection device 100 between TEM recovery attempts, when setting it down, or anytime it is desirable to cover and protect TEM pickup roller 130 and exposed collection tape 134. FIG. 13A shows roller cover 196 in the in-use, retracted position with the cover's built-in roller cover tab 198 in its rearward position. To deploy roller cover 196, the investigator just pushes roller cover tab 198 forward from its rearward position to its forward position, as shown in FIG.

13B, so that TEM pickup roller 130 and the exposed collection tape 134 are covered and therefore protected.

Figure 14A:
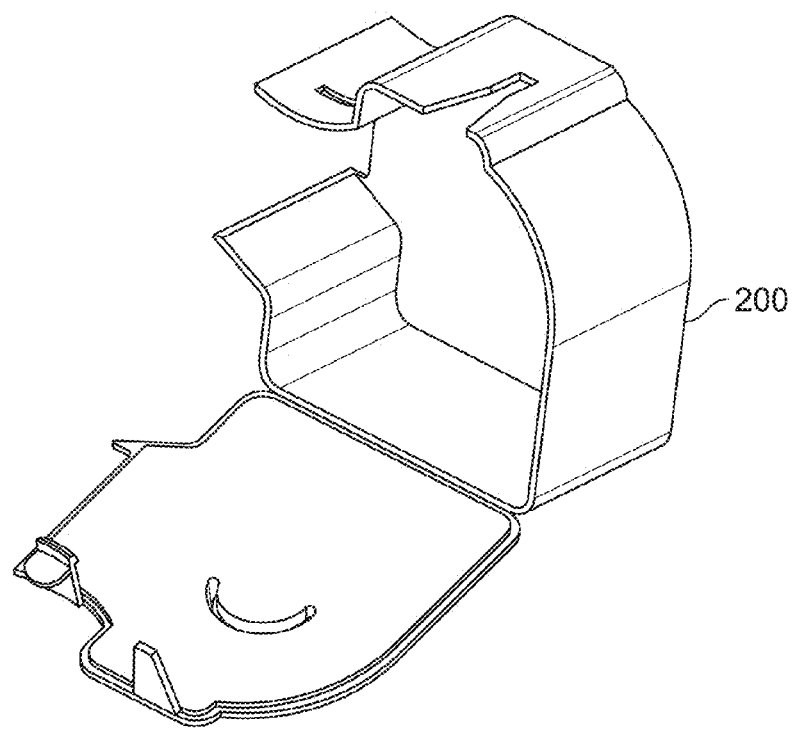
FIGS. 14A and 14B are perspective views of an accessory roller cover for the TEM collection cassette that can be used to cover the TEM pickup roller and exposed collection tape.
Figure 14B:
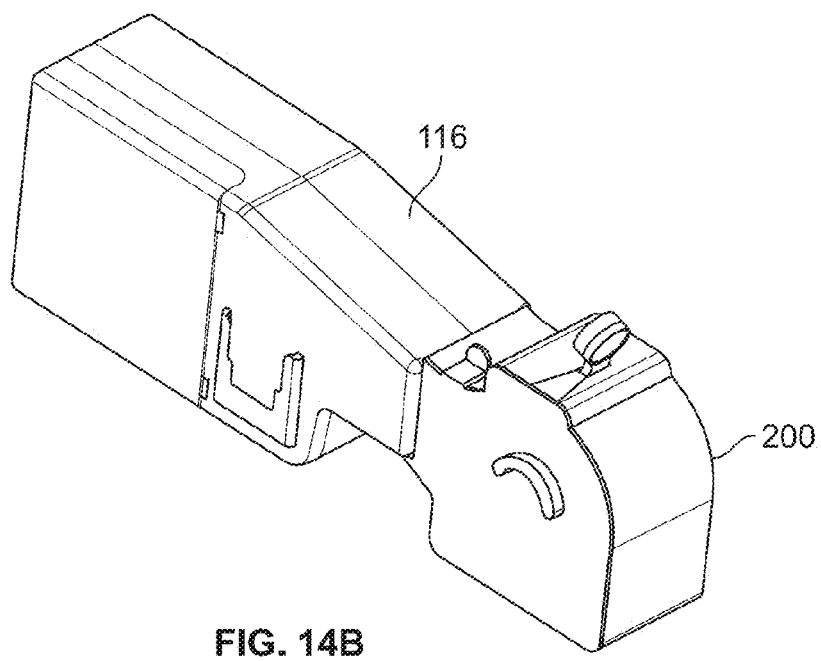

FIG. 14A show an accessory roller cover 200. As shown in FIG. 14B, each TEM collection cassette 116 can optionally come packaged with a sterile accessory roller cover 200 already installed. Roller cover 200 helps to insure that TEM pickup roller 130 and the exposed collection tape 134 are kept clean and secure during the installation of TEM collection cassette 116 into cassette drive mechanism 104, during camera installation, or any time it is desirable to cover TEM pickup roller 130 and the exposed collection tape 134 during use, transportation or storage. Roller cover 200 can also be sealed with a tamper evident seal that can be used to prove contamination prevention.

Figure 15:
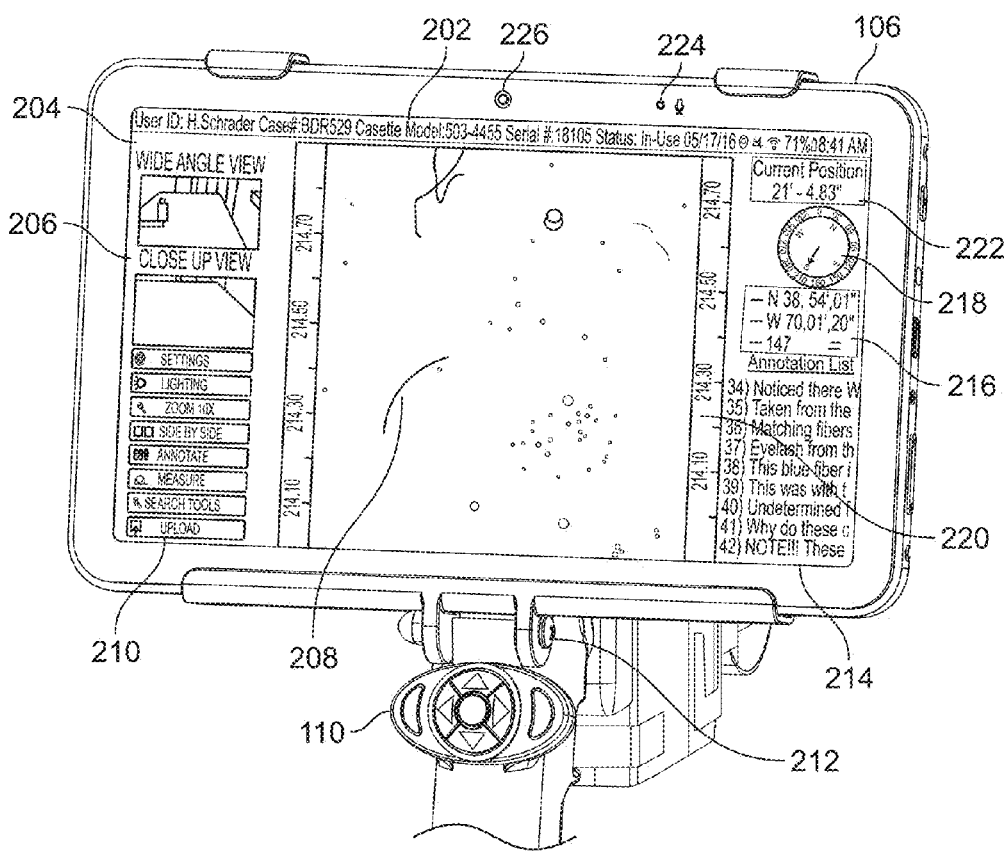
FIG. 15 is a perspective view of a touch screen display of the TEM collection device showing information that may be presented while the TEM collection device is being used to collect TEMs.

FIG. 15 shows touch screen display/CPU 106 with an example screen shot of a user interface that an investigator may see while using TEM collection device 100 to collect TEMs. It should be noted that the screen shots described herein are merely examples of the basic intended usage of touch screen display/CPU 106 and do not limit the scope of the present invention.

Shown at the top of the screen shot shown in FIG. 15 is a status bar 202 that contains information such as the user ID, case number, model number of the TEM collection cassette, serial number of the TEM collection cassette, system status, date, location status, speaker status, Wi-Fi status, battery level and time of day. The view of video camera 126 is depicted as a wide angle view 204. Depending on the camera lens used and the angular adjustment of touch screen display/CPU 106, all or part of TEM collection cassette 116 may be visible in this view which would be desirable for TEM recovery procedure documentation. This view can also be resized by the expand touchscreen button in the lower right corner. The view of camera 180 is depicted as a close up view 206. This view is adjustable depending on the camera lens used and the angular adjustment of the camera's mount on the TEM collection cassette, and this view is also desirable for TEM recovery procedure documentation. This view can also be resized by the expand touchscreen button in the lower right corner.

Screen item 208 is an example of a piece of TEM, in this case an eyelash, that was captured by collection tape 134 and presented to camera 182 and then immediately displayed in high resolution, high magnification on touch screen display/CPU 106. Also depicted on the screen are various hairs, fibers and very small drops of blood that may otherwise not be visible at the time of collection. The ability to capture and analyze TEMs quickly not only speeds up the time from TEM collection to analysis, but also helps the investigator determine and adjust subsequent search areas.

Menu buttons 210 depict various system features, such as settings, lighting, zoom 10x, side by side, annotate, measure, search tools and upload, which can be easily accessed and whose use is readily understood. It can be appreciated that the screen touch input can be by the use of tablet stylus 125 (shown in FIG. 5), the user's finger, or an on-screen keyboard display. Thumb controls 110 allow navigation and selection of various features even while TEM collection device 100 is being held in the same hand. Touch screen swivel 212 allows the angle of touch screen display/CPU 106 to be adjusted to best facilitate viewing and manipulation when the device is being used at different angles and levels. It also allows touch screen display/CPU 106 to be lowered to the horizontal position to facilitate transportation and storage.

The investigator can make on-screen drawn, typed or voice annotations at any time during TEM collection or even after TEM collection, such as when reviewing videos of the contents of collection tape 134 and/or of the crime scene. After making an annotation, the investigator hits the "Save" button and each annotation is automatically numbered, time stamped and associated with that point of the applicable video. If desired, the investigator can also select various user inputs such as TEM type, TEM importance, needs review, etc. from a drop down list, which will also be automatically associated with that annotation and that point of the applicable video. The number and the first part of each annotation is then displayed on the scrolling annotations list 214 along with a small microphone icon indicating if that particular annotation also has voice or other audible annotation attached. In addition, each annotation can be of a different color, for example to group various types of referenced TEMs or to indicate the importance of the annotation. At any time, the investigator can select a saved annotation from the list and his/her text and/or drawn notes will be displayed on the touchscreen precisely where they were when the annotation was made. The text and notes can be added to or edited at any time, but each version will preferably be saved in its entirety each time the investigator hits the "Save" button. If the selected annotation includes a voice or other audible annotation, an icon button depicting a microphone will be placed on the screen to facilitate easy access to the audible annotation. Screen section 216 depicts the GPS coordinates (if a GPS signal is available) along with the location elevation and GPS signal strength. Screen section 218 depicts the current compass reading. The system also keeps an ongoing digital record of these coordinates, compass readings and associated data.

To the left of annotation list 214 is a vertical TEM tape linear reference bar 220 that depicts the overall length of a given collection tape and can include small marks on the bar that indicate where on the tape annotations were made along with providing a visual depiction of the current position of the tape in relation to its start and end points. These marks can be color or otherwise coordinated with the colors of various annotations or for other reasons desirable by the investigator. This bar can also be used to depict other linear tape position references. To the right of the bar is a small arrow that visually depicts the current physical position of the tape relative to its starting and end points.

Screen section 222 is a visual readout of the current physical position of the TEM cassette tape, or if in visual rewind mode it will show the current location of the tape image on the screen. Touch screen display/CPU 106 includes a microphone 224 and a rear facing camera 226, although these components could be positioned in other locations.

Figure 16A:
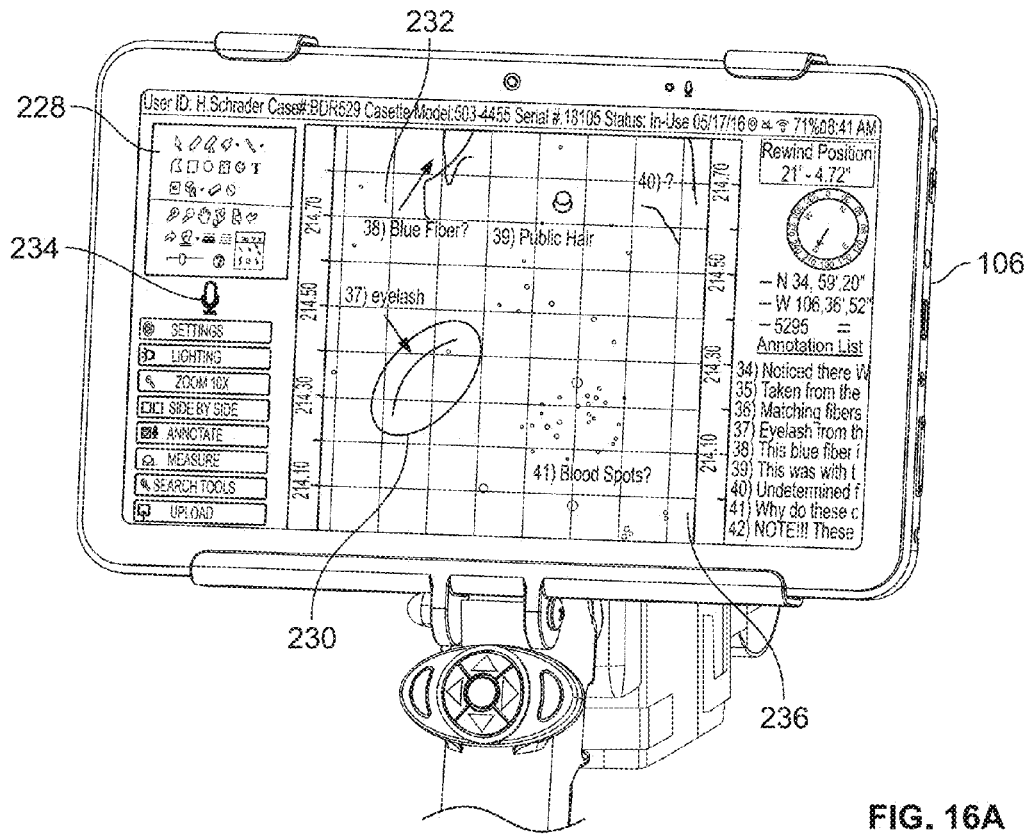
FIG. 16A is a perspective view of a touch screen display of the TEM collection device showing information that may be presented when a user makes drawn, typed or voice annotations.
Figure 16B:
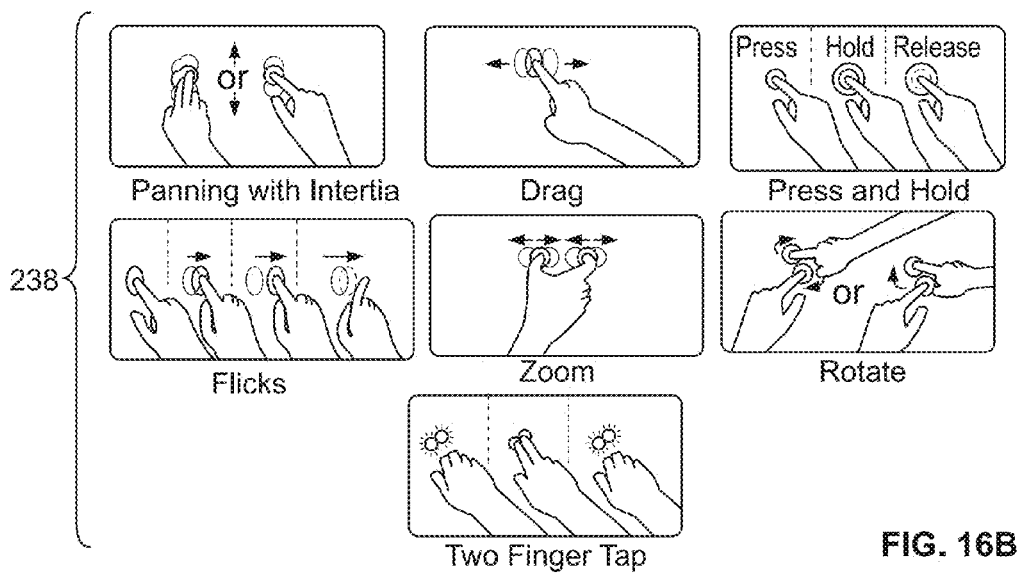
FIG. 16B are diagrams that show examples of common touch screen finger gesture inputs that can be used to easily manipulate the on-screen TEM images and provide various other inputs.

FIG. 16A shows touch screen display/CPU 106 with an example of a screen shot that would be typical of what an investigator might see while making drawn, typed or voice annotations. Shown are the annotation tools 228, examples of on-screen annotations 230 and 232, a voice annotation icon 234 used to start voice or other audible annotations, and a position grid 236 that divides the linear tape screen into x and y axis measurements to facilitate the precise location and record of recovered TEMs. FIG. 16B shows examples of common touch screen finger gesture inputs 238 that can be used to easily and quickly manipulate the on-screen images and provide other various inputs to touch screen display/CPU 106.

One skilled in the art will appreciate how the present invention is a substantial improvement in both speed, detail and accuracy over traditional TEM recovery and record keeping methods required by most agencies involved in TEM recovery.

While the ability to quickly and easily collect vast amounts of TEMs is very important, equally important is the ability to quickly and efficiently analyze the collected TEMs using a forensic TEM analyzer, such as forensic TEM analyzer 300 shown in FIG. 17. In this embodiment, forensic TEM analyzer 300 includes a very high magnification microscope 302 that can be used to microscopically analyze, annotate, segregate and create digital backups and much higher resolution/magnification digital records of the collected TEMs and associated crime scene data, which can then be easily electronically distributed for additional review over its digital data connection. Forensic TEM analyzer 300 also includes a large high definition touch screen 304. While microscopically viewing the collected TEMs through microscope 302 and/or touch screen 304, all of the video, audio, positional and other TEM recovery data that was generated at the crime scene is presented to the examiner in exact timed correlation to the linear position of TEMs on the collection tape as they were being collected. This serves to provide the forensic laboratory examiners with extensive TEMs, crime scene and other related data to facilitate their examinations so as to assist in recapturing the crime scene. As such, the forensic laboratory examiners can be a significant contributor to the crime scene investigation as a whole. Further, TEM collection device 100 enables quick and easy distribution of any or all of the TEMs and crime scene related data for remote examination or other informational purposes. Any or all of this information could also be cast to larger video screens to facilitate the simultaneous examination of trace evidence materials by many users if desired. The system's ability to store large amounts of both physical TEMs and high-resolution digital images and data for long periods of time can also be crucial later on as additional information relative to important TEMs is acquired, even after the case has been put on hold or even closed.

The forensic TEM analyzer can be offered in many configurations and options. It can be as simple as a hand driven reel system viewed under a microscope connected to a laptop computer for viewing of the collected TEMs and recorded data, or much more elaborate such as forensic TEM analyzer 300 of this embodiment. The ability to select different options helps to make the system cost effective for almost any size forensic crime scene investigation department.

Forensic TEM analyzer 300 may include a HEPA filtered, positive pressure, clean work area 306 directly under microscope 302. Located inside clean work area 306 is a reel system 322. Reel system 322 is configured so that the entire take-up reel 152 (shown in FIG. 8) or just segmented samples of TEM tape and seal laminate 148 can be loaded into clean work area 306 for microscopic and crime scene data examination. Reel system 322 also has the ability to seal, cut and remove selected areas of TEM tape and seal laminate 148 or automatically remove the side seals from selected areas of the tape to allow physical access and removal of selected TEMs.

FIG. 17 shows the high definition touch screen 304 with an example screen shot of a user interface that a user may see while using forensic TEM analyzer 300. It should be noted that the screen shots described herein are merely examples of the basic intended usage of touch screen 304 and do not limit the scope of the present invention. The screen shot shown in FIG. 17 includes a very high magnification TEM view 308, a wide angle video 310, a close-up video 312, a video frame by frame viewer 314, the analyzer's GPS coordinates 316, a 3D room reconstruction 318, and an audio view 320.

Forensic TEM analyzer 300 also includes both foreground lighting 324 and background lighting 326. These forensic light sources are used to enhance the location, observation and photograph/video recording of TEMs including latent fingerprints, body fluids, hair and fibers, patterned imprints, gunshot residues, drug traces, questioned documents, and the like. These light sources emit light that can contain the ultra-violet, visible and infrared components of light. They can also be used to emit light in one or more color bands that enhance the visualization of evidence by light interaction techniques including fluorescence (evidence glows), absorption (evidence glows or darkens), and oblique lighting (small particle evidence revealed) and other technologies such as darkfield, phase contrast, polarization, and spectrometry, thus increasing the amount of evidence uncovered and the quality of the evidence collected and photographed or video recorded. Likewise, one or more of the cameras may employ filters and/or any other type of image and/or data perception enhancing technologies.

Forensic TEM analyzer 300 also incorporates various computerized electronic filters that can be used to find, view and analyze TEMs. These filters can be used to adjust image brightness, contrast, color correction, color isolation, and the like to increase the examiner's ability to identify crucial TEMs.

Because forensic TEM analyzer 300 has the ability to collect and display a large amount of TEMs and associated data; a reasonable concern might be that this could overload the examiner's ability to search through and make use of all of this information. However, because so much of the data generated by forensic TEM analyzer 300 is digital, this potential problem can be easily addressed by the use of various existing, optical color, shape and pattern recognition technologies.

As the images and other data comes in from one or more TEM collection devices 100 or is generated by forensic TEM analyzer 300, optical recognition technologies can help the examiner search through all of the images and data to help him/her more quickly associate objects, individuals or locations.

Also, the system could utilize different lighting and filtering technologies to help locate important TEMs and do it at a rate much faster than a human examiner can. The system can also be setup so that once an examiner finds a TEM of interest, it can sift through vast amounts of images and data to look for similar TEMs from the current crime scene or even from past and thought to be unrelated crime scenes. Conversely, the recognition technology can also suggest that the examiner review potential TEMs that it has located based on the analyzer's own optical recognition databases or that of existing and widely available trace evidence material reference collections (such as those listed at http://www.nist-.gov/oles/forensics/forensic-database-trace-evidence-table.cfm). Over time, the recognition technology could be used to add information to these databases and therefore help them to get larger and more complete at a rate faster than they might otherwise. Artificial intelligence may also be able to play a role in this recognition process. Over time, as the recognition technology and its databases grow, at some point forensic TEM analyzer 300 might start "connecting the dots" between TEMs and the people associated with them and help to solve past, thought to be unrelated, crimes because of its ever growing search abilities and databases.

As discussed above, TEM pickup roller 130 and collection tape 134 of TEM collection device 100 can be adequately protected from potential contamination by using built-in roller cover 196 (shown in FIGS. 13A and 13B) and roller cover 200 (shown in FIGS. 14A and 14B). The entire TEM collection device 100 can be kept safe and secure using conventional storage methods. However, referring to FIG. 18, a portable security holder 328 is preferably provided that offers a significant advancement in TEM cassette contamination protection, security, chain of custody adherence and over-all ease of use.

Figure 18:
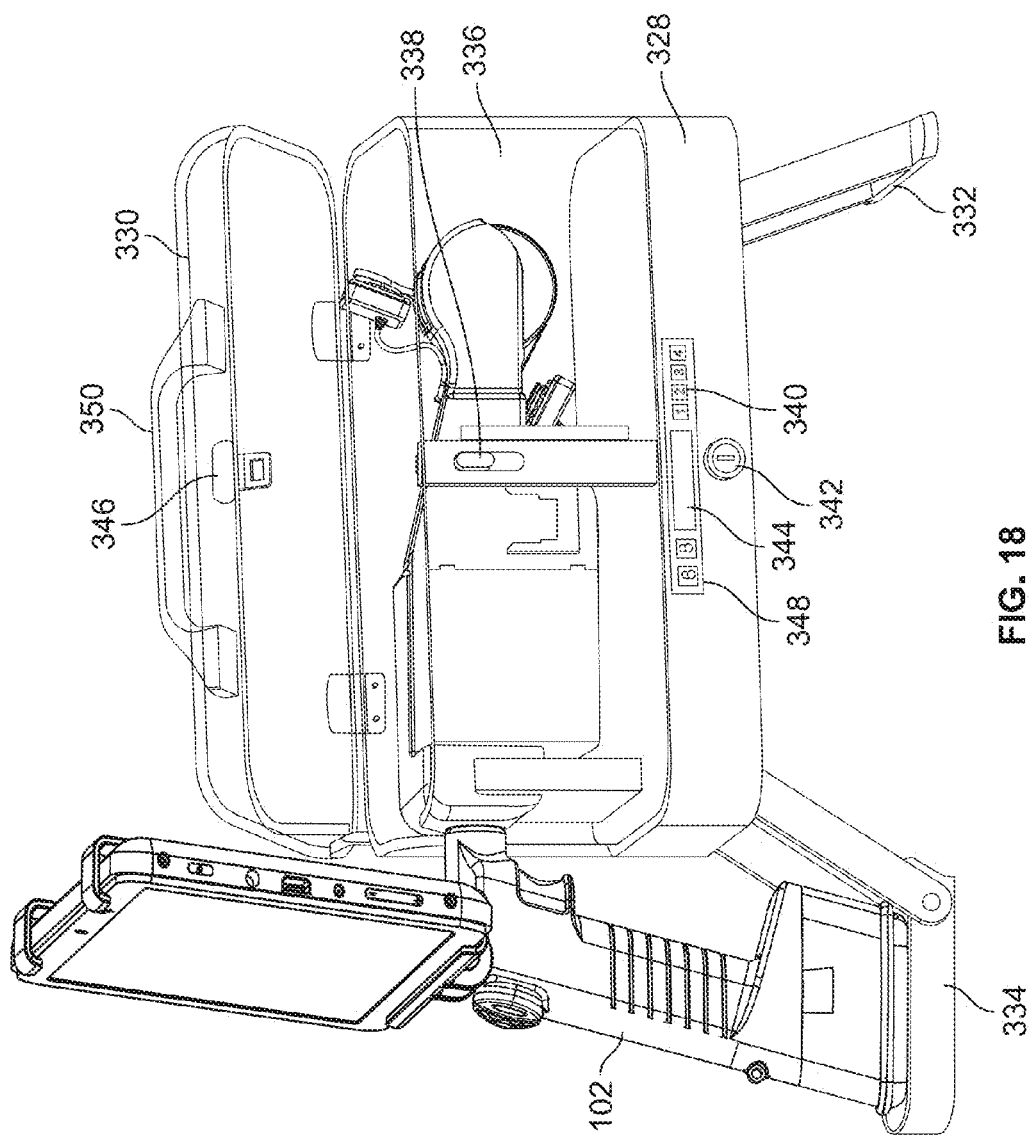
FIG. 18 is a perspective view of a portable security holder for the TEM collection device showing the holder lid in the open position.

FIG. 18 shows security holder 328 with its holder lid 330 open. For added convenience, security holder 328 also provides support for handle assembly 102 and touch screen display/CPU 106 while also allowing full access to the touchscreen and all of its videos and data contained therein. Security holder 328 is configured for maximum flexibility and ease of cleaning and includes fold-up support legs 332 and a fold-up handle holder 334 so that security holder 328 can be used to safely house TEM collection cassette 116 (with or without the optional handle shaft 118 installed) and optionally cassette drive mechanism 104.

As shown in FIG. 18, security holder 328 includes a holder enclosure area 336, a holder latch 338 used to lock holder lid 330 in the closed position, a key pad 340 that can be used to unlock the holder if a PIN code has been generated to allow the holder to be unlocked using the PIN code, a key slot 342 that allows a mechanical key to unlock the holder, a holder display 344, a lid lock tab 346, holder lock/unlock buttons 348, and a carrying handle 350.

This small/portable security holder 328 and its holder enclosure 336 provide a very convenient, clean and lockable place to set down TEM collection device 100 anytime while in-use or for secure transportation and storage. It also includes integrated touch screen display/CPU 106 enabled wireless Bluetooth or similar communication protocol locking and event recording capabilities that make adherence to TEM collection documentation, contamination, preservation, security and chain of custody procedures extremely quick and easy.

With TEM collection cassette 116 and other components securely locked in place, handle assembly 102 can be removed and the user can still use touch screen display/CPU 106 to do things such as review the videos and other TEM collection process data, make annotations, and upload or email any or all of the collected digital data to one or more forensic TEM analyzers or to any other desired location.

Figure 19:
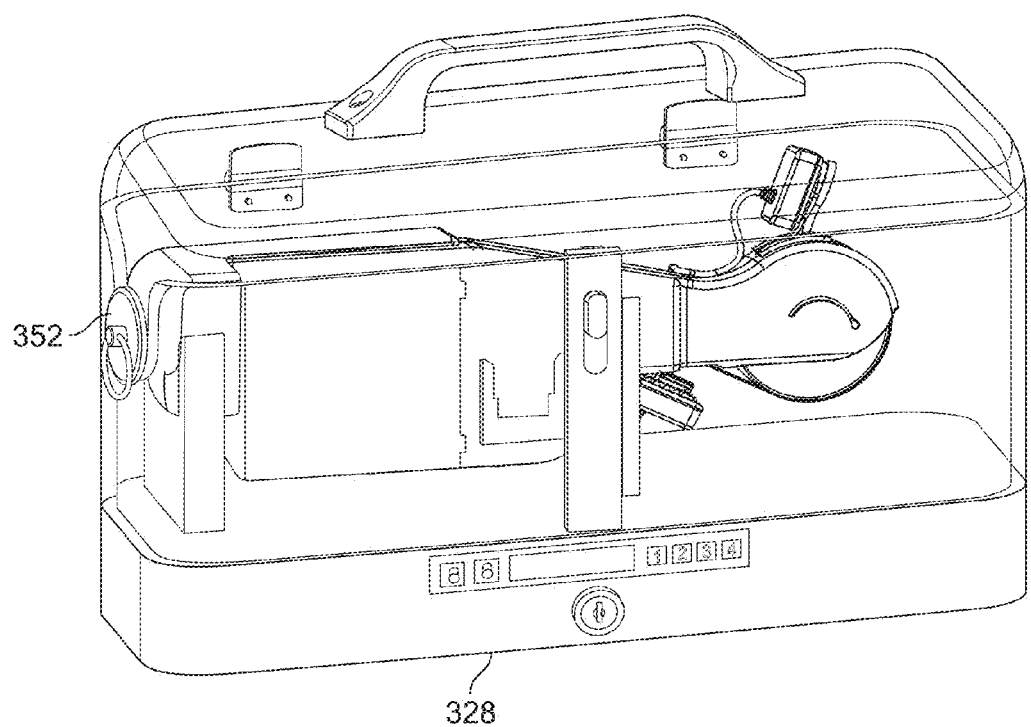
FIG. 19 is a perspective view of the portable security holder with the holder lid closed and with only the TEM collection cassette securely locked inside with a seal plug installed to block off the unused holder shaft hole.

FIG. 19 shows portable security holder 328 in the closed position with handle assembly 102 removed and cassette drive mechanism 104 and TEM collection cassette 116 securely locked inside. A seal plug 352 can be installed to block off the holder shaft hole and this seal plug can also be secured with a tamper evident seal if desired.

Figure 20A:
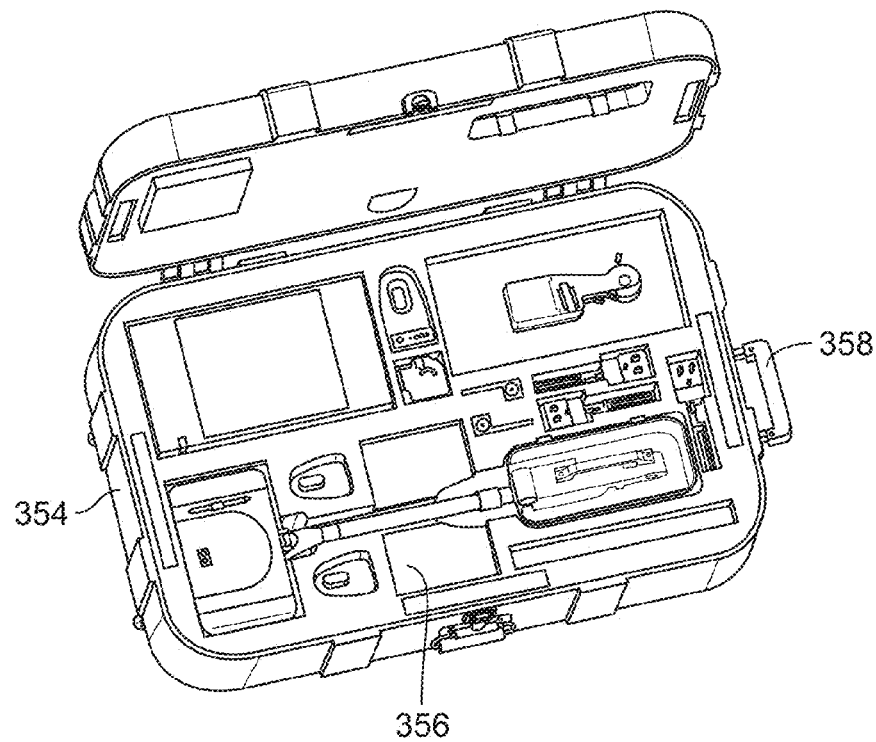
FIGS. 20A and 20B are perspective views of a carrying case that allows the TEM collection device and many of its accessory components to be transported in a secure, lockable and wheeled case.
Figure 20B:
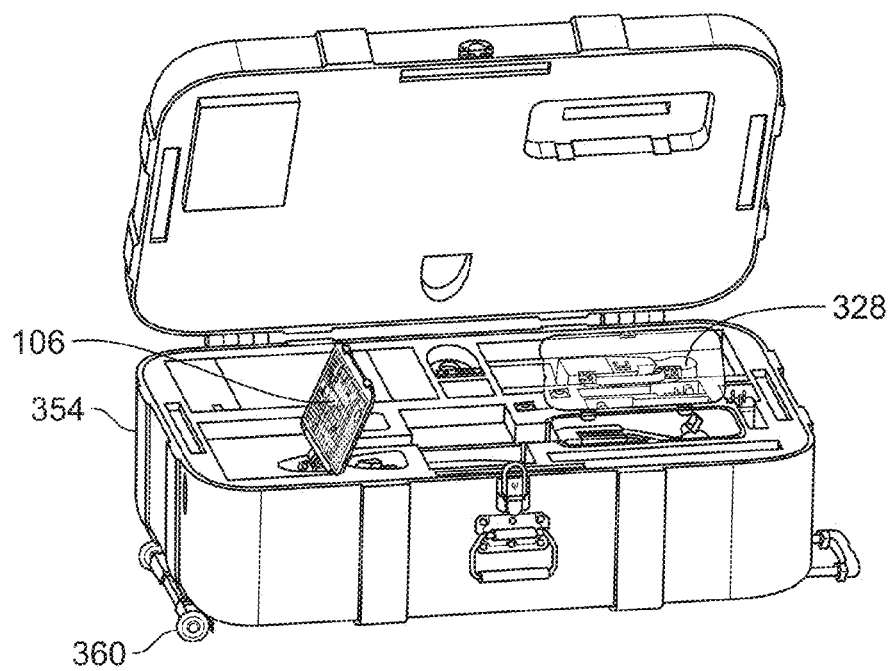

FIGS. 20A and 20B shows a carrying case 354 that allows for TEM collection device 100 and many of its available components to be transported in a secure, lockable, wheeled carrying case. It is very important to allow an investigator to get to TEM recovery locations and be setup and ready to work quickly. Carrying case 354 is configured for maximum flexibility and organizational efficiency. For example, TEM collection device 100 can be quickly placed into case 354 regardless of whether or not the optional extension shaft 118 is installed due to the inclusion of alternate handle assembly area 356. Touch screen display/CPU 106 can be tilted up and used and security holder 328 accessed, opened or closed even while placed in the case, as shown in FIG. 20b. These features help to facilitate the quick pack-up and movement from crime scene to crime scene, which can be important during fast-moving investigations. Carrying case 354 also has compartments for a four piece carton of new, sterile cassettes, four used cassettes, two extra rechargeable handle batteries and charger, cameras, power supply/chargers for the handle, tablet and security holder, a TEM roller cover and more. To enable fast transport, carrying case 354 includes a handle 358 and wheels 360.

Figure 21A:
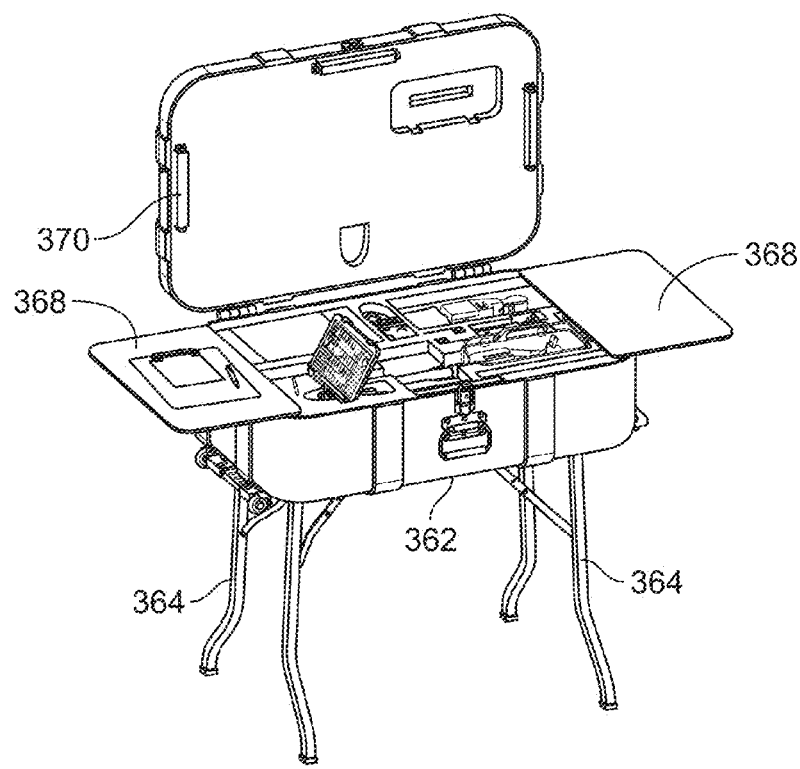
FIGS. 21A, 21B and 21C are perspective views of a carrying case with fold-up legs, fold-up work surfaces and lighting that allows it to function as a portable TEM collection workstation.
Figure 21B:
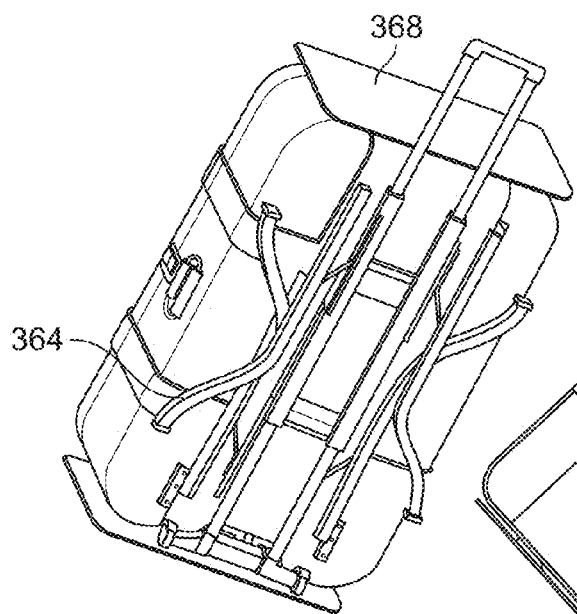
Figure 21C:
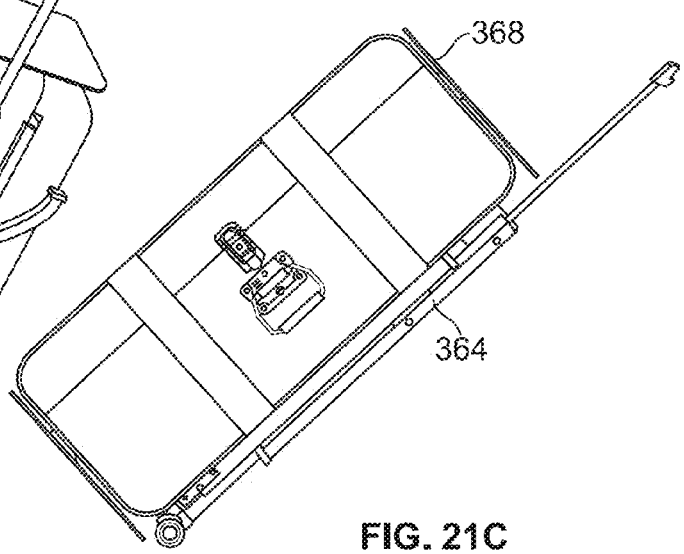

At many crime scenes, access to a clean work area is uncertain at best. FIG. 21A shows a portable workstation 362 with sturdy fold-up legs 364 that position carrying case 366 at a preferred working height regardless of what is available at the crime scene. Also, two large fold-up ridged edge work surfaces 368 provide room for assembly/disassembly of TEM collection device 100, writing and more. Three light strips 370 with adjustable brightness and rotation assure there will be plenty of light to work. Therefore, workstation 362 can go from in-use to locked and ready to go to the next location very quickly, as shown in FIGS. 21B and 21C.

Figure 22A:
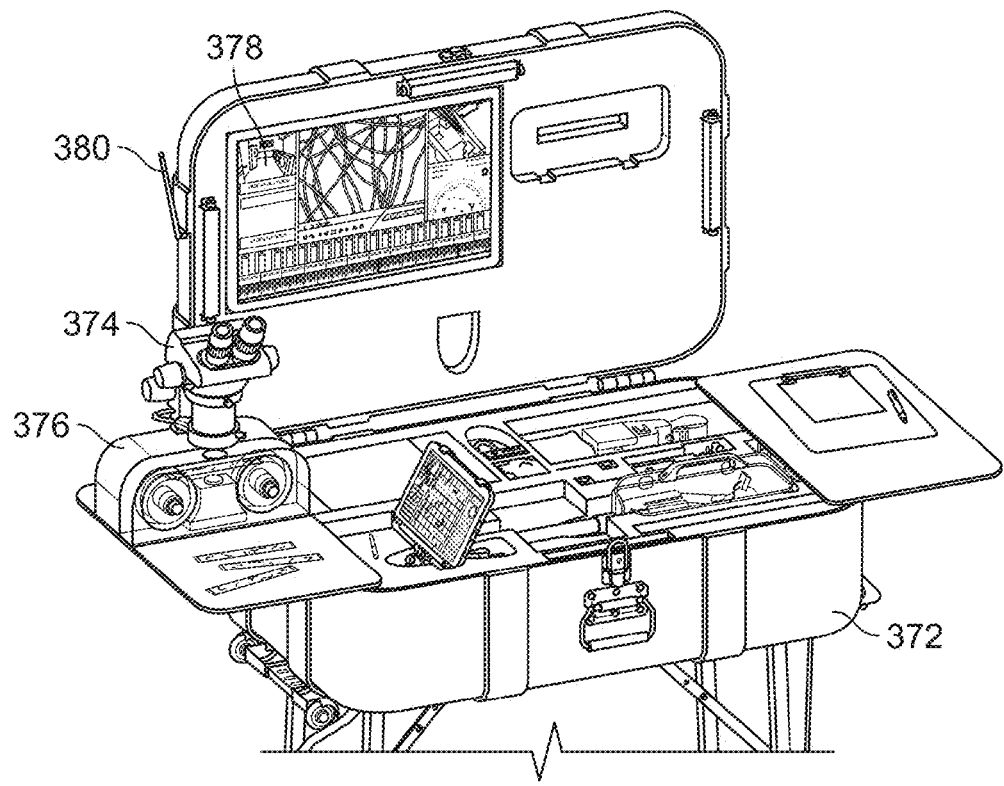
FIGS. 22A and 22B are perspective views of a portable forensic workstation that may be used to analyze the TEMs collected by the TEM collection device at or very near the crime scene or any other desired location.
Figure 22B:
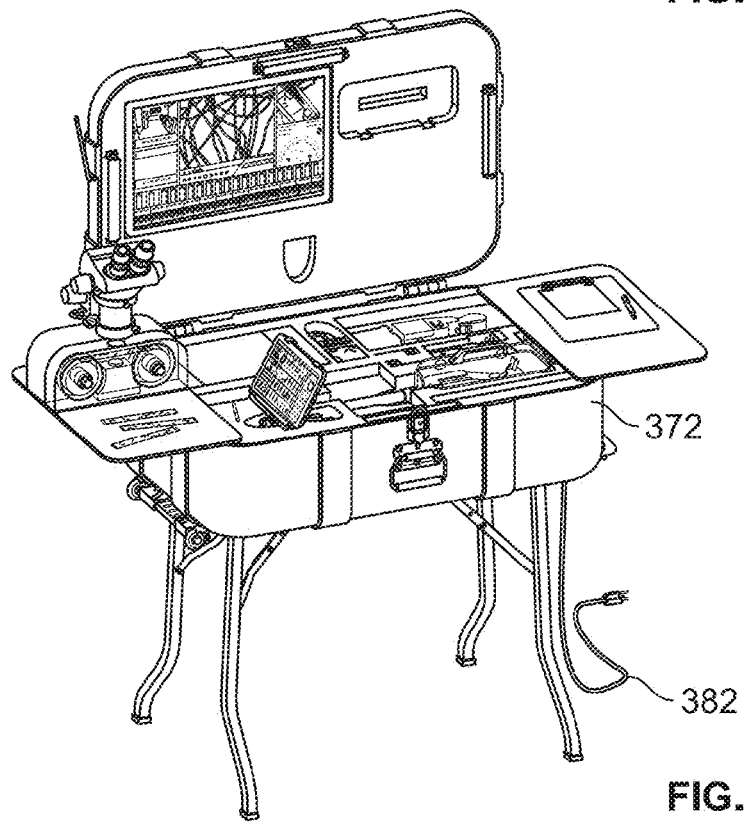

FIGS. 22A and 22B show a portable forensic workstation 372 that is configured to further shorten the time and information gap between TEM collection, analysis and distribution by giving investigators everything needed to perform a very thorough analysis of the collected TEMs gathered by TEM collection device 100 at or very near the crime scene. It can be used with a standard high magnification microscope 374 or a more compact forensic TEM analyzer 376. With its rugged, built-in solid-state computer (not shown), touch screen monitor 378 and high-speed data connection 380, compact analyzer 376 very quickly brings all the capabilities of the laboratory version to wherever it's needed, be it at the next crime scene site or across the country.

Workstation 372 also includes a retractable 110 volt AC or similar power source cord 382 that not only powers the entire forensic system, but also powers multiple, built-in battery charging ports located in the bottom of the various storage areas. When plugged in, the rechargeable batteries in handle assembly 102, security holder 328, touch screen display/CPU 106 and those placed in the included handle battery charger are all kept up to charge simply by placing them in their respective storage areas helping to assure all parts of the system are at fully charged power levels when needed. In addition, workstation 372 can be configured to include its own built-in, rechargeable, high-capacity battery (not-shown) so that the system can be used for lengths of time even when an external power source is not available at the workstation's location.

Because TEM collection device 100 is constantly generating videos of the crime scene with multiple cameras during TEM collection along with generating other types of positional data, the system is capable of generating three dimensional (3D) recreations of the crime scene, its interior objects and/or a 2D floor plan using one or more of the device's imaging or location sensors along with various computational methods well known to one skilled in the art.

Figure 23:
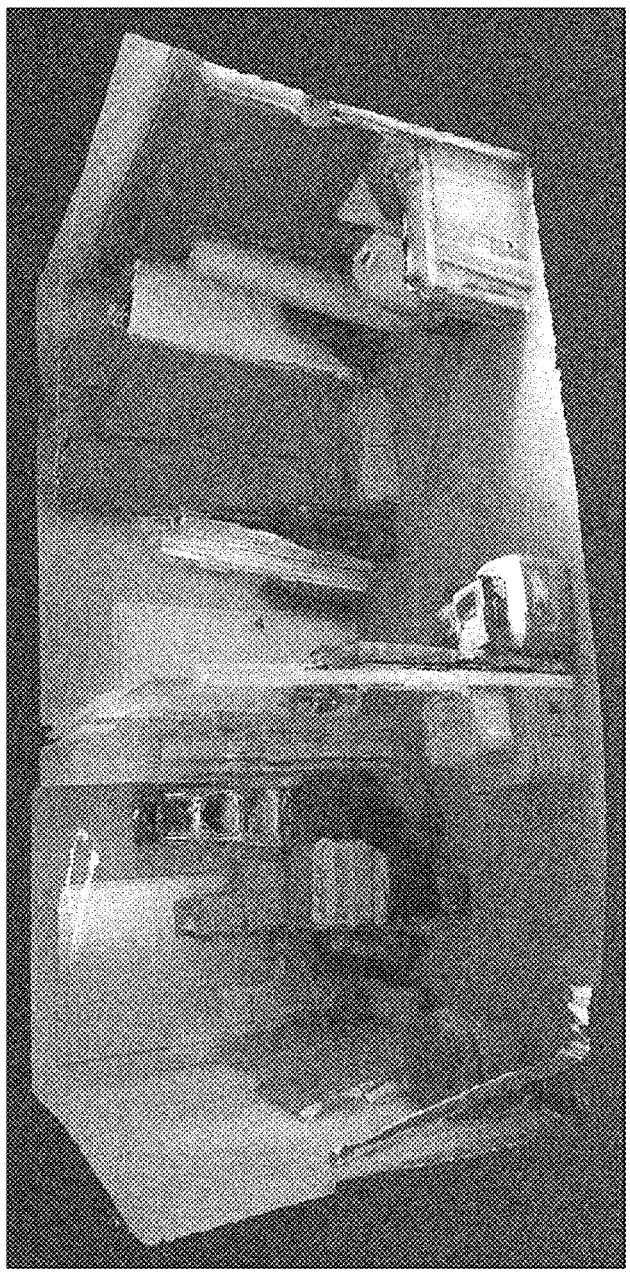
FIG. 23 is an example of a 3D room reconstruction performed using a single camera.

FIG. 23 shows an example of a 3D room reconstruction that was created using only a single camera and solid-state accelerometers that measured the movement of the camera as it was moved about the crime scene. These types of 3D reconstructions can be performed on touch screen display/CPU 106, forensic TEM analyzer 300 or uploaded to any other computer or computational device within the scope of the present invention.

3D reconstructions of the crime scene will give investigators the ability to not only precisely link the collection of TEMs to their 2D videos and locations, but also to 3D recreations of the crime scene during the collection of TEMs. This will not only help the investigators with their investigations, but can also be very useful in visually detailing important aspects of the forensic crime scene investigation to people who were not present during the investigation, such as other crime scene investigators or even a judge, jury, or expert witness during trial. This technology would allow investigators to view and virtually walk through, turn, pan and zoom in on photorealistic 3D recreations of investigation crime scenes and objects contained therein as if they were physically present at the scene during the collection of the TEMs. This technology will not only help to save time, money and other resources during crime scene investigations, but will also be useful for its ability to easily and efficiently detail important aspects of crime scene investigations to other investigators, judges and juries, which will also help to save time, money and other resources during trial proceedings.

The system could also include one or more secure smart phone and tablet applications that could be used to share photographs, videos and data for review and to enable the entry of comments and annotations. It could also be used to quickly alert one or more users, such as a police department or personnel, to be on the lookout for specific TEMs or TEM-related people or objects found by the TEM collection devices to further help to shorten the time and information gap.

In view of the above, one skilled in the art will appreciate how these mobility features can significantly reduce TEM collection and analysis time. This time reduction can greatly improve the ability of investigators to much more quickly utilize all of the information that can be gained from the TEMs and other crime scene data and therefore increase the speed and ability of crime scene investigators to use TEMs to solve crimes.

It is also very easy to see how the system allows investigators to focus more of their effort on the TEM collection and analysis process and less on generating the required TEM location, security, chain of custody and other required procedural documentation. Described below are examples of many additional integrated hardware and software procedural technologies that can be utilized to facilitate an even greater increase in the ease, speed and quality of the required TEM recovery procedural and record keeping compliance requirements.

The system can include an open-architecture TEM procedural protocol system to make compliance with departmental and government trace evidence recovery procedures quick and easy. The following are examples of how the system can be configured to help manage and document procedural compliance from a cassette's first use all the way through to long term storage. For maximum forensic organization flexibility, most of these compliance procedures are fully customizable so that its trace evidence recovery procedures can be easily customized to meet the needs and requirements of different agencies, departments and their particular TEM recovery protocols.

Similar to most computer systems, the operation of the system is be managed by assigning various user levels such as "User Class 1," "Administrator," and the like with corresponding functional and adjustment abilities. Typical trace evidence recovery procedures are built into the system and will serve many organizations with little or no modification needed. Many functions can be easily turned on or off by a simple check box. The procedural text wording can be easily altered so that specific department or personnel names can be added or edited and drop-down lists can be used to allow a given set of user inputs or choices. In addition, a hierarchal procedures list can be edited to add or delete process steps and it can implement rules-based steps based on the different user inputs or situations. All of these process changes are automatically recorded and date stamped in the process modifications log to help maintain procedural change integrity. There are also provisions for the system to be configured to exchange data and work along with existing forensic crime scene, laboratory and evidence tracking systems.

This procedural compliance assurance starts as soon as TEM collection device 100 is turned on and continues throughout the use, analysis and final disposition/storage of a sterile single-use cassette and its contents. An example will now be described.

Figure 24:
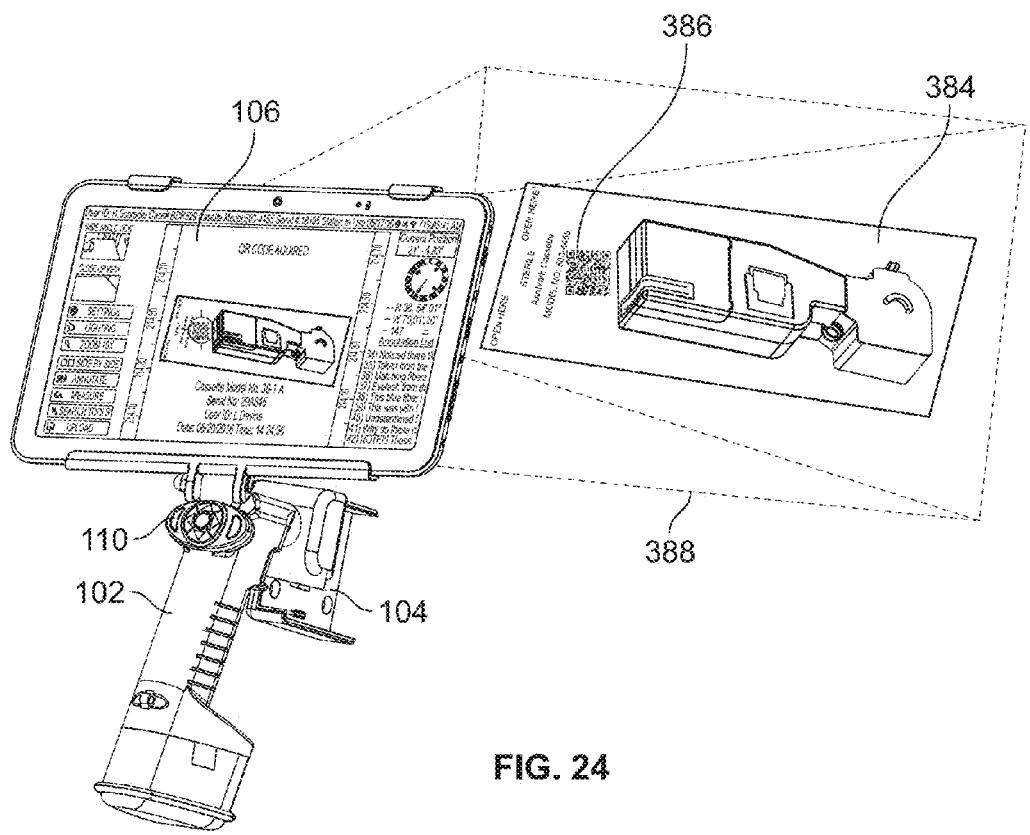
FIG. 24 is a perspective view of the TEM collection device in which the TEM collection cassette is provided in a peel pouch having a QR or similar identifying code.

With reference to FIG. 24, upon start-up, TEM collection device 100 performs an internal system check, which includes making sure that a single-use cassette is not already loaded into cassette drive mechanism 104. An investigator then logs into TEM collection device 100 using his/her assigned user ID and password, which makes him/her the official and only authorized user for the current usage session. When the investigator selects an "Enter" button, a photograph of the investigator can be taken by the wide angle video camera 126 (shown in FIG. 5) to provide a confirmation record. If desired, this function can be set so that the device takes additional user snapshots at various event or timing intervals while in use.

Figure 25:
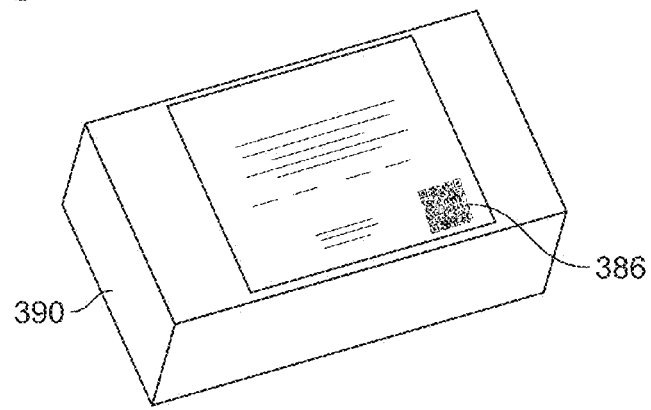
FIG. 25 is a perspective view of a carton having a QR or similar identifying code.

The investigator may then adjust various system settings (such as "Lighting") but will not yet be allowed to load a cassette (such as TEM collection cassette 116). After the settings have been adjusted, the investigator selects a "Load Cassette" button. The investigator then places a packaged sterile peel pouch cassette 384 and its QR product code label 386 (or a similar electronic readable letter or encoding symbol(s)) in front of wide angle video camera 126 (shown in FIG. 5) and presses a button on thumb control 110 or other input means to capture a photograph of packaged cassette 384 and QR product code label 386, as indicated by reference numeral 388. This photograph enables automatic input of the cassette's model number and unique serial number along with the loading date and time into the system and provides a visible record showing that the particular packaged cassette 384 is still securely factory sealed in its sterile peel pouch and therefore uncompromised and ready for use. It is also recommended that QR product code label 386 and similar marking codes be scanned on carton boxes (such as box 390 shown in FIG. 25) or other parts of the system. This information links each cassette back through to all of its manufacturing traceability records. In addition, each cassette comes with built-in internal digital memory technology that automatically can store various information such as a user(s), case number, TEM recovery location, time/date, etc., so that this information is also kept with the cassette at all times and therefore assures information continuity to other external TEM data.

Once product code label 386 and other related information is recorded, the system is designed so that only that particular cassette can be loaded into cassette drive mechanism 104. As the initial portion of the collection tape does not contain adhesive, the system is not yet considered "Active" and therefore an "Inactive" status can be shown in the status area and is recorded by the system with a time and date stamp. At this time, the cameras and other cassette mounted accessories can be installed if desired. If the pouch supplied sterile TEM roller cover 200 (shown in FIGS. 14A and 14B) has not been removed, TEM collection device 100 can be put down until it is ready to be used. However, it is considered best practices to always place TEM collection device 100 into security holder 328 (shown in FIG. 18).

Prior to use, security holder 328 can be electronically paired over a Bluetooth or similar data connection to touch screen display/CPU 106 using a security password or other secure methods. Both devices automatically exchange user and other basic information. Therefore, anytime the investigator wants to set down TEM collection device 100, he/she can select an "Open Security Holder" button on touch screen display/CPU 106, which commands security holder 328 to unlock so that he/she can quickly place the device and/or cassette inside and shut and automatically lock holder lid 330. Similarly, when the investigator wants to remove the device/cassette, he/she can select an "Unlock Lid" button and TEM collection device 100 automatically records these events with date and time stamps.

Security holder 328 also includes the ability to use a mechanical key and the option for the handle to issue a four digit lock pin code that can change or expire depending on procedural settings. The system automatically records when a particular user has safely secured the device and when that user removes the device from security holder 328. In fact, short of removing the battery, TEM collection device 100 will not allow itself to be shut down unless the user logs out and stores the in-use device in a procedurally correct way so that the storage disposition of the cassette is recorded. These simple actions automatically replace many related labor intensive trace evidence recovery requirements. If Internet enabled, TEM collection device 100 can also be made to automatically forward event/usage information to one or more forensic TEM analyzers and distribution systems or send emails or text messages to department or individuals if desired. This not only results in better and easier procedure conformance, but it also provides a significant savings of time that can be better used performing more important parts of the investigation.

When ready to use, the investigator selects a "Start TEM Collection" button and the screen will show that the device is in its start/active state. When ready to start collecting potential TEMs, the investigator simply pulls the handle's trigger. This first activates the video cameras and position recordings and then automatically advances collection tape 134 from it starting, non-adhesive portion so that the adhesive portion of the tape is now wrapped around TEM pickup roller 130 and ready for TEM collection. Preferably, the investigator waits until this time to remove TEM roller cover 200 and put it back on when not in use, which is something that can also be dictated by the system and confirmed by a recording using the wide-angle view video camera 126 or other data input means.

In this embodiment, there are two methods for TEM collection—linear and back-and-forth. Linear collection is where the investigator rolls TEM pickup roller 130 forward over a surface while he/she can also watch the high-resolution/magnification screen video of the TEMs as they are being collected and securely sealed away. At any time, the investigator can make and/or enter a written/drawn annotation on the screen. When the investigator lets go of the trigger, TEM collection device 100 will automatically advance collection tape 134 so that any exposed tape is passed through seal application rollers 140*a* and 140*b* (shown in FIG. 7) and securely sealed. In doing so, TEM collection device 100 ensures a physical segregation between each taping event, which is also recorded as individual TEM collection segments. The video and data recording will then stop and time stamp the beginning and end of TEM collection. The investigator can also easily initiate advancement of a section of tape to help to assure sample site segregation and so that special consideration may be given to any taped particulate in this area of tape if needed. These are just a few examples of how the system has the ability to easily and automatically require, verify and record compliance with many required TEM recovery procedures.

For linear tape position recording, TEM collection device 100 relies on various inputs to make sure that the linear tape position recorded matches the actual physical tape position. For example, cassette drive mechanism 104 can monitor component rotations to make sure that they are coordinated with a rotary position encoder 154 located on TEM pickup roller 130 (shown in FIG. 8) and therefore the linear movement of collection tape 134. This may also be done to make sure there is no slack in collection tape 134 during use and also to slightly drive collection tape 134 during use so that internal part friction (such as the unwinding of the adhesive tape) that could potentially hinder the rotation of TEM pickup roller 130 is kept to a minimum by using techniques well known to one skilled in the art. Camera 180 (shown in FIG. 11A) can also be utilized to assist with this much in the way that an optical mouse optically measures its own movement. The system can also periodically use camera 182 (shown in FIG. 11B) to do its own visual check of the physical tape's printed position relative to the recorded position and will use this physical tape position verification to automatically re-calibrate the liner tape position if needed.

Due to the internal solid-state compass and multi-axis accelerometers and similar position and movement measuring techniques, TEM collection device 100 is also able to detect when it is set down and, thus, it can be configured to record and timestamp these events and take photographs to record its placement and the user if picked up again. If a GPS signal is available, the device will also record this location information. The device can also be made to remind the user of correct temporary clean and secure placement procedures, such as making sure TEM roller cover 200 is used when needed. The device can also be made to initiate an auto-timeout and password reentry countdown or other procedures if desired. However, it is considered best practices to place TEM collection device 100 into security holder 328 anytime it is not in use. If the device is turned off or if handle assembly 102 or handle shaft 118 are disconnected, this event will be recorded and it will automatically initiate an auto tape advance and seal. To resume, the user ID and password must be re-entered and again the device will make sure that the original serial number and therefore "authorized" cassette is being used and that the tape is in the same position as before shut-down. If Internet enabled, TEM collection device 100 can also forward event/usage information to one or more forensic TEM analyzers and distribution systems or send emails or text messages to department or individuals if desired.

If TEM collection device 100 needs to be transported to another location or needs to be stored for a period of time while a cassette is still in-use, the investigator can initiate a transportation/hibernation function after placing the cassette into security holder 328. Security holder 328 will then lock the cassette in place and inform the user that he/she can now remove handle assembly 102 and/or handle shaft 118 for convenience if desired. If handle assembly 102 is removed, rubber plug 352 is provided to seal the holder's hole and optionally secured with a tamper evident seal if desired.

Each of the components of TEM collection device 100 (i.e., the components placed in security holder 328) can then go into a temporary low-power "hibernate mode" and will record this event and related information. As shown in FIG. 18, touch screen display/CPU 106 and handle assembly 102 can still be used to review the collection videos and other data collected during the collection process, make annotations, and upload or email any or all of the collected digital data to one or more forensic TEM analyzers and distribution systems or any other desired location.

After transportation/storage, the original investigator or a new investigator can login and initiate a "Resume" function on touch screen display/CPU 106 and handle assembly 102. At this time, the device will inform the user that he/she can re-insert handle assembly 102 and/or handle shaft 118 into cassette drive mechanism 104. The device will then go through a system check and a initiate a verification process to verify that the same cassette has been reinserted, the previous linear position of collection tape 134 has not changed, the cassette was always locked in security holder 328, if a mechanical key was used to open security holder 328, if the holder's battery went too low or dead (and therefore raises a question), if a potential undocumented event may have taken place, and the like.

In the event that the internal battery or other power source starts to get too low, security holder 328 will start to beep or otherwise provide an indication to one or more users. If Internet enabled, the device can send a low power message to one or more forensic TEM analyzers and distribution systems or send emails or text messages to a department or individuals if desired. Although this is relatively unlikely insofar as security holder 328 uses so little power in the hibernation mode, a fully charged holder can still monitor its use and security for months at a time. Security holder 328 may also employ a mechanical lid-opening event recording trigger that can be checked as a backup should the holder be allowed to go completely dead or its power removed.

Security holder 328 and its contents can then be delivered to a desired location and the investigator can employ the system's built-in chain of custody documentation system when delivering it to a forensic TEM analyzer and distribution system or any other entity/agency.

Figure 26A:
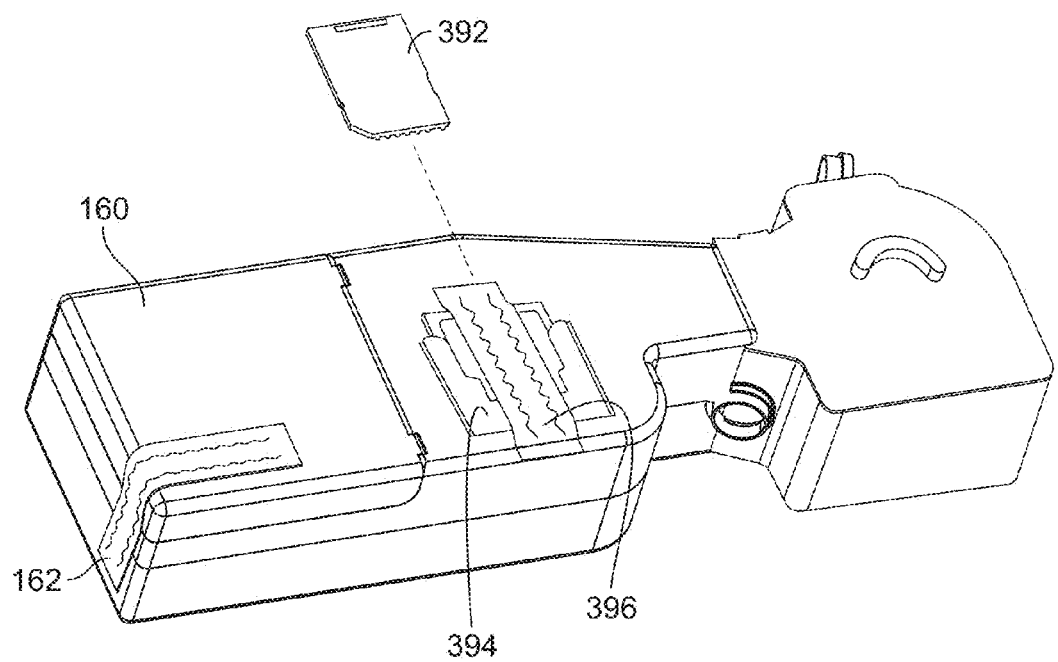
FIG. 26A is a perspective view of the TEM collection cassette showing the secured placement of a digital memory card and the secured access point or door.
Figure 26B:
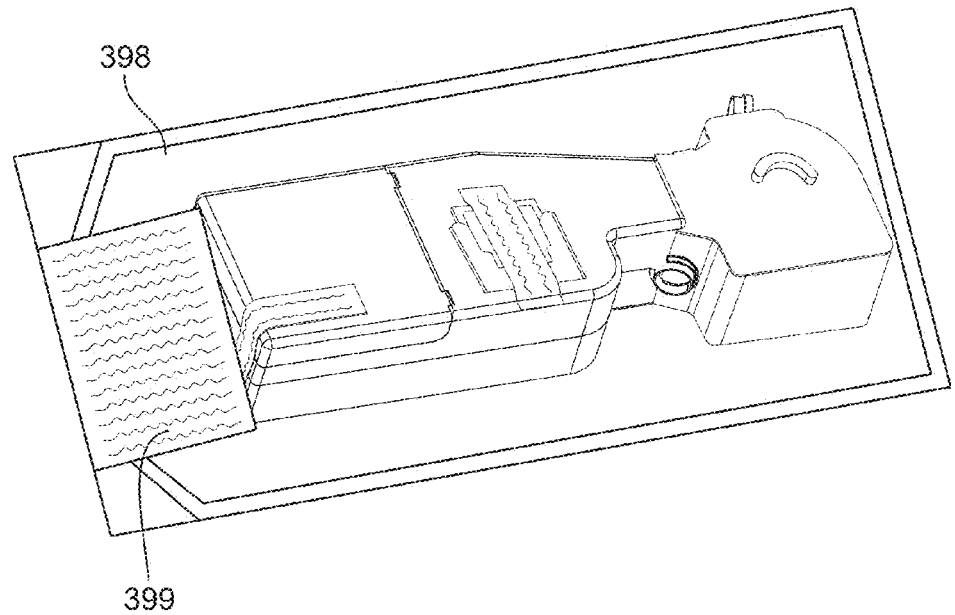
FIG. 26B is a perspective view of the TEM collection cassette placed in a peel pouch that is secured using an evidence sealing chain-of-custody label.

FIGS. 26A and 26B depict an easy and secure method of transporting and storing TEM collection cassette 116 and its digital memory card 392. The investigator inserts digital memory card 392 into a built-in digital memory card holder 394 and then secures it with a standard tamper evident seal 396. Access point or door 160 is also secured with tamper evident seal 162. TEM collection cassette 116 with digital memory card 392 inserted therein is then placed back into the cassette's original peel pouch 398 and sealed with a standard, evidence-sealing chain of custody label 399. As such, the collected TEMs and TEM data are retained together to prevent loss or mix-up until it is desirable to remove the collected TEMs and TEM data in a procedurally secure and documented manner. Therefore, unlike conventional TEM recovery methods, this single, small, secure package contains very large amounts of TEMs, the wide angle crime scene video/audio, the close-up video of the surface being taped, the high-resolution, high magnification video of the collected TEMs, and the TEM collector's audio/written/drawn crime scene annotations along with all of the other precision TEM collection position/location data. Alternatively, TEM collection cassette 116 and digital memory card 392 may be securely packaged for transportation using any suitable, standard evidence packaging, transportation and chain of custody techniques known in the art. One skilled in the art will appreciate how these built-in, small, secure packaging features are a significant improvement compared to conventional packaging of individual TEMs and the related identification and position documentation techniques described above.

The system also facilitates long term storage traceability requirements, such as when the case is closed or put on hold. The physical TEMs and all of the associated digital data can be logged into forensic TEM analyzer 300 or similar computer systems using the system's evidence/event storage log, which tracks all events relative to the particular TEM collection cassette 116. The system's ability to store large amounts of both physical TEMs and digital data for long periods of time, which can easily be retrieved and digitally reviewed at any time, can be crucial later on as additional information relative to important TEMs is acquired, even after the case has been closed or put on hold.

Therefore, the system utilizes a more holistic process that integrates crime scene management within the scientific scrutiny and supports a model whereby TEMs are considered as a greater part of frontline detection and whose results may be contextualized and integrated with other forensic case data to rapidly feed intelligence and investigation processes. Efficiently being able to recover large amounts of TEMs from the crime scene along with the real-time digitization and distribution of TEM information and related crime scene data to forensic TEM experts and other investigative entities through an optimized reporting and distribution process/system can lead to significant improvements in the speed and ability in which TEMs are utilized to solve crimes.

B. Swabbing Pad Embodiments

Another exemplary embodiment of a system in accordance with the present invention is generally comprised of a TEM collection device 400 (shown in FIG. 27) that is particularly suitable for use in the collection of very small DNA samples, such as touch DNA, which are immediately sealed and cut into individually numbered touch DNA samples 402 that are deposited into a clear swab drying container 404. TEM collection device 400 may be used in combination with one or more forensic TEM analyzers (such as forensic TEM analyzer 300 shown in FIG. 17 and described above).

The main components of TEM collection device 400 are shown in FIG. 27. As can be seen, TEM collection device 400 includes a reusable handle 406 into which is inserted a small, sterile, single-use touch DNA swabbing cassette 408. Swabbing cassette 408 has a TEM collection end in the form of an oval shaped DNA swabbing tip 410 that approximates the size and shape of a typical touch DNA swab (approximately 0.25"×0.50"). Of course, the swabbing tip may come in a variety of sizes and shapes. In this embodiment, DNA swabbing tip 410 includes a thin substrate 432 wrapped around its surface which has an absorbent swabbing pad 434. The absorbent swabbing pad 434 may be rubbed across a surface so that it collects and retains touch DNA samples, as will be described. TEM collection device 400 also includes a DNA swabbing cassette shaft 412, forensic light sources 414a and 414b, a forward facing video camera 416, and a trigger 418.

Figure 28:
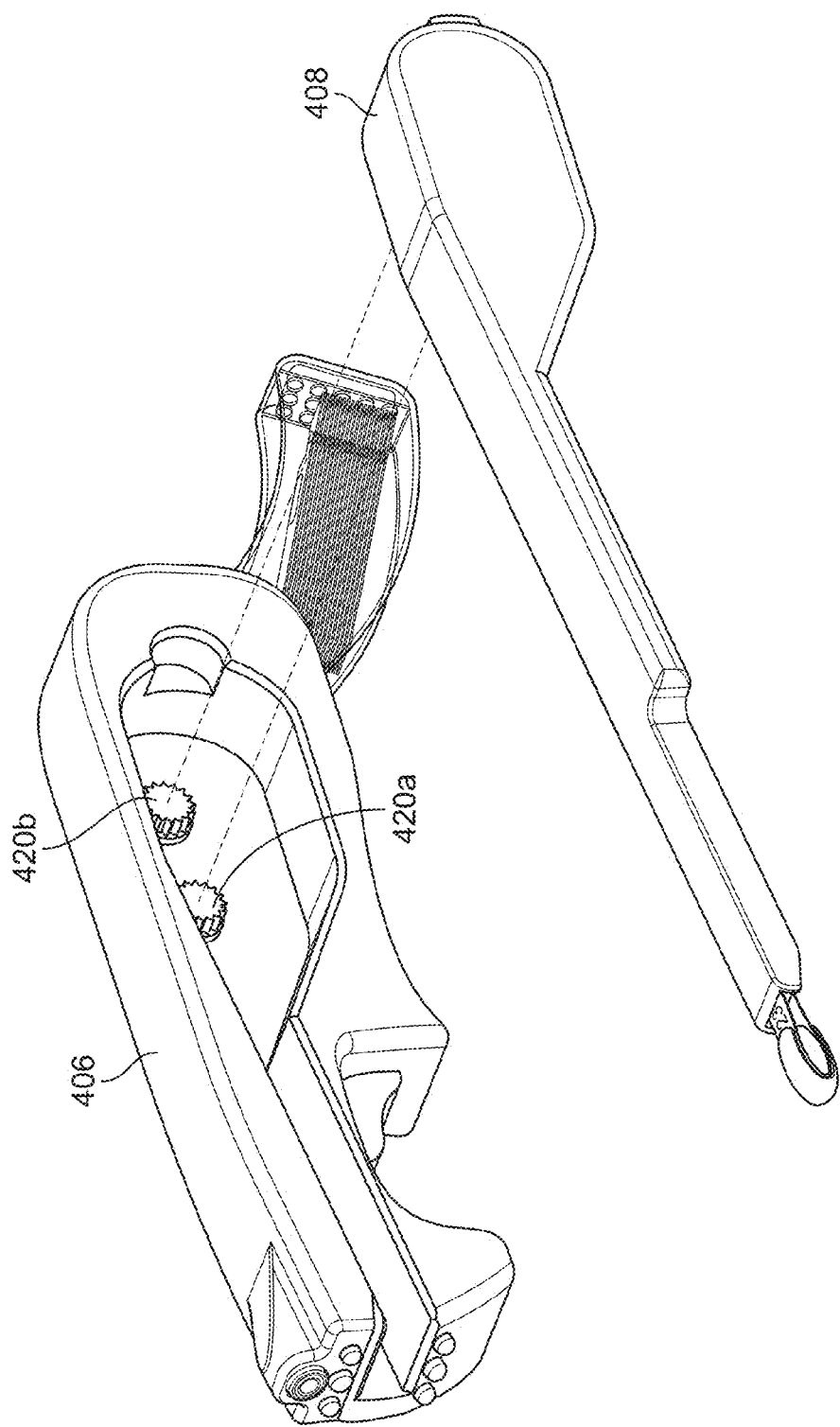
FIG. 28 is a perspective view of the TEM collection device with the DNA swabbing cassette detached from the handle.

FIG. 28 shows handle 406 and rotational drive wheels 420a and 420b that drive mating parts in DNA swabbing cassette 408. Drive wheels 420a and 420b may be actuated by a motor, solenoid, hand/finger movement or other similar actuators. Handle 406 may have any type of driving mechanism and may also have electrical connectors implemented between handle 406 and DNA swabbing cassette 408, as described in connection with the collection tape embodiments. Handle 406 may be electrically powered by an internal rechargeable battery or removable battery pack and/or external power cord.

Figure 29:
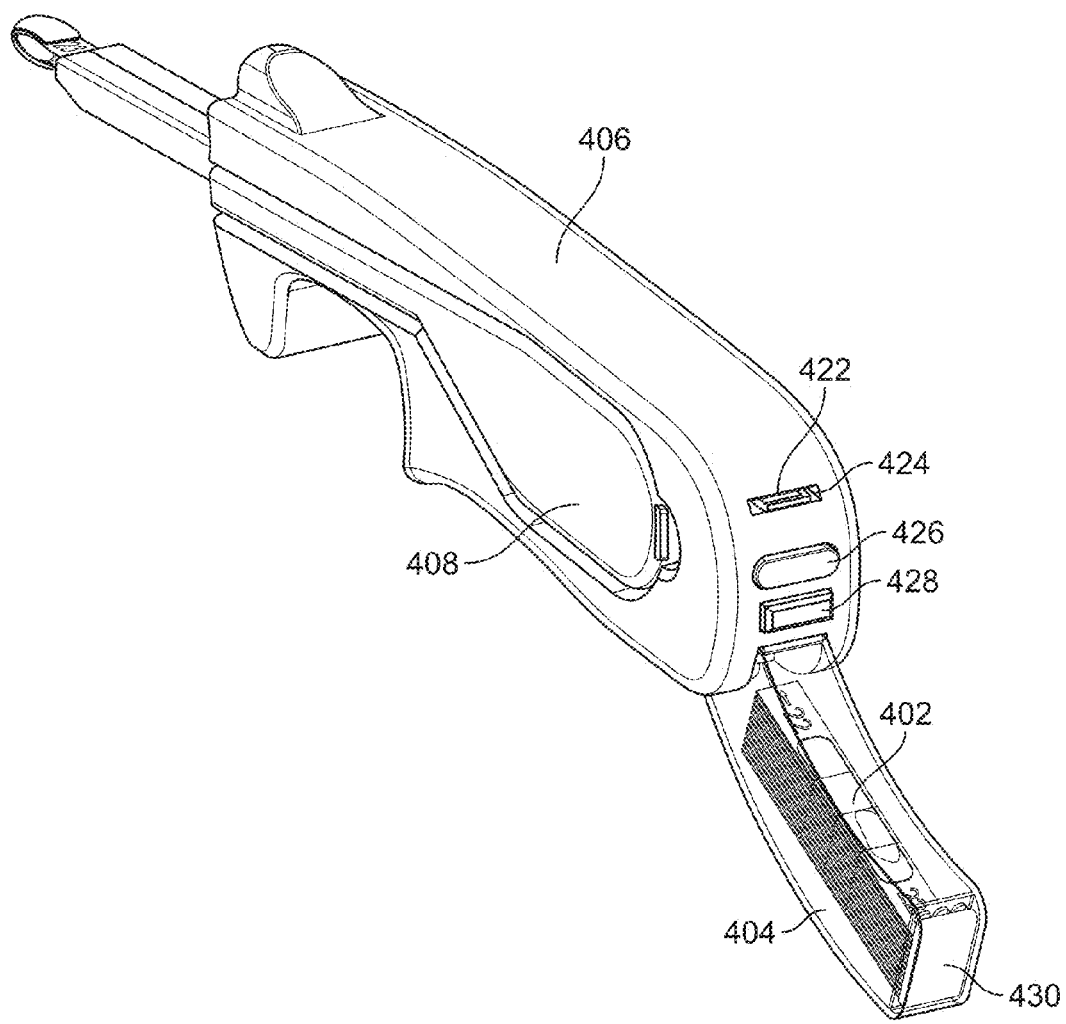
FIG. 29 is a rear perspective view of the TEM collection device.

FIG. 29 is a rear perspective view of TEM collection device 400 showing DNA swabbing cassette 408, handle 406, and clear swab drying container 404 containing touch DNA samples 402. Also shown is a digital memory card 422 in a card slot 424, a power button 426, a drying container eject button 428, and a drying container desiccant 430.

Figure 30A:
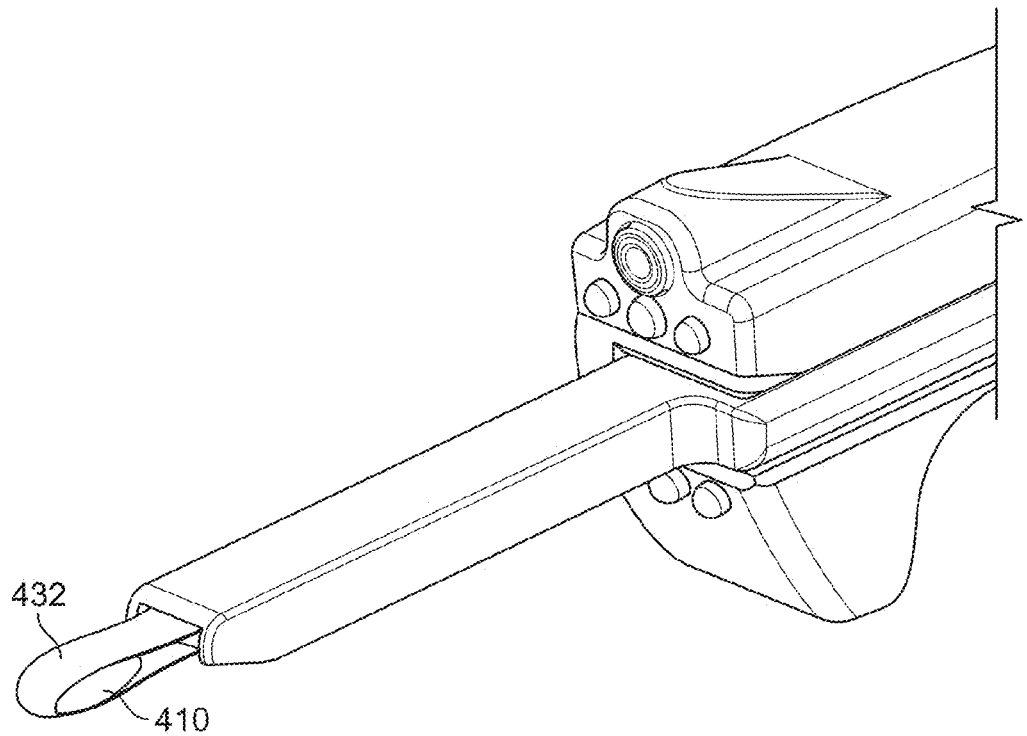
FIG. 30A is a perspective view of the front end of the TEM collection device showing the swabbing tip with only the non-absorbent substrate present.
Figure 30B:
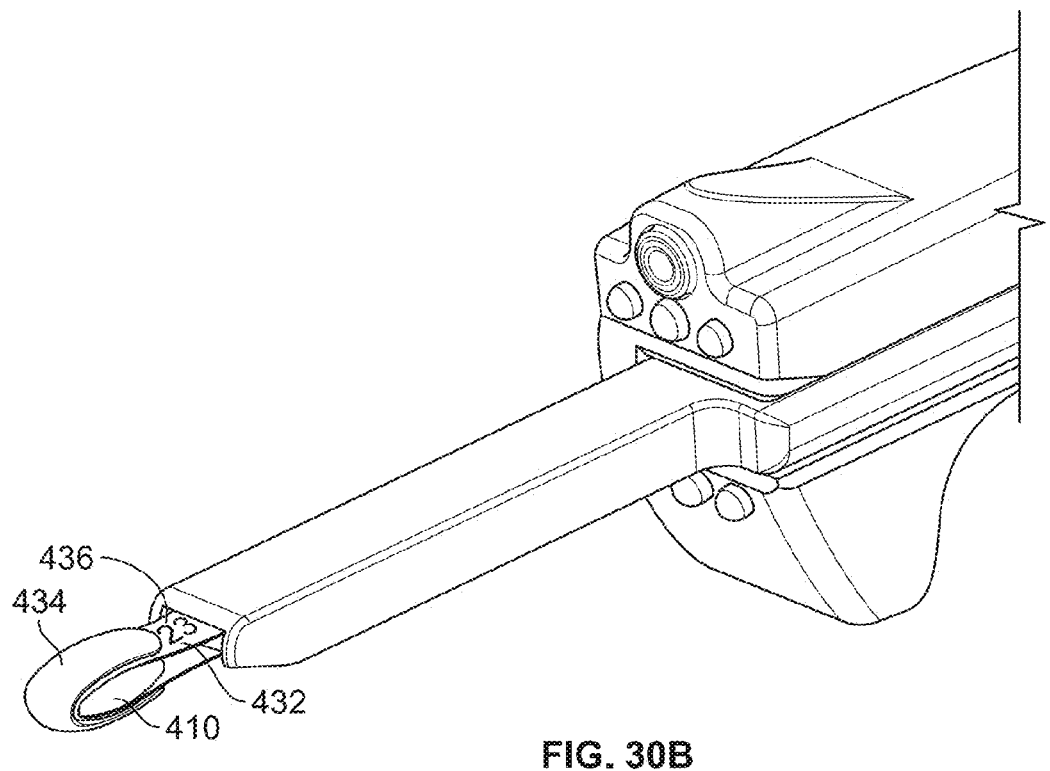
FIG. 30B is a perspective view of the front end of the TEM collection device showing the swabbing tip with both the non-absorbent substrate and absorbent swabbing pad present.

TEM collection device 400 has the ability to collect and retain touch DNA samples by one or more methods. In this embodiment, DNA swabbing tip 410 includes a thin non-absorbent substrate 432 wrapped around its surface, as shown in FIG. 30A. Substrate 432 has at least one particulate and/or absorbent swabbing pad 434, shown in FIG. 30B, which is attached to substrate 432 and can be used to collect a touch DNA sample. In one example, swabbing pad 434 is made using a process called "flocking" to create a material known for use in the collection of touch DNA that is considered far superior to cotton when it comes to adherence to substrates, DNA sample uptake and sample release.

It should be understood that the device could use one more different type of materials to form this particulate and/or absorbent swabbing pad. Preferably, the device includes multiple swabbing pads spaced along the length of substrate 432 so that a new, clean particulate and absorbent swabbing pad is provided each time trigger 418 on handle 406 is pulled. Also shown is a sample number 436 located on substrate 432 that indicates the number of the current sample being taken (in this example sample number "23").

Figure 31:
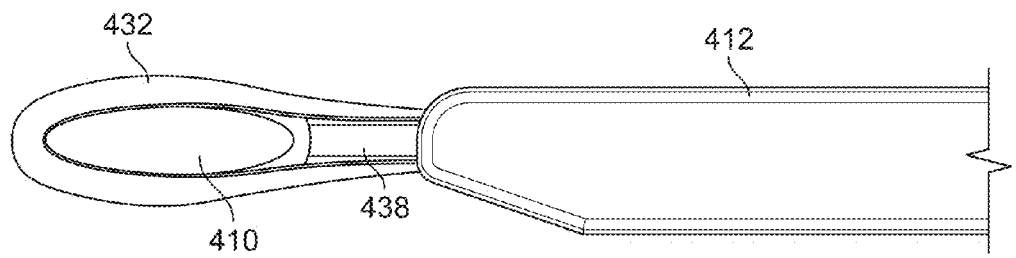
FIG. 31 is a side view of the front end of the TEM collection device showing the swabbing tip with only the non-absorbent substrate present.
Figure 32:
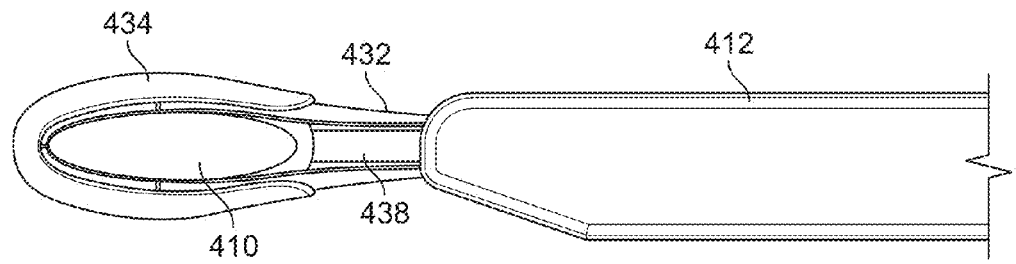
FIG. 32 is a side view of the front end of the TEM collection device showing the swabbing tip with both the non-absorbent substrate and absorbent swabbing pad present.

FIGS. 31 and 32 are sides view of cassette shaft 412 showing swabbing tip 410 located on the end of a tip shaft 438. In FIG. 31, swabbing tip 410 only has non-absorbent substrate 432 wrapped around its surface. FIG. 32 also includes swabbing pad 434 located on substrate 432 and both are wrapped around swabbing tip 410. In this embodiment, substrate 432 and swabbing pad 434 are drawn over swabbing tip 410 in such a way so as to cause the sides of substrate 432 and swabbing pad 434 to conform around the sides of swabbing tip 410 via any suitable method. For example, swabbing cassette 408 may put substrate 432 and swabbing pad 434 in a tensioned/stretched state so as to achieve such side area conformability. Alternatively, materials having varying thicknesses may be used, films with non-linear or directional deformation properties may be used, and/or the use of guides may be used to help provide this function.

Prior to taking a touch DNA sample, swabbing tip 410 only has non-absorbent substrate 432 wrapped around its surface and thus is not ready to collect a touch DNA sample. When the investigator desires to take a DNA sample on a given surface, he/she pulls trigger 418 located on handle 406 which causes the forward facing video camera 174 to turn on and record video and/or photographs of swabbing tip 410 and the surface, area or item that may contain touch DNA so as to provide a record of where a particular sample was taken. TEM collection device 400 then advances substrate 432 so that an absorbent swabbing pad 434 is wrapped around swabbing tip 410. In this embodiment, substrate 432 would also expose and show the sample number 436 associated with that particular swabbing pad.

The user then rubs swabbing tip 410 covered by swabbing pad 434 over the surface containing the touch DNA so that they are collected on swabbing pad 434. When releasing trigger 418, TEM collection device 400 advances substrate 432 so that swabbing pad 434 containing the touch DNA advances around and below swabbing tip 410 and back into the lower portion of cassette shaft 412 where swabbing pad 434 containing the touch DNA is sealed (as will be described below) and once again only non-absorbent substrate 432 is now exposed, at which point the forward facing video camera 416 will stop recording videos and/or photographs.

Figure 33:
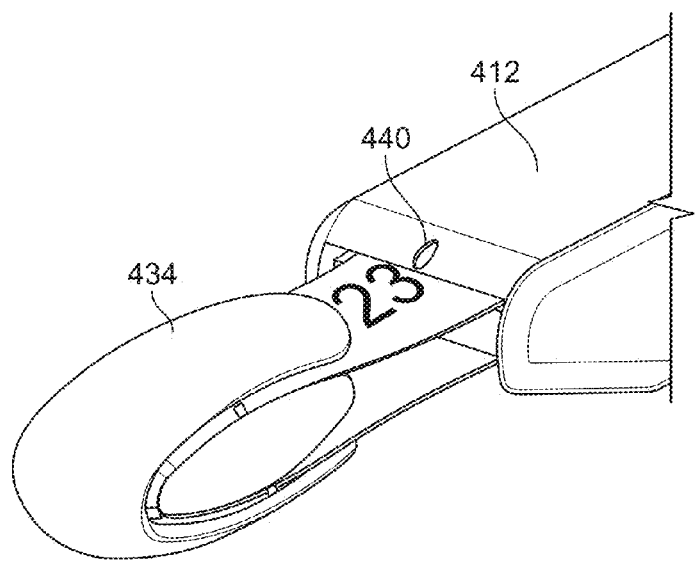
FIG. 33 is a perspective view of the cassette shaft and swabbing tip showing a swab moisture applicator.

FIG. 33 shows an embodiment in which a swab moisture applicator 440 can be used to moisten swabbing pad 434 with water, buffered saline, lysis buffers, or similar media, which is common with the use of touch DNA swabs during sample collection. Moisture applicator 440 may be comprised of a hole, a tube, or any other conduit means capable of delivering the media to swabbing pad 434 when desired.

Figure 34:
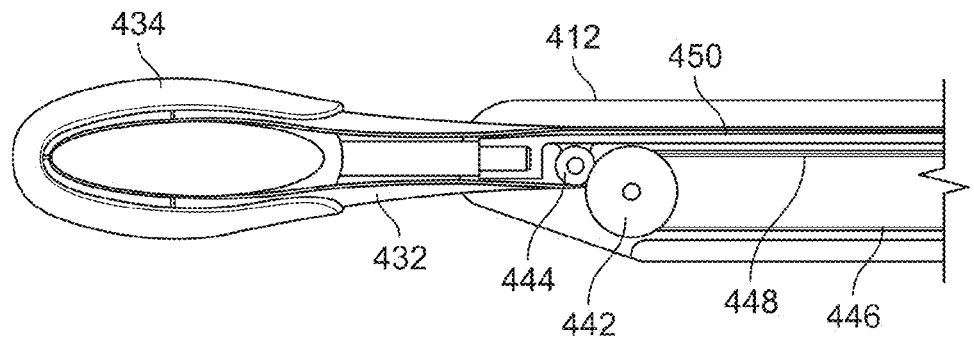
FIG. 34 is a cutaway side view of the cassette shaft showing the internal seal applicator components.

FIG. 34 is a cross-sectional view of cassette shaft 412 showing one exemplary method for sealing swabbing pad 434 after it collects a touch DNA sample. In this embodiment, a seal applicator roller 442 and a roller guide 444 are used to apply an upper seal 446 to substrate 432 and swabbing pad 434 containing the touch DNA sample to thereby create a substrate/swabbing pad/seal laminate 448. In this case, the back side of substrate 432 functions as the lower seal (although a separate lower seal could also be used). Seal applicator roller 442 is separated from the not yet used upper substrate 432 and swabbing pad 434 by a sealing chamber separator 450.

Figure 35:
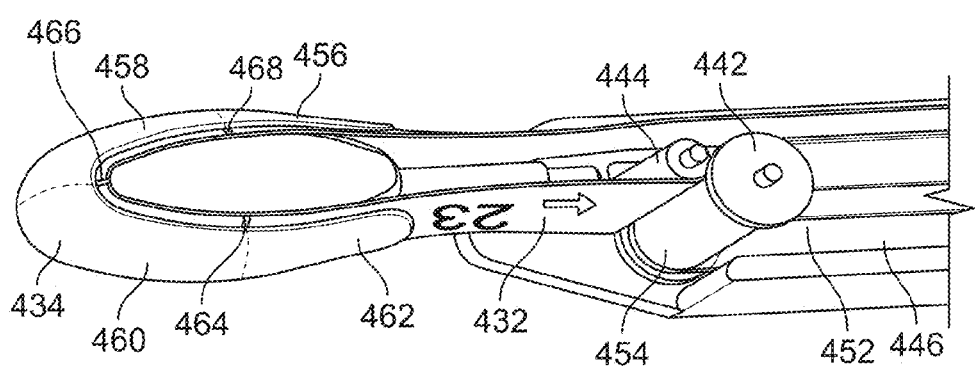
FIG. 35 is a cutaway perspective view of the cassette shaft showing the internal seal applicator components, as well as the markers and sections of the absorbent swabbing pad.

FIG. 35 is a perspective cross-sectional view of cassette shaft 412 showing the sealing of swabbing pad 434 after it collects a touch DNA sample. Immediately after diverging from the bottom of swabbing tip 410, substrate 432 and swabbing pad 434 containing the touch DNA sample pass between seal applicator roller 442 and roller guide 444, which immediately apply preferably clear upper seal 446 (and optionally a lower seal) that is fed from an upper seal reel (not shown, but similar to seal reel 156 described above). Swabbing pad 434 containing the touch DNA sample is thus contained between substrate 432 and upper seal 446. Upper seal 446 has a peelable and preferably tamper-evident adhesive 452 applied to its side edges that enables upper seal 446 to adhere to substrate 432 as substrate 432 and upper seal 446 pass between seal applicator roller 442 and roller guide 444 thereby trapping and isolating the touch DNA contained on swabbing pad 434 in between.

Seal applicator roller 442 is preferably made of a relatively soft elastomer to assist with the compression and adherence of substrate 432 to upper seal 446. Seal applicator roller 442 may also have a soft foam or otherwise easily conformable center section 183 that may be used to assist with conformance of upper seal 446 over swabbing pad 434 and the compression and adherence of substrate 432 to upper seal 446.

There are many substrate and seal material options that could be used in swabbing cassette 408. Cassettes may also be sold with different material options and sizes for different uses. For example, the upper seal may be clear, semi-transparent or opaque and may be white or another color. For wet samples that should be promptly allowed to dry per typical TEM recovery procedures, one or more of the seals can be made of any number of widely available air-permeable materials that can also be transparent. Alternatively, very small holes could be made in one or more of the seals. The substrate could include a hydrophilic desiccant or the substrate, seals or even the seal adhesive could be made of a hydrophilic desiccant material.

Also shown in FIG. 35 are various sections of swabbing pad 434, including upper rear section 456, upper front section 458, lower front section 460 and lower rear section 462. Also shown are a leading marker 464, a center marker 466 and a trailing marker 468. Each of these elements will be described in greater detail in connection with FIG. 36.

Similar to the seal and cut assembly of TEM collection device 100 described above, TEM collection device 400 of this exemplary embodiment cuts each numbered swab segment and deposits it into clear swab drying container 404 of handle 406. Alternatively, substrate 432 and swabbing pads 434 could be rolled up and stored on a take-up reel. In both cases, two separate seals may be applied to opposite sides of the substrate/swabbing pads after collection of the TEMs so as to enclose the entire substrate/swabbing pads containing the collected TEMs between the seals. Or, one separate seal may be applied to the side of the substrate with the swabbing pads, and the back side of the substrate will serve as the second seal (as shown in FIGS. 34 and 35).

In other embodiments, no separate seals are applied after collection of the TEMs and the substrate itself when rolled up and stored on a take-up reel provides the sealing function. Specifically, for each swabbing pad containing collected TEMs, the back side of the substrate for a previous substrate segment on the roll serves as the first seal (i.e., the substrate segment whose back side is positioned adjacent the swabbing pad on the roll) and the back side of the substrate segment containing the swabbing pad serves as the second seal. In this case, the swabbing pads containing the collected TEMs would be exposed when the rolled substrate stored on the take-up reel is unrolled and, as such, the unrolling of the substrate would preferably be performed in a controlled manner.

Figure 36:
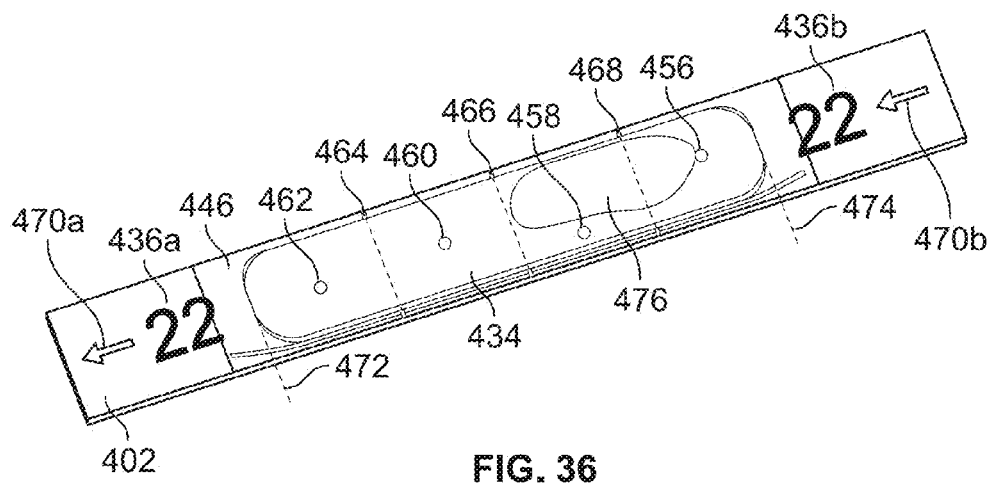
FIG. 36 is a perspective view of single touch DNA sample along with its various elements.

FIG. 36 shows a sealed touch DNA sample 402 if it has been cut into an individual sample segment. This particular sample segment is sample number "22," as shown by reference numerals 436a and 436b. The direction of travel is depicted by the sample directional arrows 470a and 470b. As such, a swabbing pad leading edge 472 and swabbing pad trailing edge 474 can easily be determined. The use of sample directional arrows 470a and 470b, sample numbering 436a and 436b, swabbing pad leading edge 472, leading marker 464, center marker 466, trailing marker 468 and swabbing pad trailing edge 474, allow the user to divide swabbing pad 434 into four discrete sections, namely, upper rear section 456, upper front section 458, lower front section 460 and lower rear section 462 (also shown in FIG. 35). These swab sections are useful in identifying areas of swabbing pad 434 on which DNA source material 476 was obtained. Conversely, these swab sections can also be used to show where no material was found. In this example, DNA source material 476 extends between upper rear section 456 and upper front section 458 of swabbing pad 456. The device may also integrate one or more forensic laboratory analysis functions, such as DNA analysis, using technologies often described as lab-on-a-chip or micro-tool analysis systems, which can also integrate TEM sample pre-treatment steps, additional cleaning and separation steps towards quicker laboratory analysis than those usually done at lab-scale facilities.

Figure 37:
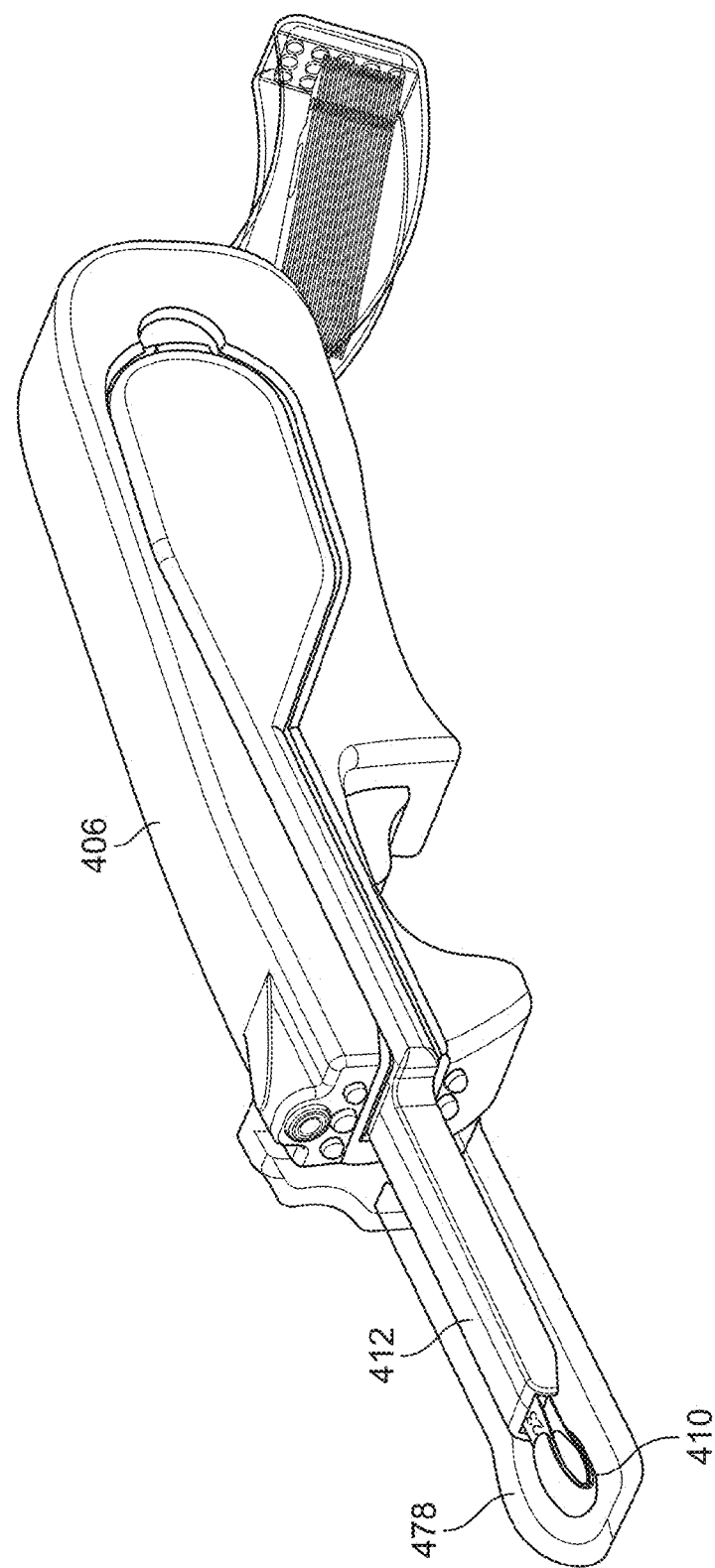
FIG. 37 is a perspective view of the TEM collection device showing the protective swabbing tip cover.

FIG. 37 shows a cover 478 that is used to cover cassette shaft 412 and swabbing tip 410 and can also be used to cover the forward facing video camera 416 and forensic lighting 414a and 414b. In this embodiment, each swabbing cassette 408 preferably comes packaged with a sterile cover 478 already installed. Cover 478 helps to insure that swabbing tip 410 is kept clean and secure during the installation of swabbing cassette 408 into handle 406 or any time it is desirable to cover swabbing tip 410 during use or during transportation and storage. Cover 478 can be also be used with a tamper evident seal 134 to prove that swabbing tip 410 was covered until removal of cover 478 in a procedurally secure and documented manner.

QR codes or other descriptive codes on the swabbing cassette case and carton boxes or other parts of the system can be visualized and information recorded by the forward facing video camera 416. This information links each swabbing cassette back through to all of its manufacturing traceability records. In addition, each swabbing cassette comes with built-in internal digital memory technology that automatically stores various information, such as a user(s), case number, TEM recovery location, time/date, etc., so that this information is also kept with the swabbing cassette at all times and therefore assures information continuity to other external TEM data.

Figure 38:
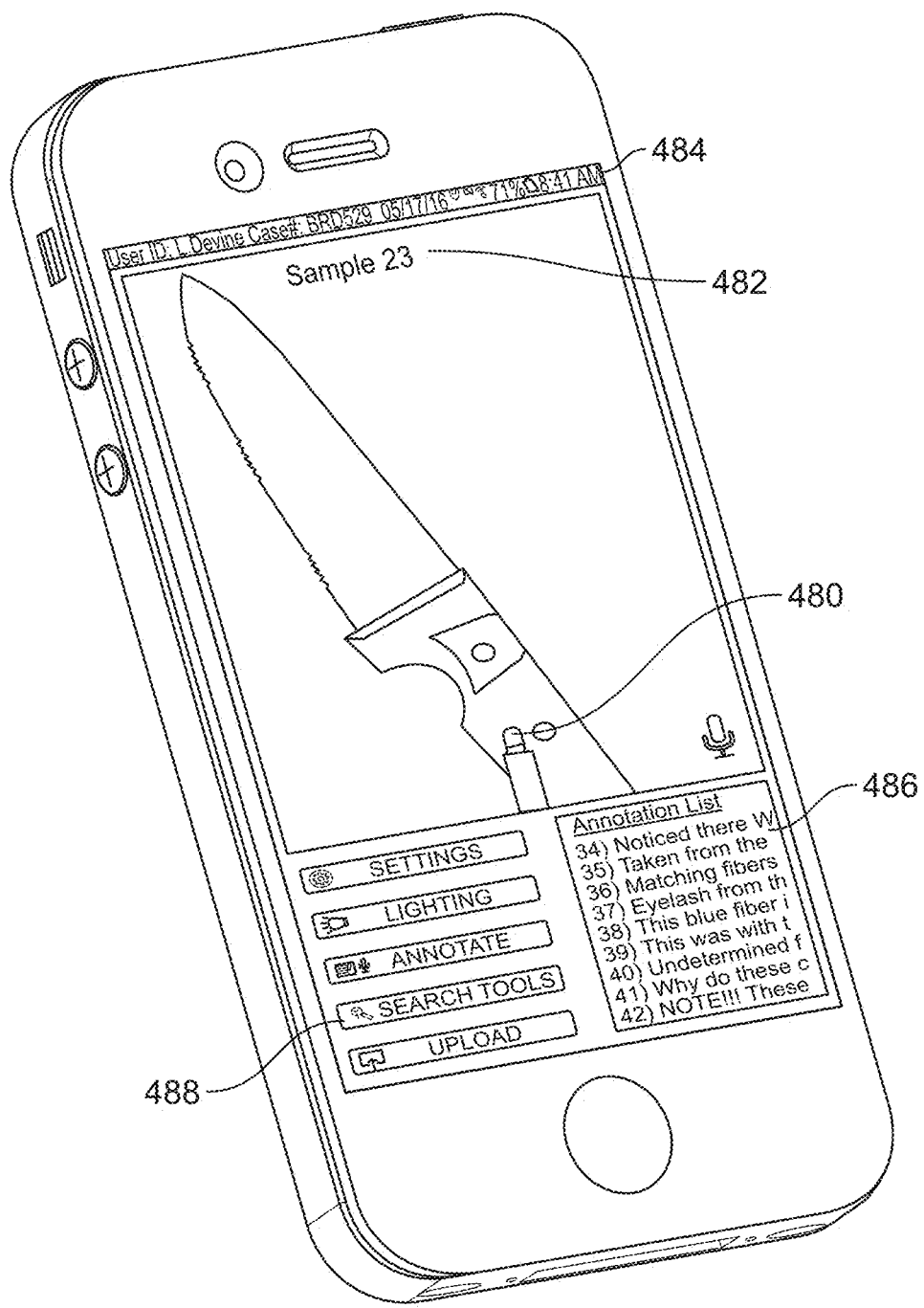
FIG. 38 is a perspective view of a touch screen display of a smartphone showing information that may be presented while the TEM collection device is being used to collect touch DNA.

In this embodiment, various aspects and functions of TEM collection device 400 can be controlled through the use of a smartphone, tablet or other suitable computational/display device and software, which is preferably Bluetooth/Wi-Fi or otherwise electronically communication enabled. As shown in the screen shot of FIG. 38, video/photographs from the forward facing video camera 416 can be used to present and record the item and/or area being sampled 48 along with the sample number 482, status bar 484, annotation list 486, menu buttons 488, etc. (similar to the screen shots shown in FIGS. 15 and 16 of the collection tape embodiments). It should be noted that this screen shot is merely an example of the basic intended usage of a video display and does not limit the scope of the present invention. TEM collection device 400 can also implement similar procedural function and documentation capabilities when coupled with a computational/display device and whose usage could be closely integrated with the system described above and other associated TEM software and component interoperability, such as with the use of a security holder.

Figure 39:
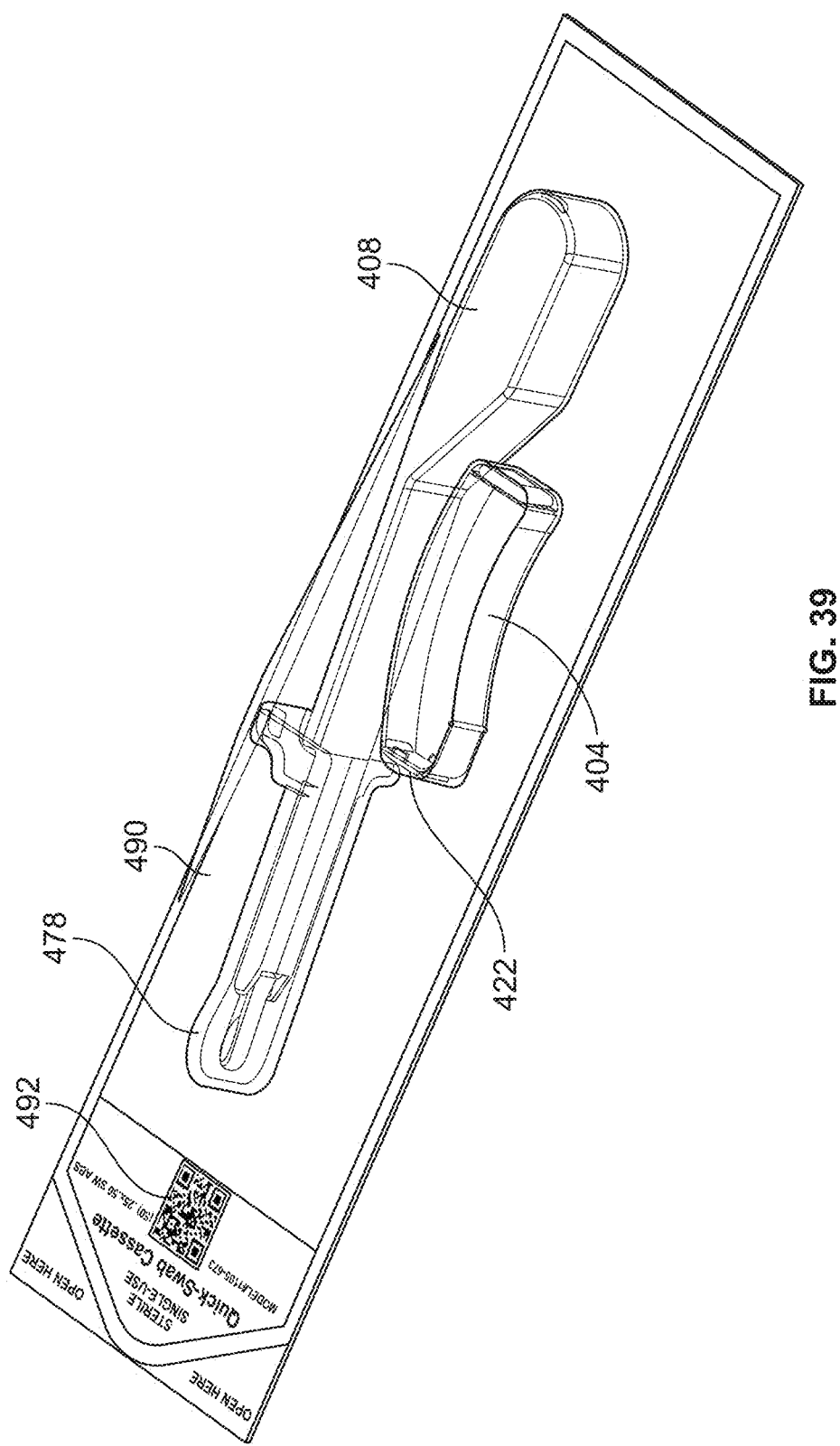
FIG. 39 is a perspective view of the TEM collection cassette, a clear drying container; a digital memory card and a swabbing tip cover packaged in a peel pouch.

FIG. 39 shows swabbing cassette 408, clear swab drying container 404 containing digital memory card 422, and cover 478, all of which are preferably packaged in a sterile product peel pouch 490. Peel pouch 490 has a QR product code label 492 or similar electronic readable letter or encoding symbol(s) to facilitate various automated or semi-automated system inputs, traceability and/or procedural functionalities similar to those described in connection with FIG. 24.

Figure 40:
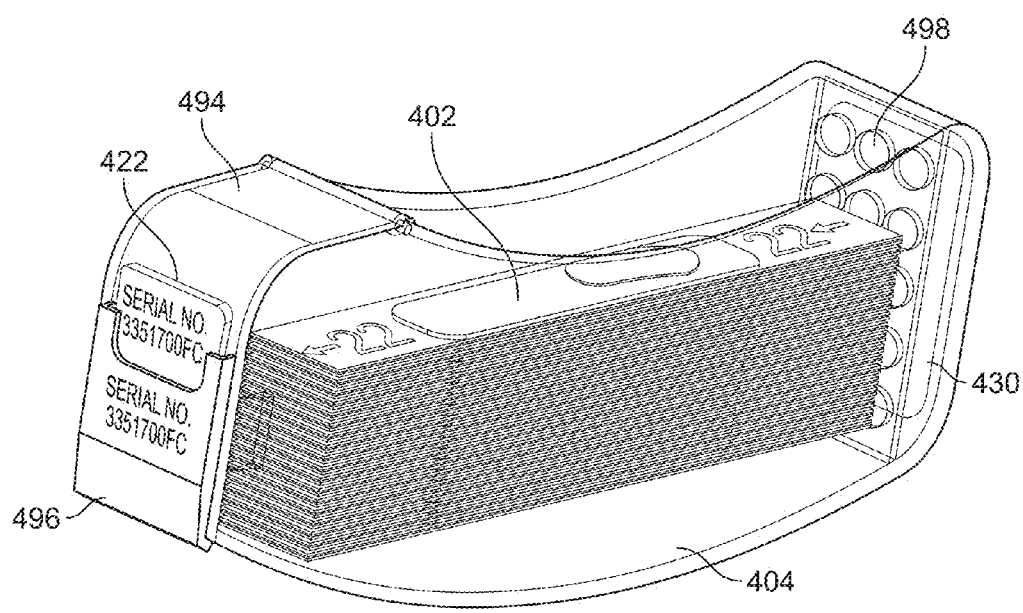
FIG. 40 is perspective view of a touch DNA sample drying container.

FIG. 40 shows clear swab drying container 404 having a container door 494, a digital memory card holder 496, digital memory card 422, and sealed touch DNA sample 402. As touch DNA samples are collected and sealed, they are placed into clear swab drying container 404. As per standard touch DNA sampling procedures, the touch DNA samples may be allowed or helped to dry by the use of a desiccant placed in a container with the DNA samples. In this embodiment, desiccant 430 is placed in drying container 404 and is separated by an air and moisture permeable barrier 498, such as in the form of a separating wall with a plurality of air/moisture transmitting holes. Of course, it should be noted that a barrier of this or any other type is not necessarily needed to facilitate the use of a desiccant. Drying container 404 may also utilize UV and other electromagnetic filtering technologies to aid in the preservation of the touch DNA samples.

Figure 41:
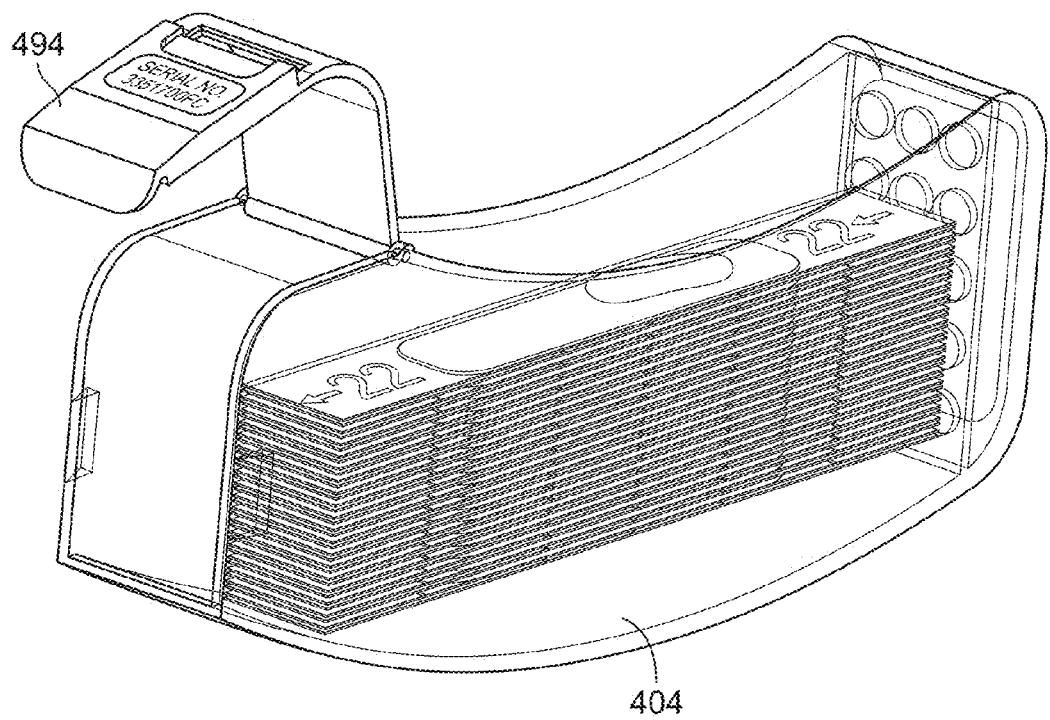
FIG. 41 is a perspective view of the touch DNA drying container with its container door open so that the sealed touch DNA samples can be inserted or retrieved.

FIG. 41 shows drying container 404 with its container door 494 open so that the sealed touch DNA samples can be inserted or retrieved.

Figure 42:
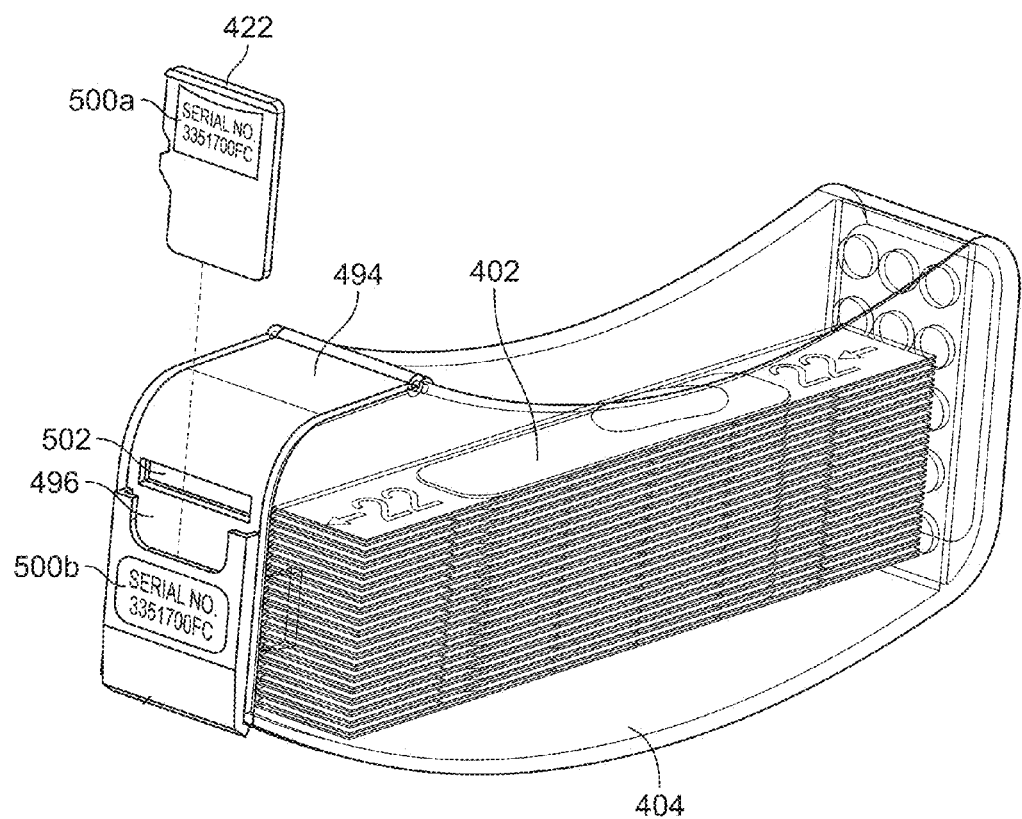
FIG. 42 is a perspective view of the touch DNA drying container with its container door closed and showing the matching identification numbers for the digital memory card and the drying container.

FIG. 42 shows drying container 404 with its container door 494 closed. As can be seen, digital memory card 422 and drying container 404 have similar or otherwise matching numbers or other identification coding means 500a and 500b, which serve to associate the TEM data contained on digital memory card 422 to the sealed touch DNA samples 402 contained in drying container 404 so as to help to prevent loss or mix up and to assist with chain of custody documentation and other TEM recovery procedures as previously described. As can also be seen, container door 494 has a drying container slot 502 that is used to insert the sealed and cut touch DNA samples 402 so that they are automatically stored in drying container 404 when it is inserted into handle 406. Of course, slot 502 can also be used manually or by other mechanisms. In this embodiment, the placement of slot 502 is such that digital memory card 422 also serves as a sliding door so that the sealed touch DNA samples 402 cannot be inserted when the digital memory card is still located in digital memory card holder 496. This helps to assure that the particular digital memory card is removed and placed into the device prior to use. In addition, the device can also implement software, hardware and/or mechanisms that will prohibit the insertion of drying container 404 into handle 406 when the memory card is still located in container door 494 so as to assure that only the memory card having identification coding matching that of the particular drying container is loaded into the handle or other suitably useful location.

Figure 43:
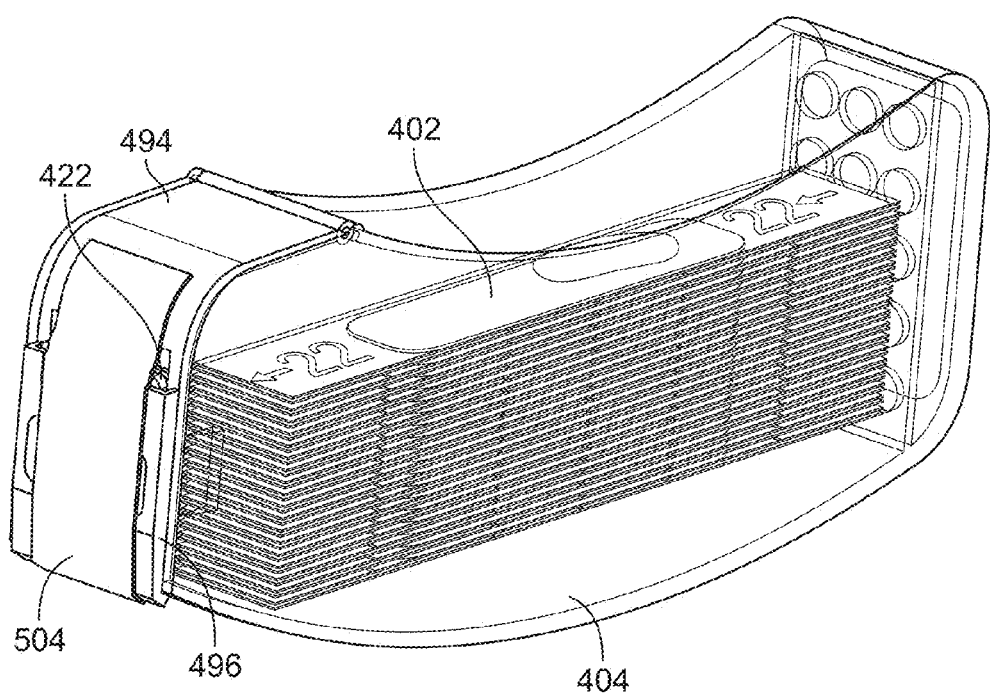
FIG. 43 is a perspective view of the touch DNA drying container in which the touch DNA samples and digital memory card are secured with a standard tamper evident seal.

FIG. 43 depicts an easy and secure method of transporting and storing drying container 404 and digital memory card 422 in which the user puts digital memory card 422 into digital memory card holder 496 and then secures it with a standard tamper evident seal 504 until such a time when it is desirable to remove touch DNA samples 402 and the associated digital memory card 422 in a procedurally secure and documented manner. As described in the collection tape embodiments, this combined/sealed package can then be placed back into the cassette's original peel pouch and sealed with a standard, evidence-sealing chain of custody label so that the touch DNA samples and associated data are kept together to help prevent loss or mix-up until it is desirable to remove the collected touch DNA samples and data in a procedurally secure and documented manner. Therefore, this single, small, secure package would contain very large amounts of touch DNA samples, the video from forward facing video camera 416, and the collector's audio/written/drawn crime scene annotations along with other position/location data. Alternatively, the cassette and digital memory card can be securely packaged for transportation using any suitable, standard evidence packaging, transportation and chain of custody techniques known in the art. One skilled in the art will appreciate how these built-in, small, secure packaging features are a significant improvement compared to conventional packaging of touch DNA and the related identification and position documentation techniques described above.

Figure 44A:
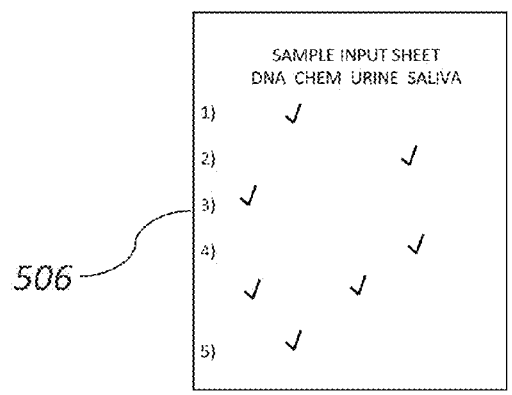
FIGS. 44A, 44B and 44C provide an overview of an exemplary process in which automated and/or semi-automated laboratory analysis technologies and equipment may be integrated into the system to assist with the touch DNA sample analysis.
Figure 44B:
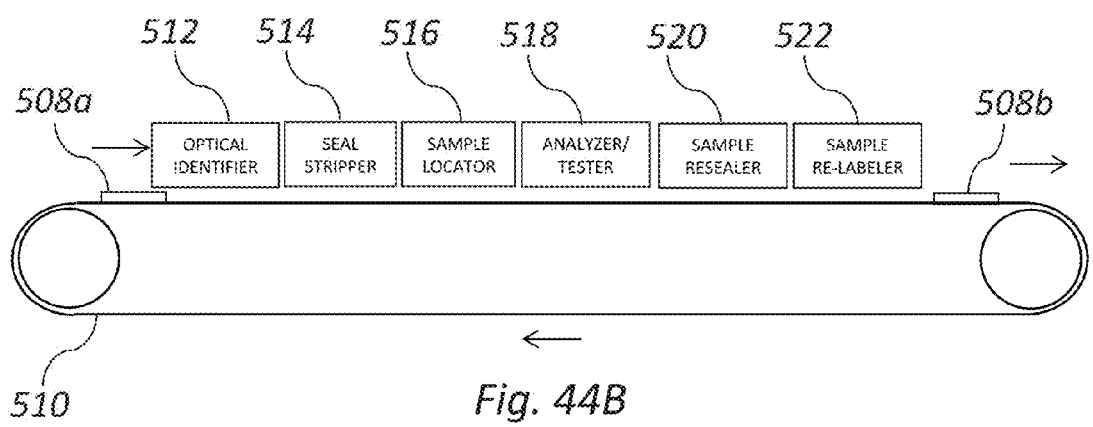
Figure 44C:
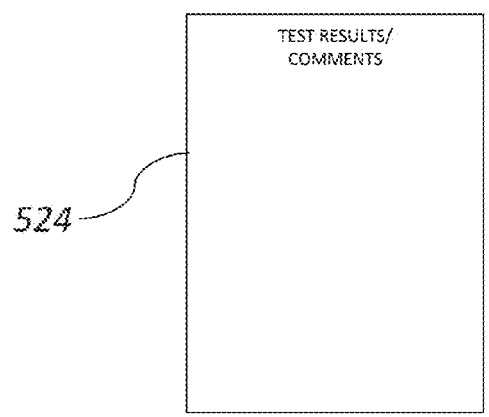

FIGS. 44A-44C provide an overview of an exemplary process in which automated and/or semi-automated laboratory analysis technologies and equipment may be integrated into the system to assist with the ease and speed of touch DNA sample analysis. As shown in FIG. 44A, a touch DNA sample input sheet 506 may be used to facilitate the correct type of analysis to be used in analyzing each touch DNA sample. As shown in FIG. 44B, the touch DNA samples, such as samples 508a and 508b, are loaded on a conveyer 510 or other sample transportation system. Various technologies are then used to process each touch DNA sample, such as an optical identifier 512, a seal stripper 514, a sample locator 516, a sample analyzer/tester 518, a sample re-sealer 520, and a sample re-labeler 522. It can be appreciated that these processes are possible due to the relatively identical size, shape, identification and overall construction of the touch DNA samples. Of course, other processes may also be used in accordance with the present invention. As shown in FIG. 44C, these processes are used to generate a sample testing output sheet 524 and to prepare the samples for storage. This is just one of many ways in which automated and/or semi-automated technologies and equipment may be used to assist with the ease and speed of touch DNA sample analysis.

C. System Overview

Figure 45:
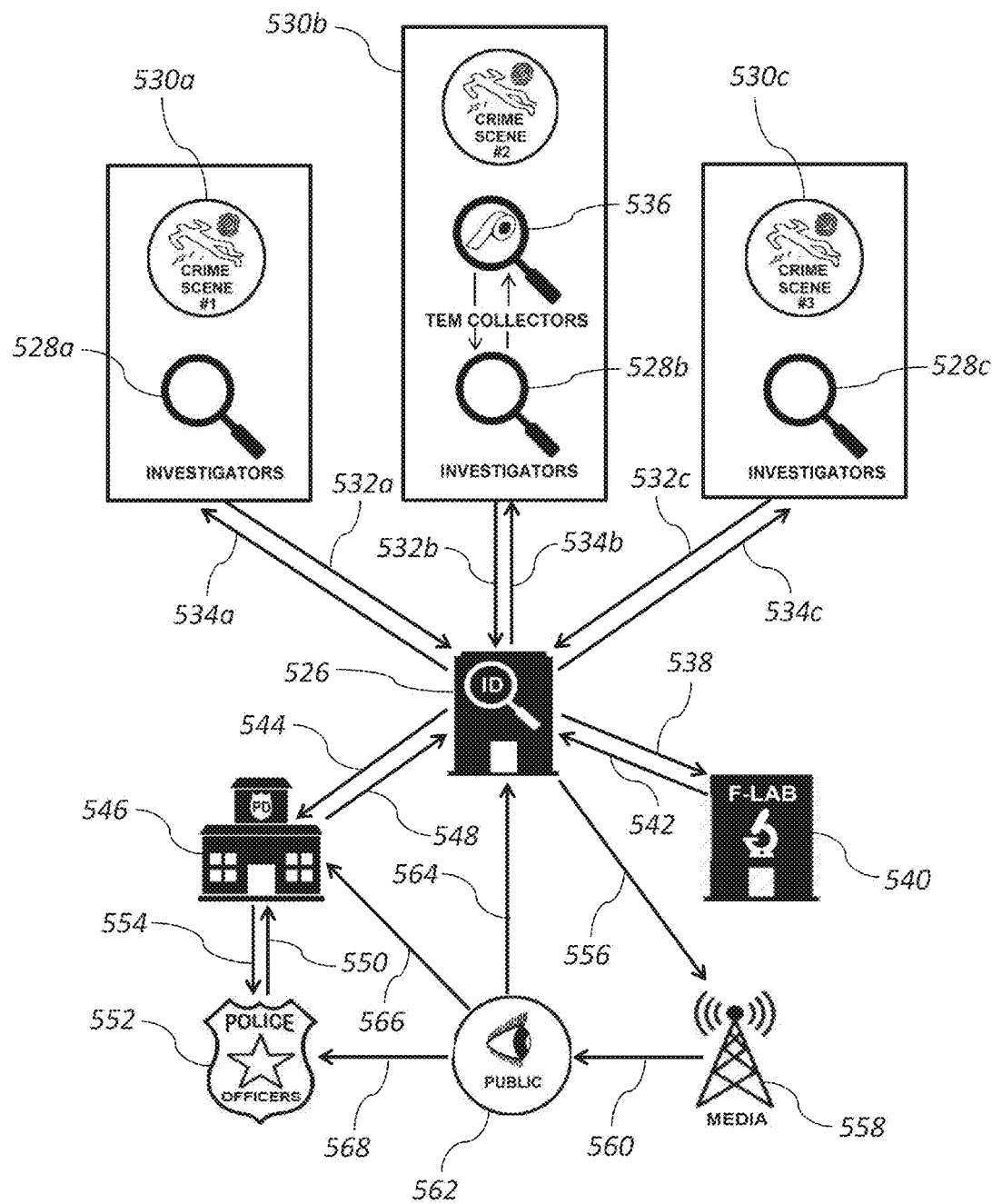
FIG. 45 provides an overview of the various elements and communication links of an exemplary TEM collection, analysis and distribution system in accordance with the present invention.

FIG. 45 provides an overview of the various elements and communication links of an exemplary TEM collection, analysis and distribution system in accordance with the present invention. The system includes an investigative department 526 that leads the investigation and acts as a central investigative, data and communication hub. Of course, there could be more than one department or entity serving these functions in other embodiments. Preferably, investigative department 526 determines which data will be sent or provided to other elements of the system, although other elements of the system may be able to make similar decisions depending on the needs and desires of the overall investigative body and process.

In this example, investigative department 526 sends investigators 528a, 528b and 528c to one or more suspected crime scenes or other investigative locations, which are depicted as crime scene #1 530a, crime scene #2 530b and crime scene #3 530c. At crime scene #1 530a and crime scene #3 530c, investigators 528a and 528c, respectively, perform their investigations as they normally would while also making use of multiple TEM collection devices, such as TEM collection device 100 and/or TEM collection device 400. At crime scene #2 530b, investigators 528b (such as investigators in a large investigation) may decide to use one or more specifically trained "TEM Recovery Specialists" or "Forensic Intelligence Specialists" (referred to herein as TEM collectors 536) to perform some of the TEM recovery efforts using the TEM collection devices. These efforts would be at the direction of the more highly skilled crime scene investigators 528b whose time may be better utilized in connection with overall crime scene analyzation, execution and TEM/crime scene information dissemination than the actual collection of all of the TEMs. This enables more efficient use of existing crime scene investigator personnel.

With the use of TEM collectors 536, investigators 528b can use TEM recovery guidance software built into the TEM collection devices or other similar devices. This software makes it very easy for investigators 528b to input existing crime scene floor plans or quickly draw up their own if desired. This software is designed to make it very easy for investigators 528b to assign multiple TEM recovery points to one or more TEM collectors 536 who are trained and certified in the procedures and use of the TEM collection devices and/or other desired TEM recovery methods.

Each of TEM collectors 536 would have his/her own software/tablet or similar device that wirelessly communicates in real-time with the investigator's TEM recovery software. This software can provide TEM collectors 536 with a list, floor plans and other TEM location identifiers and any other TEM recovery instructions. Investigators 528b can use an easily customizable check-off, location/procedure list that has typical TEM recovery points, such as tables, floors, beds, chairs, doorknobs etc., built-in to the software to facilitate the quick and easy generation of the list. As each TEM collector 536 completes a specific recovery point, he/she checks off that point as complete and investigators 528*b* and investigative department 526 or other entities can be notified of this in real-time.

While using the TEM collection devices, data streams 532*a*, 532*b* and 532*c* are transmitted in real-time from the TEM collection devices and other sources to investigative department 526. Each of these data streams may include, for example, digital images and video of TEMs, the wide angle crime scene video/audio, the close-up video of the surface being taped or swabbed, the high-resolution, high magnification video of the collected TEMs, the TEM collector's audio/written/drawn crime scene annotations, and all of the other TEM collection position/location data as described above. Investigative department 526 acts as a central repository for this and other data. It should be noted that investigative department 526 does not have to review or otherwise use the data as it comes in from the crime scenes (although the data is there if needed). Investigative department 526 and other elements of the system may utilize various optical color, shape and pattern recognition technologies to simultaneously sift through one or more of the different crime scenes images, video and data so as to assist with the association of objects, individuals or locations more quickly than possible with existing methods.

As investigators 528*a*, 528*b* and 528*c*, investigative department 526 and other sources examine the crime scene and related data, investigative department 526 may selectively transmit data streams 534*a*, 534*b* and 534*c* to the crime scenes in order to provide input and direction to investigators 528*a*, 528*b* and 528*c*, respectively. This may help the investigators to perform their investigation and TEM collection efforts more optimally so as to be able to utilize available investigative resources and personnel as efficiently as possible.

Investigative department 526 also transmits a data stream 538 to a forensic laboratory 540 (or multiple forensic laboratories). In this example, investigative department 526 transmits data stream 538 to forensic laboratory 540 in real-time so that forensic laboratory 540 can have access to and utilize all of the available TEM and crime scene collection data as desired. Data stream 538 can include, for example, digital images and video of TEMs, the wide angle crime scene video/audio, the close-up video of the surface being taped or swabbed, the high-resolution, high magnification video of the collected TEMs, the TEM collector's audio/written/drawn crime scene annotations, and all of the other precision TEM collection position/location data, as well as input from investigative department 526. It should be noted that forensic laboratory 540 does not have to review or otherwise use the data as it comes in from investigative department 526 (although the data is there if needed). Forensic laboratory 540 may also utilize various optical color, shape and pattern recognition technologies to simultaneously sift through one or more of the different crime scenes images, video and data so as to assist with the association of objects, individuals or locations more quickly than possible with existing methods. It can be appreciated that forensic laboratory 540 may also transmit a data stream 542 to investigative department 526 as required.

Investigative department 526 may also transmit a data stream 544 to a police department 546 and, conversely, police department may also transmit a data stream 548 to investigative department 526 as required. It should be understood that investigative department 526 determines the data that needs to be sent to police department 526. Police department 546 may further transmit a data stream 550 to police officers 552 or similar personnel. Data stream 550 may comprise all or any subset of the data transmitted to police department 546 by investigative department 526, such as instructions to keep a look out for people, automobiles, objects, etc. which may be based on the various information and data described above. Of course, police officers 552 may also transmit a data stream 554 to police department 546.

Investigative department 526 may also transmit a data stream 556 to the media 558 or similar public informational outlets, such as via the internet or to public attention/watch services (e.g., the watch service described as the "Amber Alert"). The media 558 may transmit a data stream 560 to the public 562 or similar broad public or private audiences. The public 562 may also send information 564 to investigative department 526, such as a sighting of a specific individual, automobile, object, etc. Similarly, the public 562 may send information 566 to police department 546 or information 568 to police officers 552 as is sometimes the case in public attention notices.

It can be appreciated that the overall intent of the TEM collection, analysis and distribution system described above is to illustrate how information and data generated by crime scene investigations can be quickly and broadly distributed in various ways that are beneficial to crime scene investigations, and is not meant to define a ridged structure for doing so. It should also be understood that the elements depicted in FIG. 27 are examples and that certain elements may not be used and other elements may be added in accordance with the present invention.

In view of the above, one skilled in the art will understand how the system of the present invention can be used to solve crimes. The system allows crime scene investigators to quickly and easily collect, analyze, annotate, securely store and electronically distribute large amounts of TEMs and related crime scene information while also making compliance with required trace evidence recovery procedures and documentation requirements quicker and easier. The system also makes it easy to analyze the collected TEMs along with the corresponding location and other data generated during TEM collection so that the forensic examiners have greater knowledge of the TEM collection and crime scene information to assist with their analysis of the crime scene. In addition, the system serves to decrease investigative TEM collection time and cost while also greatly increasing the ability of crime scene investigators to use TEMs to solve crimes.

D. General

The description set forth above provides several embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The use of any and all examples or exemplary language (e.g., "such as") provided with respect to certain embodiments is intended merely to better describe the invention and does not pose a limitation on the scope of the invention. No language in the description should be construed as indicating any non-claimed element essential to the practice of the invention.

While the present invention has been described and illustrated hereinabove with reference to several exemplary embodiments, it should be understood that various modifications could be made to these embodiments without departing from the scope of the invention. Therefore, the present invention is not to be limited to the specific structural configurations or methodologies of the exemplary embodiments, except insofar as such limitations are included in the following claims.

What is claimed and desired to be secured by Letters Patent is as follows:

1. A trace evidence material (TEM) collection device for collecting one or more TEMs from a surface, comprising:
   a supply reel configured to contain a roll of TEM collection media prior to collection of the TEMs, wherein the TEM collection media has a first side configured to collect one or more TEMs and a second back side;
   a roller configured for movement across the surface, wherein the TEM collection media is fed from the supply reel and wrapped around the roller whereby movement of the roller causes the first side of the TEM collection media to roll across the surface and collect the TEMs located on the surface; and
   a sealing assembly configured to seal the TEM collection media through application of a seal to the first side of the TEM collection media, wherein the sealing assembly is positioned to seal the TEM collection media after diverging from the roller after collection of the TEMs so as to preserve the collected TEMs.

2. The TEM collection device of claim 1, further comprising a take-up reel configured to store the roll of the TEM collection media with the seal applied thereto after collection of the TEMs.

3. The TEM collection device of claim 1, further comprising a cutting assembly configured to cut the TEM collection media with the seal applied thereto after collection of the TEMs to provide a sealed segment that is ejected from the device.

4. The TEM collection device of claim 1, wherein the TEM collection media is further sealed through application of a second seal to the second back side of the TEM collection media so as to preserve the collected TEMs between the seal and the second seal.

5. The TEM collection device of claim 1, wherein the collected TEMs are preserved between the seal and the second back side of the TEM collection media.

6. The TEM collection device of claim 1, wherein the TEM collection media comprises a collection tape.

7. The TEM collection device of claim 1, wherein the TEM collection media comprises a substrate and a plurality of absorbent swabbing pads spaced along and attached to the substrate.

8. The TEM collection device of claim 7, further comprising a swab moisture applicator that moistens each of the swabbing pads prior to collection of the TEMs.

9. The TEM collection device of claim 1, further comprising one or more cameras that capture one or more videos or photographs, wherein each of the cameras comprises one of: (a) a first camera that captures a video or a photograph of a crime scene; (b) a second camera that captures a video or a photograph of the surface prior to collection of the TEMs; and (c) a third camera that captures a video or a photograph of the TEM collection media after collection of the TEMs.

10. A trace evidence material (TEM) collection device for collecting one or more TEMs from a surface, comprising:
    a handle;
    a cassette drive mechanism attached to the handle; and
    a single-use cassette that is attachable to the cassette drive mechanism, wherein the cassette includes a plurality of components at least one of which is driven by the cassette drive mechanism to assist with movement of the TEM collection media across the surface, wherein the cassette comprises: (a) a supply reel configured to contain a roll of TEM collection media prior to collection of the TEMs, wherein the TEM collection media has a first side configured to collect one or more TEMs and a second back side; (b) a TEM collection media supporting member configured for movement across the surface, wherein the TEM collection media is fed from the supply reel and wrapped around the TEM collection media supporting member whereby movement of the TEM collection media supporting member causes the first side of the TEM collection media to move across the surface and collect the TEMs located on the surface; and (c) a sealing assembly configured to seal the TEM collection media through application of a seal to the first side of the TEM collection media, wherein the sealing assembly is positioned to seal the TEM collection media after diverging from the TEM collection media supporting member after collection of the TEMs so as to preserve the collected TEMs.

11. The TEM collection device of claim 10, wherein the cassette further comprises a take-up reel configured to store the roll of the TEM collection media with the seal applied thereto after collection of the TEMs.

12. The TEM collection device of claim 10, wherein the cassette further comprises a cutting assembly configured to cut the TEM collection media with the seal applied thereto after collection of the TEMs to provide a sealed segment that is ejected from the device.

13. The TEM collection device of claim 10, wherein the TEM collection media is further sealed through application of a second seal to the second back side of the TEM collection media so as to preserve the collected TEMs between the seal and the second seal.

14. The TEM collection device of claim 10, wherein the collected TEMs are preserved between the seal and the second back side of the TEM collection media.

15. The TEM collection device of claim 10, wherein the TEM collection media comprises a collection tape.

16. The TEM collection device of claim 10, wherein the TEM collection media comprises a substrate and a plurality of absorbent swabbing pads spaced along and attached to the substrate.

17. The TEM collection device of claim 10, further comprising one or more cameras that capture one or more videos or photographs, wherein each of the cameras comprises one of: (a) a first camera that captures a video or a photograph of a crime scene; (b) a second camera that captures a video or a photograph of the surface prior to collection of the TEMs; and (c) a third camera that captures a video or a photograph of the TEM collection media after collection of the TEMs.

18. The TEM collection device of claim 17, further comprising a computing device with a display that presents the one or more videos or photographs captured by the one or more cameras.

19. The TEM collection device of claim 18, wherein the computing device enables entry of one or more annotations relating to the one or more videos or photographs presented on the display.

20. The TEM collection device of claim 10, wherein the single-use cassette is packaged in a peel pouch prior to use.

21. The TEM collection device of claim 20, wherein the single-use cassette is placed in the peel pouch after collection of the TEMs and sealed with a chain of custody label.

22. A trace evidence material (TEM) collection device for collecting one or more TEMs from a surface, comprising:
- a handle;
- a cassette drive mechanism attached to the handle; and
- a plurality of single-use cassettes each of which is attachable to the cassette drive mechanism, wherein each of the cassettes includes a plurality of components at least one of which is driven by the cassette drive mechanism to assist with movement of the TEM collection media across the surface, wherein the cassette comprises (a) a supply reel configured to contain a roll of TEM collection media prior to collection of the TEMs, wherein the TEM collection media has a first side configured to collect one or more TEMs and a second back side; and (b) a roller configured for movement across the surface, wherein the TEM collection media is fed from the supply reel and wrapped around the roller whereby movement of the roller causes the first side of the TEM collection media to roll across the surface and collect the TEMs located on the surface.

23. The TEM collection device of claim 22, wherein the TEM collection media comprises one of (a) a collection tape and (b) a substrate and a plurality of absorbent swabbing pads spaced along and attached to the substrate.

24. A trace evidence material (TEM) collection device for collecting one or more TEMs from a surface, comprising:
- a handle;
- a cassette drive mechanism attached to the handle;
- a cassette that is attachable to the cassette drive mechanism, wherein the cassette comprises a roller configured to cause a collection tape to roll across the surface and collect TEMs located on the surface;
- a camera positioned to capture a video or a photograph of the collection tape after diverging from the roller after collection of the TEMs; and
- a computing device with a display that presents the video or the photograph captured by the camera and enables entry of a plurality of annotations relating to the video or the photograph presented on the display.

* * * * *